US012569215B2

(12) United States Patent
Horiuchi et al.

(10) Patent No.: US 12,569,215 B2
(45) Date of Patent: Mar. 10, 2026

(54) IMAGING MANAGEMENT DEVICE, METHOD FOR OPERATING IMAGING MANAGEMENT DEVICE, AND OPERATION PROGRAM FOR IMAGING MANAGEMENT DEVICE

(71) Applicant: FUJIFILM CORPORATION, Tokyo (JP)

(72) Inventors: Hisatsugu Horiuchi, Tokyo (JP); Koji Taninai, Tokyo (JP); Masataka Sugahara, Tokyo (JP); Kazuyuki Ogi, Tokyo (JP); Atsushi Onoda, Tokyo (JP)

(73) Assignee: FUJIFILM CORPORATION, Tokyo (JP)

( * ) Notice: Subject to any disclaimer, the term of this patent is extended or adjusted under 35 U.S.C. 154(b) by 411 days.

(21) Appl. No.: 18/181,547

(22) Filed: Mar. 10, 2023

(65) Prior Publication Data

US 2023/0293134 A1     Sep. 21, 2023

(30) Foreign Application Priority Data

Mar. 18, 2022     (JP) ................................. 2022-044572

(51) Int. Cl.
　　*A61B 6/00*　　　　(2024.01)
　　*A61B 6/04*　　　　(2006.01)
(52) U.S. Cl.
　　CPC ............ *A61B 6/548* (2013.01); *A61B 6/0407* (2013.01)
(58) Field of Classification Search
　　CPC ..... A61B 6/0407; A61B 6/4417; A61B 6/465; A61B 6/548; G16H 40/63
　　See application file for complete search history.

(56) References Cited

U.S. PATENT DOCUMENTS 7,848,490 B2 *　12/2010　Venturino .............. A61B 6/548
　　　　　　　　　　　　　　　　　　　　　　378/116
8,682,953 B2 *　3/2014　Wedel .................... G16H 40/63
　　　　　　　　　　　　　　　　　　　　　　709/201

(Continued)

FOREIGN PATENT DOCUMENTS

JP　　　2004-199194 A　　7/2004
JP　　　2005-092458 A　　4/2005

(Continued)

OTHER PUBLICATIONS

English language translation of the following: Office action dated Dec. 9, 2025 from the JPO in a Japanese patent application No. 2022-044572 corresponding to the instant patent application. This office action translation is submitted now in order to supplement the understanding of the cited references which are being disclosed in the instant Information Disclosure Statement.

*Primary Examiner* — David J Makiya
*Assistant Examiner* — Soorena Kefayati
(74) *Attorney, Agent, or Firm* — SOLARIS Intellectual Property Group, PLLC

(57)　　　　　　ABSTRACT

A CPU of an imaging management device has a status recognition unit, an entrance control unit, a speaker control unit, and a monitor control unit. The status recognition unit acquires progress status information indicating a progress status of radiography at each of the plurality of radiography rooms, such as subject position information indicating a position of a subject in the radiography room. The entrance control unit performs entrance control of the subject into the radiography room based on the progress status information. The speaker control unit and the monitor control unit perform output control of guide voice and guide information regarding imaging toward the subject. The entrance control by the entrance control unit and the output control by the speaker control unit and the monitor control unit are per- (Continued)

formed, thereby shifting the timing of the radiography at the plurality of radiography rooms.

11 Claims, 40 Drawing Sheets

(56)                    References Cited

U.S. PATENT DOCUMENTS

| | | | | |
|---|---|---|---|---|
| 10,146,907 | B2 * | 12/2018 | Seifert .................... | G16H 30/20 |
| 10,987,079 | B2 * | 4/2021 | Kawanishi ............. | G16H 40/67 |
| 2005/0063512 | A1 * | 3/2005 | Maschke .............. | A61B 6/4429 |
| | | | | 378/91 |
| 2006/0173270 | A1 * | 8/2006 | Weiner ................... | A61B 6/464 |
| | | | | 600/407 |
| 2008/0242915 | A1 * | 10/2008 | Jackson ................... | G21H 5/02 |
| | | | | 600/4 |
| 2009/0196398 | A1 * | 8/2009 | Ohara .................. | A61B 6/4494 |
| | | | | 378/98.8 |
| 2011/0013220 | A1 * | 1/2011 | Sabol ..................... | G16H 40/20 |
| | | | | 709/224 |
| 2011/0150182 | A1 * | 6/2011 | Omura ................ | A61B 6/4405 |
| | | | | 378/116 |
| 2013/0094628 | A1 * | 4/2013 | Lalena ................ | A61B 6/4405 |
| | | | | 378/98 |
| 2013/0184557 | A1 * | 7/2013 | Glaser-Seidnitzer .... | A61B 6/03 |
| | | | | 600/407 |
| 2013/0188629 | A1 * | 7/2013 | Lemaire .................. | H04W 4/80 |
| | | | | 370/338 |
| 2014/0010353 | A1 * | 1/2014 | Lalena ................... | A61B 6/465 |
| | | | | 378/207 |
| 2014/0177806 | A1 * | 6/2014 | Tachikawa ........... | A61B 6/4494 |
| | | | | 378/114 |
| 2016/0004818 | A1 * | 1/2016 | Seifert ................... | A61B 6/566 |
| | | | | 707/740 |
| 2016/0029991 | A1 * | 2/2016 | Tajima .................. | A61B 6/467 |
| | | | | 250/336.1 |
| 2016/0147955 | A1 * | 5/2016 | Shah ...................... | G16H 40/20 |
| | | | | 705/2 |
| 2016/0295094 | A1 * | 10/2016 | Endoh .................... | H04N 23/30 |
| 2017/0360390 | A1 * | 12/2017 | Tajima ................. | A61B 6/548 |
| 2019/0231299 | A1 * | 8/2019 | Lalena .................. | A61B 6/465 |
| 2019/0357866 | A1 | 11/2019 | Ohara | |
| 2020/0209409 | A1 * | 7/2020 | Uchiyama ............... | A61B 6/56 |
| 2020/0281547 | A1 * | 9/2020 | Imamura .............. | G06T 1/0007 |
| 2021/0050092 | A1 * | 2/2021 | Schirra ................. | G16H 40/20 |

FOREIGN PATENT DOCUMENTS

| | | |
|---|---|---|
| JP | 2007-202678 A | 8/2007 |
| JP | 2009-172242 A | 8/2009 |
| JP | 2012-147978 A | 8/2012 |
| JP | 2019-201929 A | 11/2019 |
| JP | 2021-186199 A | 12/2021 |
| WO | 2006/109551 A1 | 10/2006 |

* cited by examiner

FIG. 5

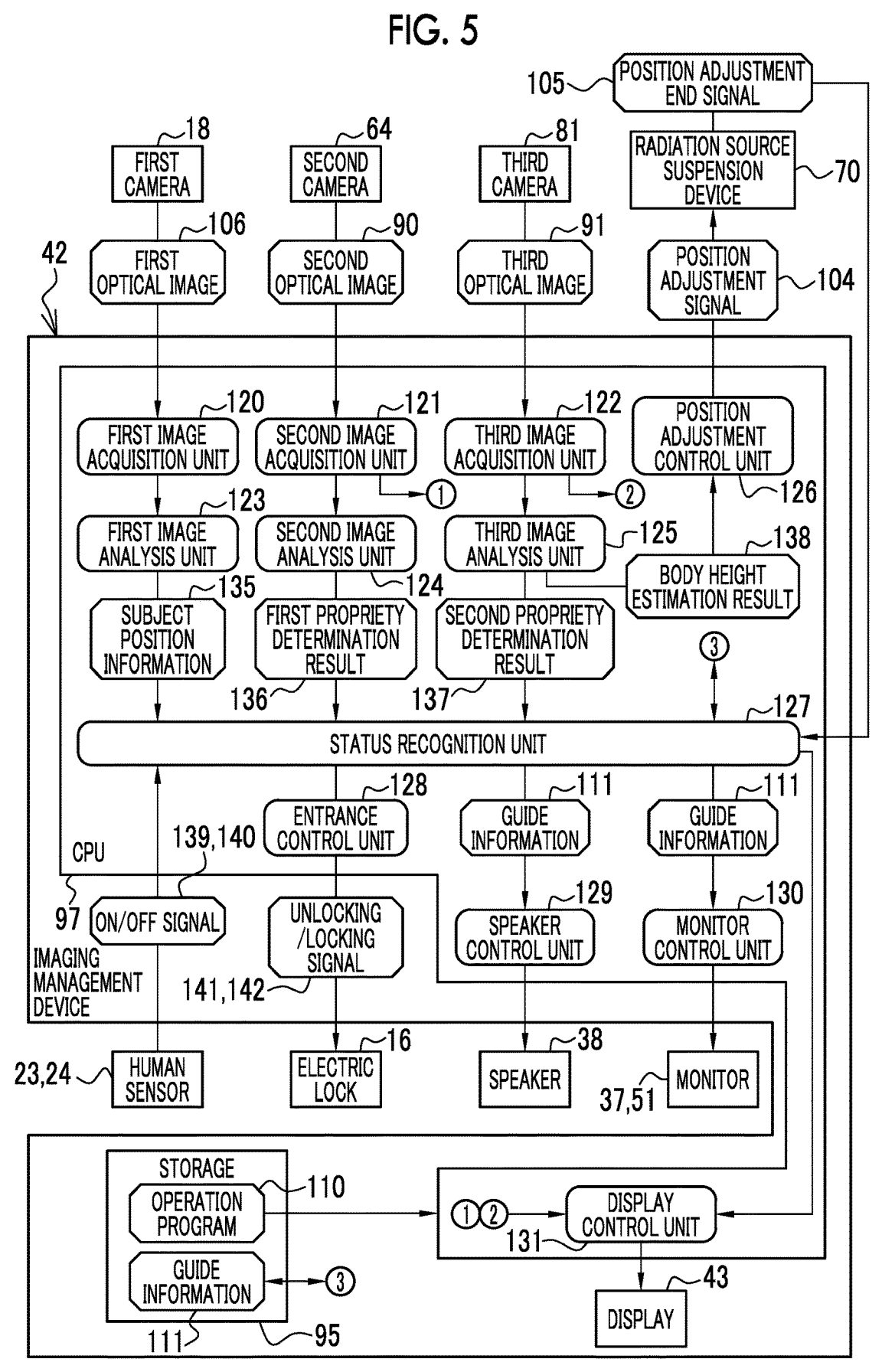

105 — POSITION ADJUSTMENT END SIGNAL

18 — FIRST CAMERA

64 — SECOND CAMERA

81 — THIRD CAMERA

RADIATION SOURCE SUSPENSION DEVICE — 70

106 — FIRST OPTICAL IMAGE

90 — SECOND OPTICAL IMAGE

91 — THIRD OPTICAL IMAGE

POSITION ADJUSTMENT SIGNAL — 104

42

120 — FIRST IMAGE ACQUISITION UNIT

121 — SECOND IMAGE ACQUISITION UNIT

122 — THIRD IMAGE ACQUISITION UNIT

POSITION ADJUSTMENT CONTROL UNIT — 126

①

②

123 — FIRST IMAGE ANALYSIS UNIT

SECOND IMAGE ANALYSIS UNIT

THIRD IMAGE ANALYSIS UNIT — 125

138 — BODY HEIGHT ESTIMATION RESULT

135 — SUBJECT POSITION INFORMATION

124 — FIRST PROPRIETY DETERMINATION RESULT

SECOND PROPRIETY DETERMINATION RESULT

③

136

137

STATUS RECOGNITION UNIT — 127

128 — ENTRANCE CONTROL UNIT

111 — GUIDE INFORMATION

111 — GUIDE INFORMATION

CPU 139,140

97 — ON/OFF SIGNAL

UNLOCKING /LOCKING SIGNAL

129 — SPEAKER CONTROL UNIT

130 — MONITOR CONTROL UNIT

IMAGING MANAGEMENT DEVICE 141,142

23,24 — HUMAN SENSOR

16 — ELECTRIC LOCK

38 — SPEAKER 37,51 — MONITOR

STORAGE

110 — OPERATION PROGRAM

①②

131 — DISPLAY CONTROL UNIT

43 — DISPLAY

GUIDE INFORMATION

③

111

95

PROGRESS STATUS: CHANGING CLOTHES at FIRST CHANGING ROOM (BEFORE IMAGING)

FIG. 10

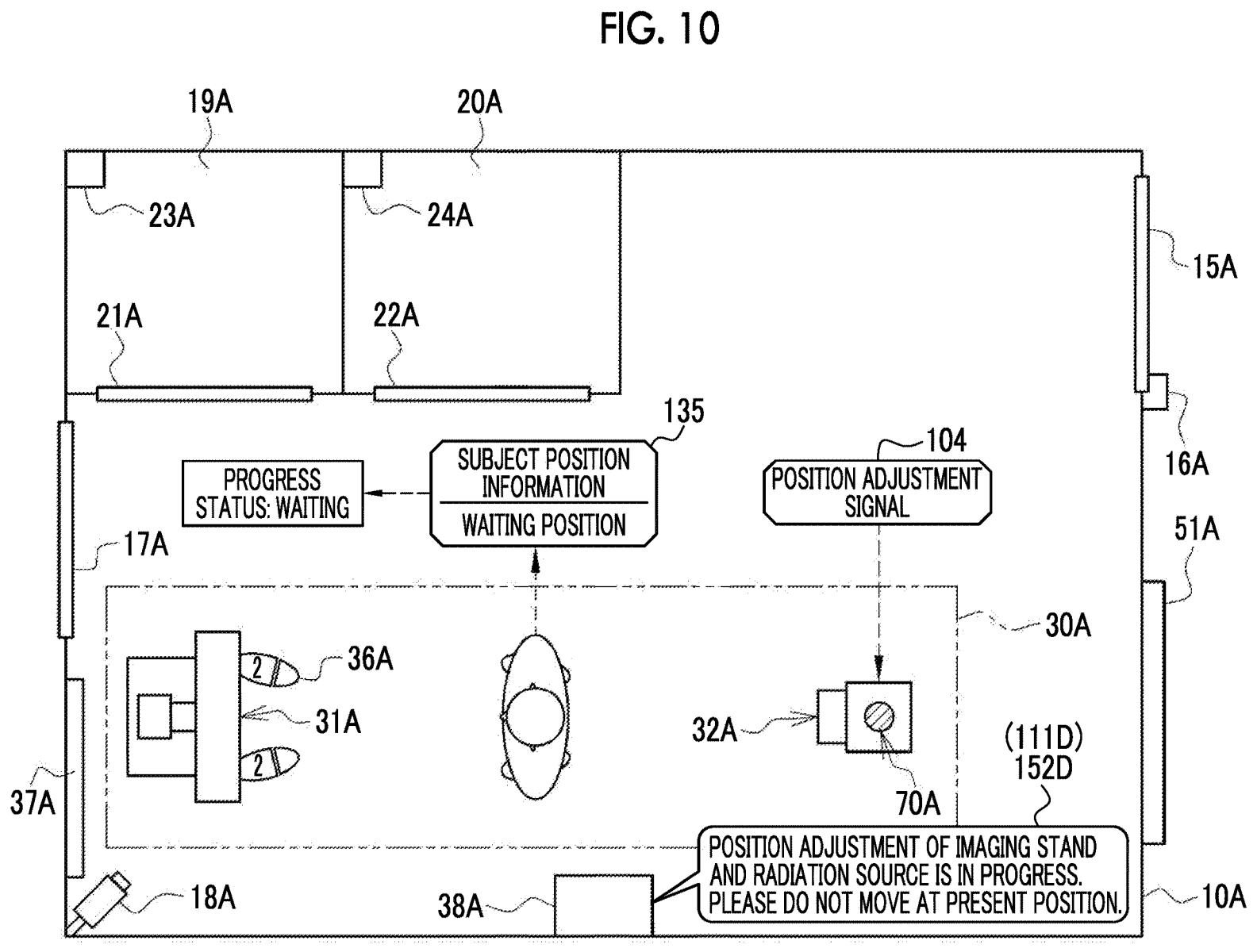

POSITION ADJUSTMENT SIGNAL 104

SUBJECT POSITION INFORMATION / WAITING POSITION 135

PROGRESS STATUS: WAITING (111D) 152D

POSITION ADJUSTMENT OF IMAGING STAND AND RADIATION SOURCE IS IN PROGRESS. PLEASE DO NOT MOVE AT PRESENT POSITION.

Figures 16A, 16B:
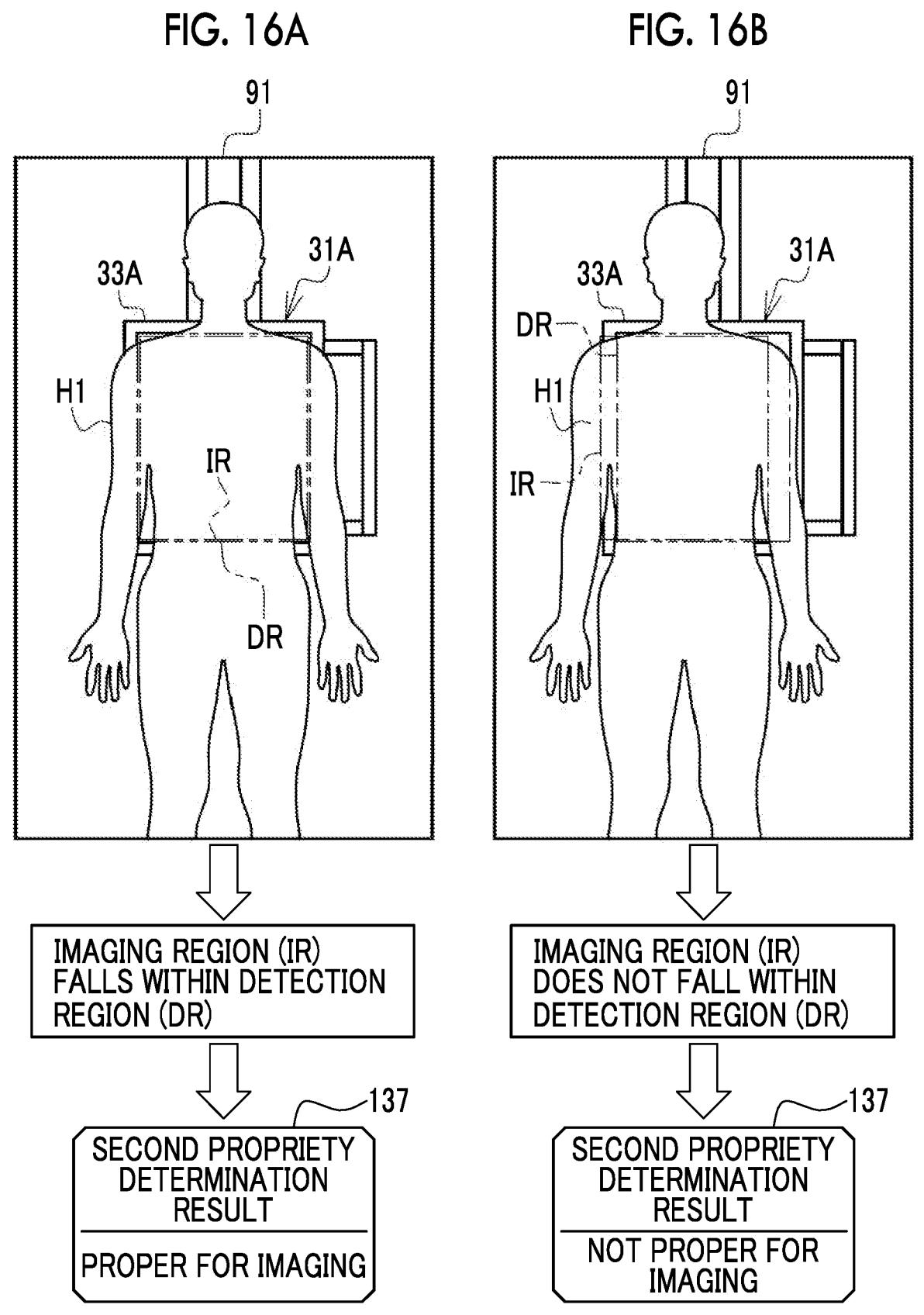

IMAGING REGION (IR)
FALLS WITHIN DETECTION
REGION (DR)

⬇

137

SECOND PROPRIETY
DETERMINATION
RESULT

PROPER FOR IMAGING

IMAGING REGION (IR)
DOES NOT FALL WITHIN
DETECTION REGION (DR)

⬇

137

SECOND PROPRIETY
DETERMINATION
RESULT

NOT PROPER FOR
IMAGING

PROGRESS STATUS: CHANGING CLOTHES at FIRST CHANGING ROOM (AFTER IMAGING)

ON SIGNAL

TIME

BREATHING-BODY
MOVEMENT
DETECTION RESULT

IMAGING MANAGEMENT DEVICE, METHOD FOR OPERATING IMAGING MANAGEMENT DEVICE, AND OPERATION PROGRAM FOR IMAGING MANAGEMENT DEVICE

CROSS-REFERENCE TO RELATED APPLICATIONS

The present application claims priority under 35 U.S.C. § 119 to Japanese Patent Application No. 2022-044572, filed on Mar. 18, 2022. The above application is hereby expressly incorporated by reference, in its entirety, into the present application.

BACKGROUND

1. Technical Field

A technique of the present disclosure relates to an imaging management device, a method for operating an imaging management device, and an operation program for an imaging management device.

2. Description of the Related Art

In a comparatively large-scale medical facility, such as a university hospital, a plurality of medical imaging systems (for example, radiography systems) are installed at a plurality of imaging rooms, for example, one by one. In the paragraph [0036] of WO2006/109551A, a technique for collectively managing imaging with a plurality of medical imaging systems installed at a plurality of imaging places has been suggested.

SUMMARY

Here, a case where imaging with a plurality of medical imaging systems installed at a plurality of imaging places is managed by a number of operators smaller than the number of imaging places for efficiency is considered. In this case, an operator who has a qualification needs to instruct imaging, and an operator who manages imaging at a plurality of imaging places should instruct imaging at a plurality of imaging places one by one. Under such a condition, in a case where the timing of imaging conflicts at several imaging places, the operator may be confused.

An embodiment according to the technique of the present disclosure provides an imaging management device, a method for operating an imaging management device, and an operation program for an imaging management device capable of suppressing a situation causing confusion of an operator in a case of managing imaging with a plurality of medical imaging systems installed at a plurality of imaging places.

An imaging management device of the present disclosure is an imaging management device that manages imaging with a plurality of medical imaging systems installed at a plurality of imaging places, the imaging management device comprising a processor, in which the processor is configured to acquire progress status information indicating a progress status of the imaging at each of the plurality of imaging places and perform at least one of access control to the imaging place of a subject to be a target of the imaging or output control of guide information regarding the imaging toward the subject based on the progress status information to shift timing of the imaging at the plurality of imaging places.

It is preferable that the progress status information includes imaging preparation completion information indicating that preparation of the imaging is completed and the timing of the imaging is reached, and the processor is configured to notify an operator that the timing of the imaging is reached, in a case where the imaging preparation completion information is acquired.

It is preferable that the medical imaging system is a radiography system, and the processor is configured to acquire a position adjustment end signal indicating that adjustment of positions of a radiation source that performs irradiation of radiation and a radiographic image detector that receives the radiation to detect a radiographic image ends, as the imaging preparation completion information.

It is preferable that the processor is configured to acquire a determination result that a status of the subject is proper for the imaging, as the imaging preparation completion information.

It is preferable that the processor is configured to acquire a determination result that a degree of close contact of the subject with an imaging stand on which the subject is positioned for the imaging is proper for the imaging, as the imaging preparation completion information.

It is preferable that the medical imaging system is a radiography system, and the processor is configured to acquire a determination result indicating that an imaging region as a region to be imaged in a radiographic image falls within a detection region for radiation of a radiographic image detector that receives the radiation to detect the radiographic image, as the imaging preparation completion information.

It is preferable that the processor is configured to acquire a determination result that a degree of stillness of the subject is proper for the imaging, as the imaging preparation completion information.

It is preferable that the processor is configured to acquire a detection result of body movement by breathing of the subject, and perform control for displaying an animation indicating transition of a breathing state of the subject based on the detection result on a display as the guide information.

It is preferable that the imaging place is at least one of an imaging room for the medical imaging system installed in a medical facility or a traveling examination car in which the medical imaging system is mounted.

It is preferable that the medical imaging system is a radiography system.

A method for operating an imaging management device of the present disclosure is a method for operating an imaging management device that manages imaging with a plurality of medical imaging systems installed at a plurality of imaging places, the method comprising acquiring progress status information indicating a progress status of the imaging at each of the plurality of imaging places, and performing at least one of access control to the imaging place of a subject to be a target of the imaging or output control of guide information regarding the imaging toward the subject based on the progress status information to shift timing of the imaging at the plurality of imaging places.

An operation program for an imaging management device of the present disclosure is an operation program for an imaging management device that manages imaging with a plurality of medical imaging systems installed at a plurality of imaging places, the operation program causing a computer to execute a process, the process comprising acquiring progress status information indicating a progress status of the imaging at each of the plurality of imaging places, and performing at least one of access control to the imaging place of a subject to be a target of the imaging or output control of guide information regarding the imaging toward the subject based on the progress status information to shift timing of the imaging at the plurality of imaging places.

According to the technique of the present disclosure, it is possible to provide an imaging management device, a method for operating an imaging management device, and an operation program for an imaging management device capable of suppressing a situation causing confusion of an operator in a case of managing imaging with a plurality of medical imaging systems installed at a plurality of imaging places.

BRIEF DESCRIPTION I/F THE DRAWINGS

Exemplary embodiments according to the technique of the present disclosure will be described in detail based on the following figures, wherein:

FIG. 5 is a block diagram showing processing units of a CPU of the imaging management device;

FIG. 10 is a diagram showing a case where the progress status of the radiography is "waiting";

FIG. 14A shows a case where a close contact degree is equal to or greater than a first threshold value and FIG. 14B shows a case where the close contact degree is less than the first threshold value;

FIG. 15 is a diagram showing processing of a third image analysis unit;

FIGS. 16A and 16B are diagrams showing the processing of the third image analysis unit, and FIG. 16A shows a case where an imaging region falls within a detection region and FIG. 16B shows a case where the imaging region does not fall within the detection region;

FIG. 32A shows a case where a movement amount is less than a second threshold value and FIG. 32B shows a case where the movement amount is equal to or greater than the second threshold value;

FIG. 36 is a diagram showing transition of an animation depending on a breathing state of the subject;

FIG. 38 is a diagram showing another example of transition of an animation depending on the breathing state of the subject;

DETAILED DESCRIPTION

First Embodiment

Figure 1:
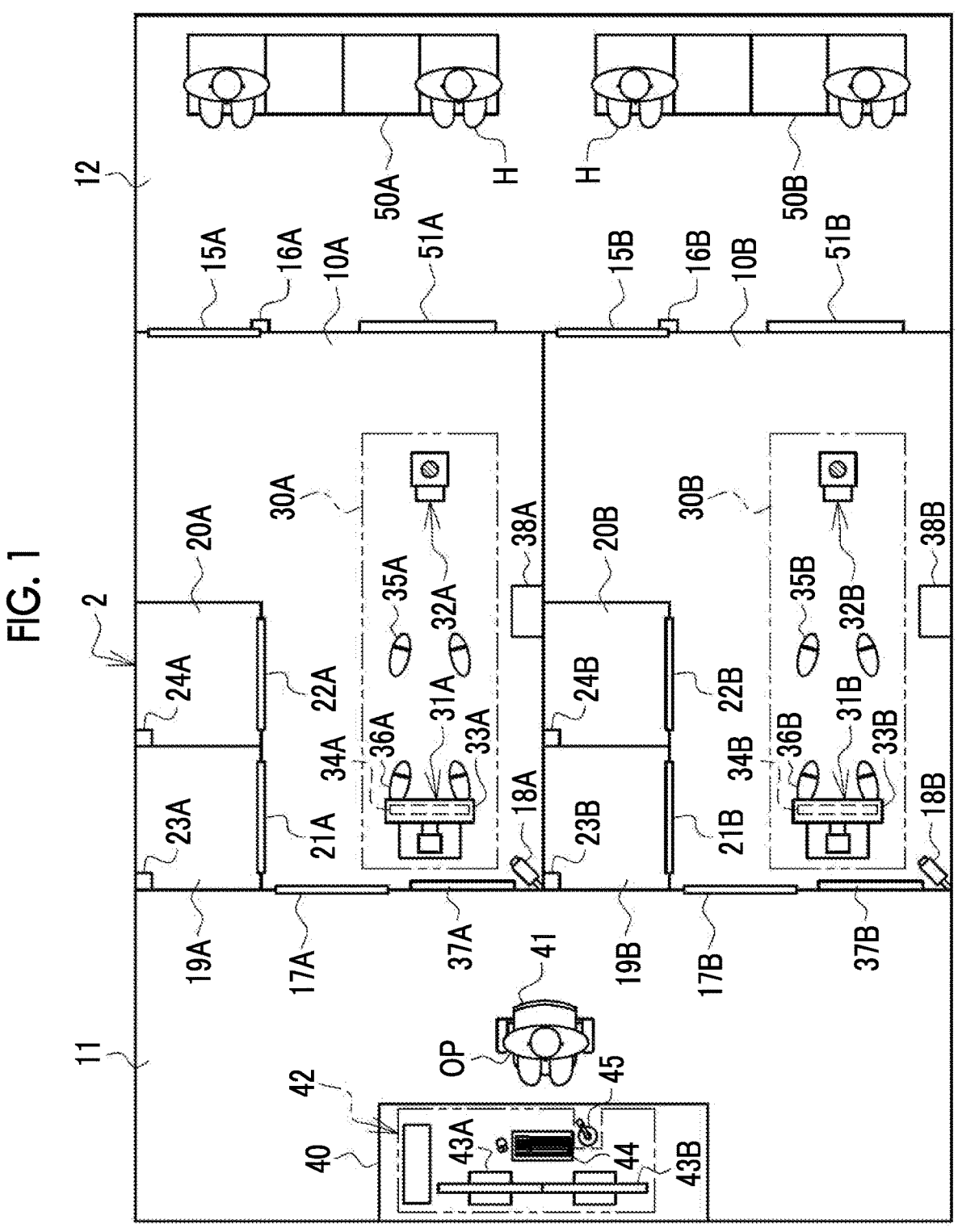
FIG. 1 is a bird's-eye view of a radiography room, a control room, and a waiting room of a radiology department of a certain medical facility.

FIG. 1 is a bird's-eye view of an example of a layout of a radiology department 2 of a certain medical facility viewed from a ceiling 73 (see FIG. 2) side. In the radiology department 2, there are two radiography rooms of radiography rooms 10A and 10B. There is one control room 11 common to the radiography rooms 10A and 10B next to the radiography rooms 10A and 10B. There is a waiting room 12 common to the radiography rooms 10A and 10B on a side opposite to the control room 11 with the radiography rooms 10A and 10B interposed therebetween. The radiography rooms 10A and 10B is an example of an "imaging place" according to the technique of the present disclosure.

The radiography rooms 10A and 10B have the same configuration. For this reason, hereinafter, only the configuration of the radiography room 10A will be described, each portion related to the radiography room 10B is represented by a reference numeral with "B" attached to the same numeral as the radiography room 10A, and description thereof will not be repeated. In the following description, the reference numerals of the radiography rooms 10A and 10B and the respective portions related to the radiography rooms 10A and 10B may be written by the numerals alone without "A" and "B" unless otherwise necessary to distinguish therebetween.

The radiography room 10A has a rectangular shape. At a corner of a wall surface of the radiography room 10A facing the waiting room 12, a first door 15A that opens and closes a doorway communicating with the waiting room 12 is provided. A subject H as a target of radiography can move between the radiography room 10A and the waiting room 12 through the first door 15A. An electric lock 16A is attached to the first door 15A. The first door 15A is unlocked or locked by the electric lock 16A.

At the center of a wall surface of the radiography room 10A on a side opposite to the side on which the first door 15A is provided, a second door 17A that opens and closes a doorway communicating with the control room 11 is provided. An operator OP, such as a radiographer, can move between the radiography room 10A and the control room 11 through the second door 17A.

A first camera 18A is attached to the ceiling 73 at a corner of the radiography room 10A diagonal to the corner at which the first door 15A is provided. The first camera 18A is a digital camera that captures a digital first optical image 106A (see FIG. 4). The first camera 18A is an omniazimuth camera that images a complete view of the radiography room 10A. The first camera 18A operates during a medical care time of the radiology department 2 and sequentially outputs the first optical images 106A at a predetermined frame rate. The first camera 18A is connected to a imaging management device 42 described below to be communicable in a wired or wireless manner and sequentially transmits the first optical images 106A to the imaging management device 42.

In a section on a side of the first door 15A between sections as the radiography room 10A is substantially bisected by a line parallel to a long side thereof, two changing rooms of a first changing room 19A and a second changing room 20A are provided. The first changing room 19A and the second changing room 20A are places where the subject H before the radiography changes clothes from his/her clothes to clothes for examination or where the subject H after the radiography changes clothes from clothes for examination to his/her clothes.

In the first changing room 19A, a third door 21A that opens and closes a doorway communicating with the radiography room 10A is provided. The subject H can move between the radiography room 10A and the first changing room 19A through the third door 21A. Similarly, in the second changing room 20A, a fourth door 22A that opens and closes a doorway communicating with the radiography room 10A is provided. The subject H can move between the radiography room 10A and the second changing room 20A through the fourth door 22A.

A first human sensor 23A is provided in the first changing room 19A, and a second human sensor 24A is provided in the second changing room 20A. The first human sensor 23A is turned on in a case where the subject H enters the first changing room 19A, and the second human sensor 24A is turned on in a case where the subject H enters the second changing room 20A. Though not shown, lockers are provided in the first changing room 19A and the second changing room 20A.

In a section on a side of the first camera 18A between the sections as the radiography room 10A is substantially bisected by the line parallel to the long side thereof, a radiography system 30A is provided. The radiography system 30A includes an upright imaging stand 31A and a radiation source 32A. The upright imaging stand 31A has a holder 33A. An electronic cassette 34A is accommodated in the holder 33A. The upright imaging stand 31A is an example of an "imaging stand" according to the technique of the present disclosure.

On a floor surface of the radiography room 10A between the upright imaging stand 31A and the radiation source 32A, first footprints 35A are painted with paint or the like. The first footprints 35A specify a waiting position, and are marks on which the subject H places both feet. The waiting position is a position determined in advance between the upright imaging stand 31A and the radiation source 32A, and is a position where the subject H does not obstruct adjustment of height positions and the like of the radiation source 32A and the holder 33A (electronic cassette 34A).

On a floor surface of the radiography room 10A directly below the upright imaging stand 31A, second footprints 36A are painted by paint or the like. The second footprints 36A specify an imaging position, and are marks on which the subject H places both feet. The imaging position is a standing position of the subject H that is recommended in chest/upright/front imaging to be most frequently performed.

An imaging room monitor 37A is attached to a wall surface of the radiography room 10A in front of the upright imaging stand 31A. The imaging room monitor 37A displays guide information 111 (see FIG. 5 and the like) regarding the radiography toward the subject H.

A speaker 38A is attached to an upper portion of a wall surface of the radiography room 10A on a side on which the radiography system 30A is provided. The speaker 38A outputs guide voice 152 (see FIG. 7 and the like) that is voice announcement of the guide information 111. The speaker 38A also outputs spoken voice of the operator OP in the control room 11. Although there are a plurality of kinds of guide voice 152, such as guide voice 152B (see FIG. 7) and guide voice 152C (see FIG. 9), as described below, in the following description, a plurality of kinds of guide voice 152B, 152C, and the like may be collectively written as guide voice 152.

In the control room 11, a console 40 is disposed at the center of a wall surface on a side opposite to the radiography room 10. The console 40 is at a height suitable for the operator OP to operate while setting on a chair 41. An imaging management device 42 is provided on the console 40. The imaging management device 42 is, for example, a desktop type personal computer. The imaging management device 42 has displays 43A and 43B, and an input device 44, such as a keyboard and a mouse. On the display 43A, information regarding the radiography room 10A toward the operator OP is displayed. On the display 43B, information regarding the radiography room 10B toward the operator OP is displayed. The input device 44 receives an operation instruction of the operator OP. A screen of one display 43 may be divided to display information regarding the radiography room 10A and information regarding the radiography room 10B.

Here, the number of operators OP disposed in the control room 11 is the number of people smaller than the number of radiography systems 30. In FIG. 1, a case where one operator OP is disposed for two radiography systems 30 is illustrated.

A microphone 45 is connected to the imaging management device 42. The microphone 45 collects spoken voice of the operator OP. The spoken voice of the operator OP collected by the microphone 45 is output from the speaker 38. The imaging management device 42 may be a notebook type personal computer, a tablet terminal, or the like.

In the waiting room 12, benches 50A and 50B on which the subjects H sit and wait are provided in front of the radiography rooms 10A and 10B, respectively. A waiting room monitor 51A is attached next to the first door 15A on a wall surface that faces the bench 50A and partitions the radiography room 10A and the waiting room 12. The waiting room monitor 51A displays information toward the subject H in the waiting room 12. Similarly, a waiting room monitor 51B is attached next to the first door 15B on a wall surface that faces the bench 50B and partitions the radiography room 10B and the waiting room 12. The waiting room monitor 51B displays information toward the subject H in the waiting room 12. The waiting room monitors 51A and 51B are equipped with speakers (not shown), and can output the guide voice 152 and spoken voice of the operator OP from the speakers. The waiting room 12 may also serve as a passage of the subject H and a person concerned of the medical facility including the operator OP.

Figure 2:
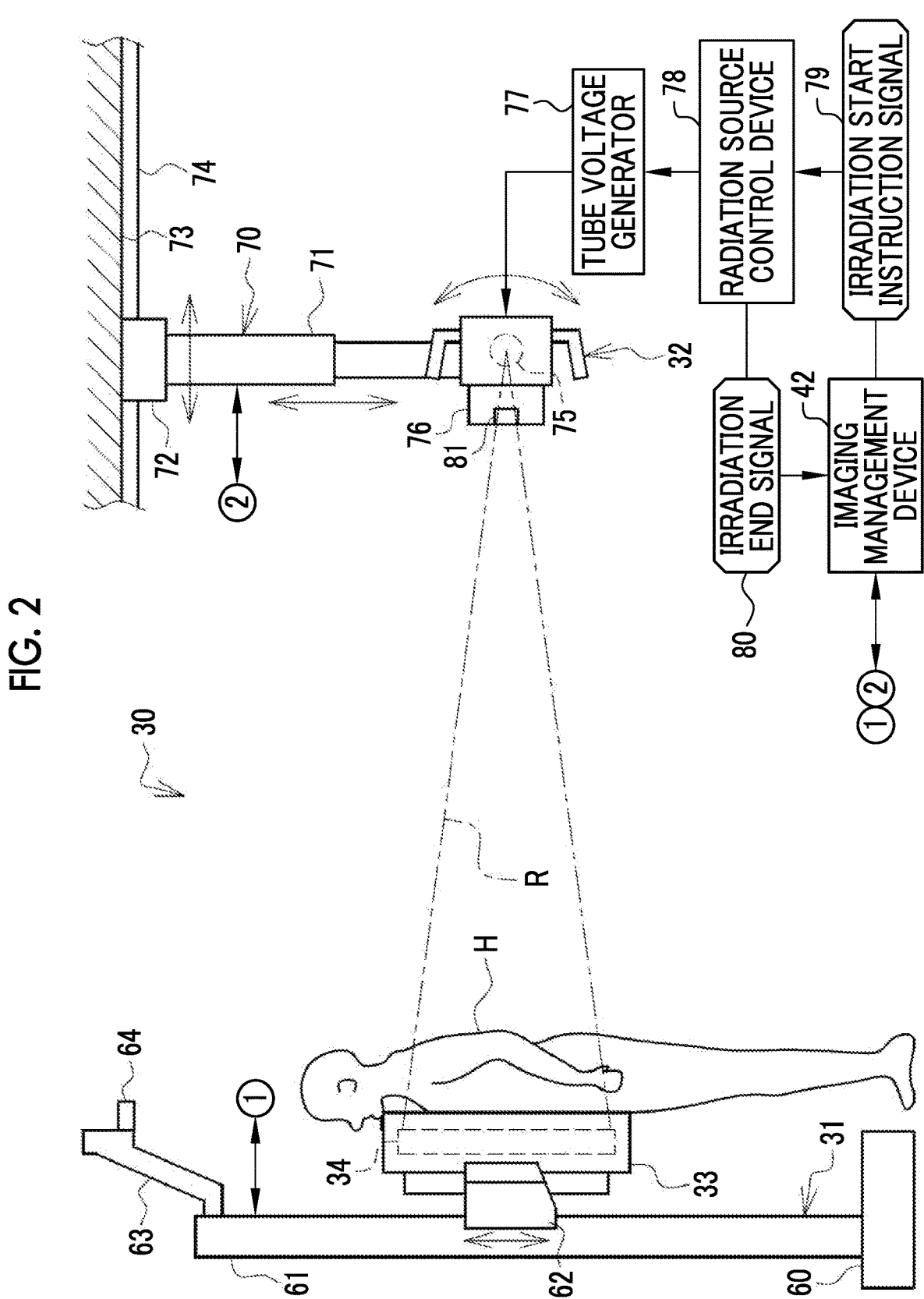
FIG. 2 is a diagram showing a radiography system.

As shown in FIG. 2 as an example, the radiography system 30 is a system that performs the radiography of the subject H using radiation R, such as X-rays or y-rays. The radiography system 30 is an example of a "medical imaging system" according to the technique of the present disclosure.

The upright imaging stand 31 is an imaging stand for radiographing the subject H in an upright posture. The upright imaging stand 31 has a pedestal 60 provided on the floor surface of the radiography room 10, a support 61 that extends in a height direction from the pedestal 60, and the above-described holder 33. The holder 33 is connected to the support 61 through a connection portion 62. The connection portion 62 and the holder 33 are moved up and down with respect to the support 61 by a motor or the like conforming to an imaging part or the physique of the subject H. The moving up and down of the holder 33 can be performed from the control room 11 through the imaging management device 42. A height position of the holder 33 is detected by, for example, a linear encoder.

A fixture 63 is provided in a distal end portion of the support 61. The fixture 63 protrudes obliquely upward from the distal end portion of the support 61 toward the holder 33 side. A second camera 64 is attached to the distal end portion of the fixture 63. The second camera 64 is a digital camera that captures a digital second optical image 90 (see FIG. 3). The second camera 64 operates from when a progress status of radiography is "position adjustment end" (see FIG. 11) to when the progress status of the radiography is "radiography end" (see FIG. 20), and sequentially outputs the second optical images 90 at a predetermined frame rate. The second camera 64 is connected to the imaging management device 42 to be communicable in a wired or wireless manner and sequentially transmits the second optical images 90 to the imaging management device 42.

The electronic cassette 34 is a portable radiographic image detector that detects a radiographic image 103 (see FIG. 4) depending on radiation R transmitted through the subject H. The electronic cassette 34 is connected to the imaging management device 42 to be communicable in a wired or wireless manner. The electronic cassette 34 can be accommodated in the holder 33 of the upright imaging stand 31 for use, and can also be detached from the holder 33 and carried by the subject H or can be inserted below the subject H who lies supine on a bed of a patient's room, for use. The electronic cassette 34 is an example of a "radiographic image detector" according to the technique of the present disclosure.

The electronic cassette 34 has a detection panel in which a plurality of pixels for accumulating electric charge depending on the radiation R are arranged in a two-dimensional matrix. The detection panel is also called a flat panel detector (FPD). In a case where the irradiation of the radiation R is started, the detection panel starts an accumulation operation to accumulate the electric charge in the pixels. In a case where the irradiation of the radiation R is ended, the detection panel starts a readout operation to read out the electric charge accumulated in the pixels as an electrical signal.

The radiation source 32 is attached to a distal end of an arm 71 of a radiation source suspension device 70. The radiation source suspension device 70 has a carriage 72 in addition to the arm 71. A proximal end of the arm 71 is attached to the carriage 72. The arm 71 can expand and contract along a vertical direction by a motor or the like. The arm 71 is made to expand and contract in the vertical direction, whereby a height position of the radiation source 32 can be changed conforming to the imaging part or the physique of the subject H. A position of expansion and contraction of the arm 71 and the height position of the radiation source 32 are detected by, for example, a linear encoder. The radiation source 32 is rotated around an axis perpendicular to the paper plane with respect to the arm 71 by a motor or the like to adjust an incidence angle of the radiation R on the subject H. A rotation angle of the radiation source 32 is detected by, for example, a rotary encoder or a potentiometer. Like the moving up and down of the holder 33, the moving up and down and the rotation of the radiation source 32 can also be performed from the control room 11 through the imaging management device 42.

The carriage 72 is connected to a rail 74 provided on the ceiling 73 of the radiography room 10. The rail 74 has a linear shape and is parallel to a normal line of a detection surface for the radiation R of the electronic cassette 34 accommodated in the holder 33. The carriage 72 and the radiation source 32 can be moved in parallel along the rail 74 by a motor or the like. The radiation source 32 is moved in parallel along the rail 74 in this way, whereby a source to image receptor distance (SID) that is a distance from a generation point of the radiation R to a detection surface for the radiation R of the electronic cassette 34 is changed. A position of the carriage 72 with respect to the rail 74 is detected by, for example, a linear encoder. Like the moving up and down of the holder 33, and the like, the parallel movement of the radiation source 32 can be performed from the control room 11 through the imaging management device 42.

The radiation source 32 has a radiation tube 75 and an irradiation field limiter 76. The radiation tube 75 is provided with a filament, a target, a grid electrode, and the like (all are not shown). A voltage is applied between the filament as a cathode and the target as an anode. The voltage that is applied between the filament and the target is referred to as a tube voltage. The filament discharges thermoelectrons depending on the applied tube voltage toward the target. The target radiates the radiation R with collision of the thermo-electrons from the filament. The grid electrode is disposed between the filament and the target. The grid electrode changes a flow rate of the thermoelectrons from the filament toward the target depending on the applied voltage. The flow rate of the thermoelectrons from the filament toward the target is referred to as a tube current.

The irradiation field limiter 76 is also called a collimator and limits an irradiation field of the radiation R emitted from the radiation tube 75. The irradiation field limiter 76 has, for example, a configuration in which four shield plates formed of lead or the like that shield the radiation R are disposed on respective sides of a quadrangle, and a quadrangular emission opening through which the radiation R is transmitted is formed in a center portion. The irradiation field limiter 76 changes a position of each shield plate to change the size of the emission opening, and accordingly, changes the irradiation field of the radiation R.

A tube voltage generator 77 is connected to the radiation source 32, and a radiation source control device 78 is connected to the tube voltage generator 77. Then, the imaging management device 42 is connected to the radiation source control device 78. The tube voltage generator 77 is disposed in the radiography room 10, and the radiation source control device 78 is disposed in the control room 11.

The tube voltage generator 77 boosts an input voltage by a transformer to generate a tube voltage. The tube voltage generated by the tube voltage generator 77 is supplied to the radiation tube 75 through a voltage cable (not shown).

The radiation source control device 78 controls the operation of the radiation source 32 in response to a irradiation start instruction signal 79 of the radiation R from the imaging management device 42. The irradiation start instruction signal 79 is a signal that is input through the input device 44 of the imaging management device 42 in a case where the operator OP instructs the radiation source 32 to start the irradiation of the radiation R. The irradiation start instruction signal 79 also serves as a warm-up instruction signal for make the radiation tube 75 perform a warm-up operation before the irradiation of the radiation R.

An irradiation condition of the radiation R is set in the radiation source control device 78. The irradiation condition is a tube voltage that is applied to the radiation tube 75, a tube current, and an irradiation time of the radiation R. In a case where the irradiation start instruction signal 79 is input from the imaging management device 42, the radiation source control device 78 operates the tube voltage generator 77 following the set irradiation condition, and causes the irradiation of the radiation R from the radiation tube 75. After the irradiation of the radiation R is started, in a case where the irradiation time set in the irradiation condition has elapsed, the radiation source control device 78 stops the irradiation of the radiation R from the radiation tube 75. The radiation source control device 78 transmits an irradiation end signal 80 indicating that the irradiation of the radiation R ends, to the imaging management device 42.

The irradiation of the radiation R may be ended by an auto exposure control (AEC) function. The AEC function is a function of detecting a dose of the radiation R to the electronic cassette 34 during the irradiation of the radiation R and stopping the irradiation of the radiation R from the radiation tube 75 at a point of time at which a cumulative dose that is an integrated value of the detected dose reaches a target dose set in advance. In this case, the detection panel of the electronic cassette 34 starts a readout operation in a case where the cumulative dose of the radiation R reaches the target dose.

A third camera 81 is attached to the center of a distal end of the irradiation field limiter 76 of the radiation source 32. The third camera 81 is a digital camera that captures a digital third optical image 91 (see FIG. 3). The third camera 81 operates from when the progress status of the radiography is "waiting" (see FIG. 10) to when the progress status of the radiography is "radiography end", and sequentially outputs the third optical images 91 at a predetermined frame rate. The third camera 81 is connected to the imaging management device 42 to be communicable in a wired or wireless manner and sequentially transmits the third optical images 91 to the imaging management device 42. The third camera 81 may be incorporated in the irradiation field limiter 76.

Figure 3:
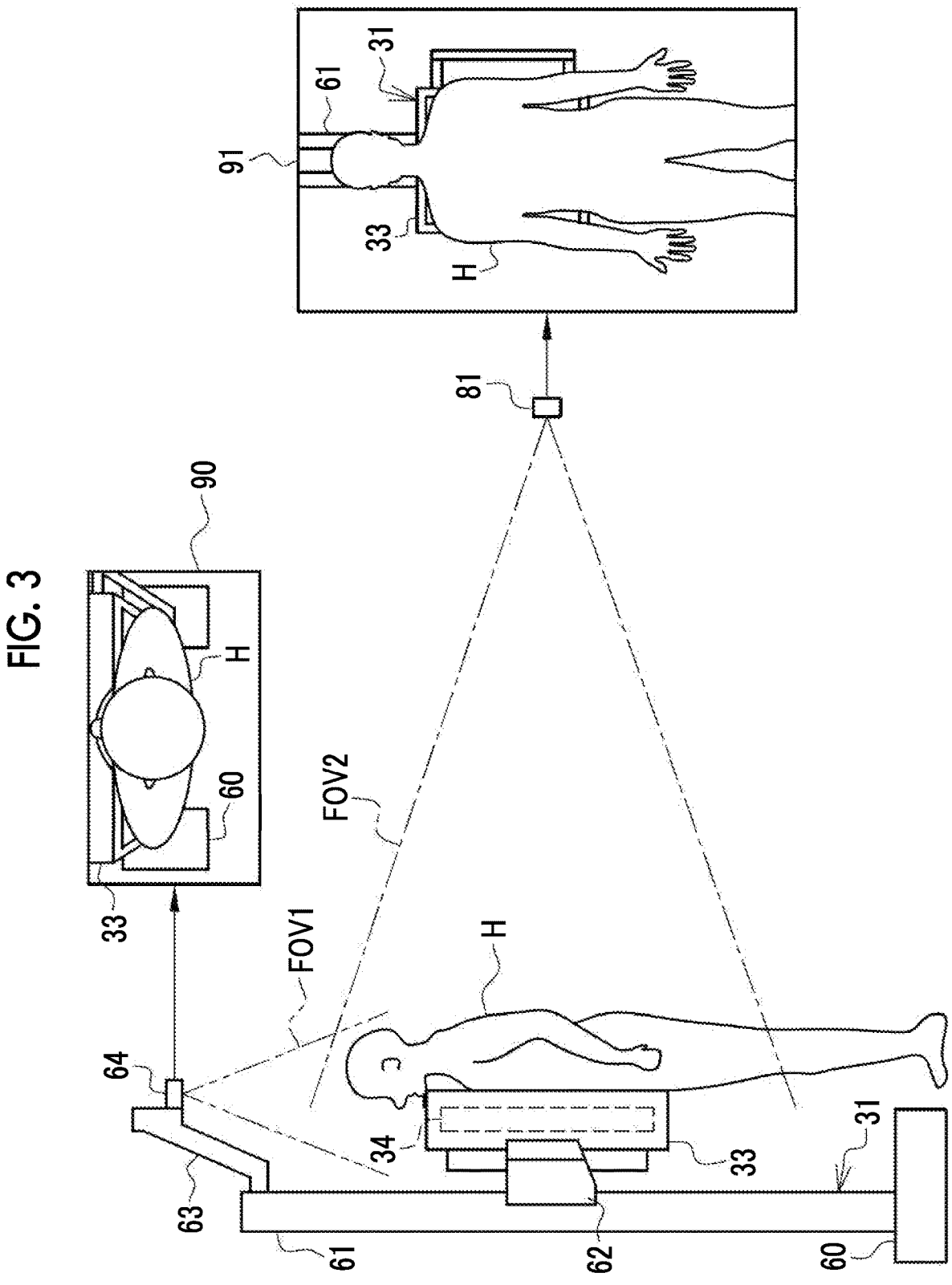
FIG. 3 is a diagram showing a second optical image captured with a second camera and a third optical image captured with a third camera.

FIG. 3 shows an example of an aspect where the subject H who stands in front of the upright imaging stand 31 is imaged with the second camera 64 and the third camera 81. The second camera 64 has a field of view FOV1 capable of imaging the holder 33 and a region between the holder 33 and the subject H who stands in front of the upright imaging stand 31. In the second optical image 90 captured with the second camera 64 in this way, the holder 33 and the region between the holder 33 and the subject H who stands in front of the upright imaging stand 31 are shown. On the other hand, the third camera 81 has a field of view FOV2 capable of imaging a portion from a head top to below a knee (the whole of an upper body and a part of a lower body) of a back of the subject H who stands in front of the upright imaging stand 31 in chest/upright/front imaging. In the third optical image 91 captured with the third camera 81 in this way, a part of the upright imaging stand 31 and the portion from the head top to below the knee of the subject H who stands in front of the upright imaging stand 31 are shown.

Figure 4:
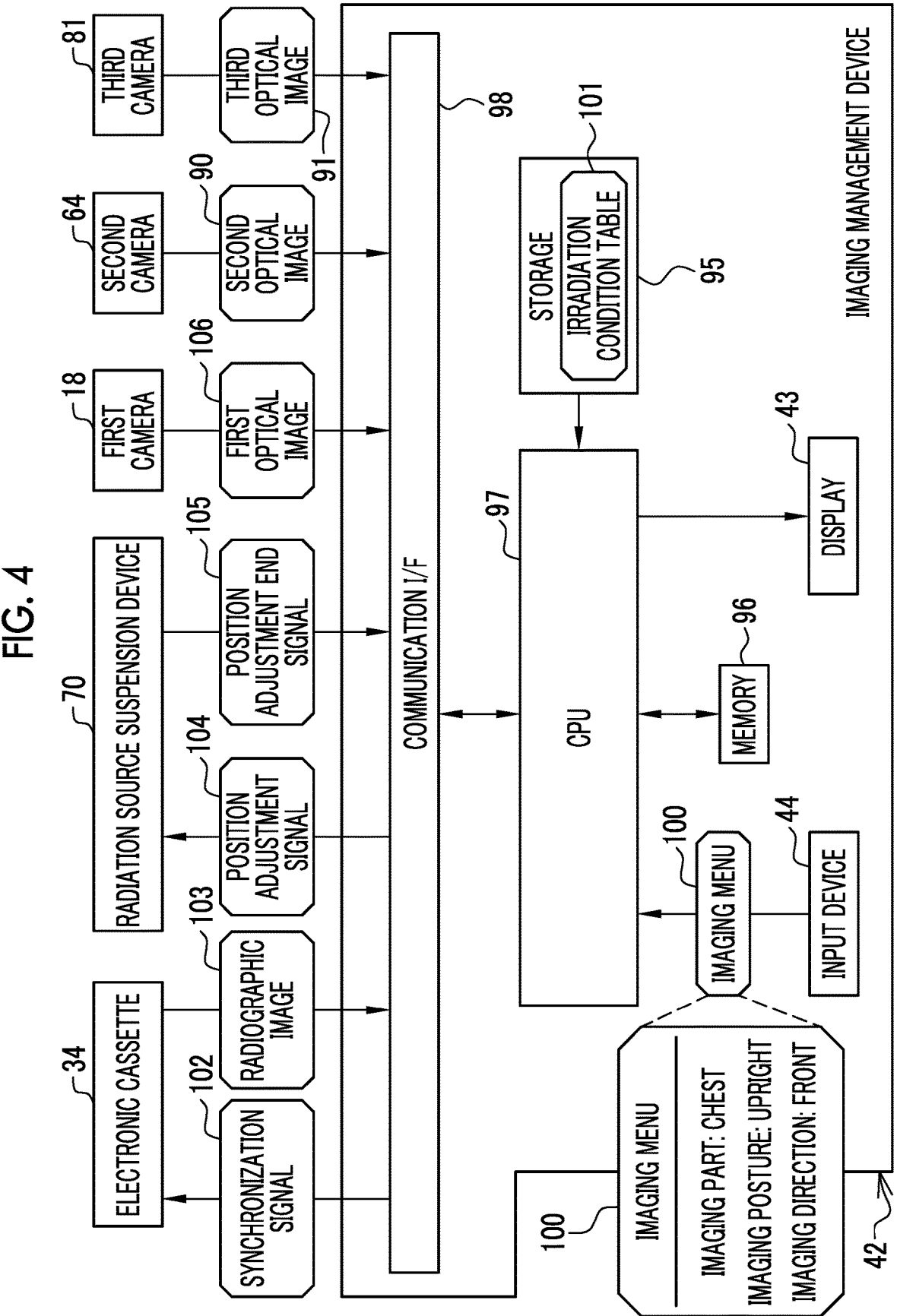
FIG. 4 is a block diagram showing the configuration of an imaging management device.

As shown in FIG. 4 as an example, the imaging management device 42 comprises a storage 95, a memory 96, a central processing unit (CPU) 97, and a communication interface (I/F) 98, in addition to the display 43 and the input device 44 described above. The display 43, the input device 44, the storage 95, the memory 96, the CPU 97, and the communication I/F 98 are connected to one another through a bus line (not shown). The storage 95, the memory 96, the CPU 97, and the bus line are an example of a "computer" according to the technique of the present disclosure.

The storage 95 is a hard disk drive that is incorporated in a computer configuring the imaging management device 42 or is connected to the computer through a cable or a network. In the storage 95, a control program, such as an operating system, various application programs, and various kinds of data associated with such programs, and the like are stored. A solid state drive may be used instead of the hard disk drive.

The memory 96 is a work memory on which the CPU 97 executes processing. The CPU 97 loads the programs stored in the storage 95 to the memory 96 to execute processing depending on the programs. With this, the CPU 97 integrally controls each unit of the computer. The CPU 97 is an example of a "processor" according to the technique of the present disclosure. The memory 96 may be incorporated in the CPU 97. The communication I/F 98 performs transmission control of various kinds of information with an external device, such as the electronic cassette 34.

The CPU 97 receives an imaging order from a radiology information system (RIS) through the communication I/F 98. In the imaging order, subject identification data (ID) for identifying the subject H, an instruction of an imaging procedure by a treatment department physician or the like who issues the imaging order, and the like are registered. The CPU 97 displays the imaging order on the display 43 depending on an operation of the operator OP by the input device 44. The operator OP confirms the contents of the imaging order through the display 43.

The CPU 97 displays a plurality of kinds of imaging menus 100 on the display 43 in a selectable form. The imaging menu 100 specifies an imaging procedure having a set of an imaging part of the subject H, an imaging posture of the subject H, and an imaging direction of the subject H, such as "chest/upright/front". The imaging part is a head, a neck, an abdomen, a waist, a shoulder, an elbow, a hand, a knee, an ankle, and the like, in addition to the chest. The imaging posture a decubitus posture, a sitting posture, and the like, in addition to the upright posture. The imaging direction is a rear surface, a lateral surface, and the like, in addition to the front surface. The operator OP operates the input device 44 to select one imaging menu 100 matching the imaging procedure designated in the imaging order among a plurality of imaging menus 100. With this, the CPU 97 receives the imaging menu 100. In this case, the operator OP selects the radiography room 10 where the radiography is performed.

The CPU 97 reads out the irradiation condition corresponding to the received imaging menu 100 from an irradiation condition table 101 stored in the storage 95. The CPU 97 displays the read-out irradiation condition on the display 43. In the irradiation condition table 101, irradiation conditions corresponding to various kinds of imaging menus 100 are registered. As described above, the irradiation condition is the tube voltage that is applied to the radiation tube 75, the tube current, and the irradiation time of the radiation R. Instead of the tube current and the irradiation time, a tube current and irradiation time product may be set as the irradiation condition.

Though not shown, the CPU 97 transmits the set irradiation condition to the radiation source control device 78 through the communication I/F 98. The CPU 97 receives the irradiation start instruction signal 79 input by the operator OP through the input device 44 and transmits the irradiation start instruction signal 79 to the radiation source control device 78. In a case where the irradiation start instruction signal 79 is received, the CPU 97 transmits a synchronization signal 102 indicating that the irradiation of the radiation R is started, to the electronic cassette 34. The CPU 97 receives the irradiation end signal 80 indicating that the irradiation of the radiation R ends, from the radiation source control device 78. In a case where the irradiation end signal 80 is received, the CPU 97 transmits a synchronization signal 102 indicating that the irradiation of the radiation R ends, to the electronic cassette 34.

In a case where the synchronization signal 102 indicating that the irradiation of the radiation R is started is received from the imaging management device 42, the electronic cassette 34 makes the detection panel start the accumulation operation. In a case where the synchronization signal 102 indicating that the irradiation of the radiation R ends is received from the imaging management device 42, the electronic cassette 34 makes the detection panel start the readout operation. A function of detecting the start and the end of the irradiation of the radiation R may be provided in the electronic cassette 34, in a case where the start of the irradiation of the radiation R is detected by the function, the detection panel may be made to start the accumulation operation, and in a case where the end of the irradiation of the radiation R is detected, the detection panel may be made to start the readout operation.

The CPU 97 receives the radiographic image 103 from the electronic cassette 34 through the communication I/F 98. The CPU 97 executes various kinds of image processing on the radiographic image 103, then, displays the radiographic image 103 on the display 43, and allows the operator OP to browse the radiographic image 103.

Though not shown, the CPU 97 transmits a position adjustment signal to the upright imaging stand 31 through the communication I/F 98. The position adjustment signal is a drive signal that is given to the motor or the like configured to move up and down the holder 33, and is a signal for setting the holder 33 and the electronic cassette 34 at the height position conforming to the imaging part or the physique of the subject H.

Before the position adjustment signal is received, the upright imaging stand 31 positions the holder 33 at a home position set in advance. In a case where the position adjustment signal is received, the upright imaging stand 31 moves up and down the holder 33 by the motor or the like, and adjusts the holder 33 and the electronic cassette 34 to the height position conforming to the imaging part or the physique of the subject H. After the position adjustment, the upright imaging stand 31 transmits a position adjustment end signal to the imaging management device 42.

The CPU 97 receives the position adjustment end signal from the upright imaging stand 31 through the communication I/F 98. In a case where the position adjustment end signal from the upright imaging stand 31 is received, the CPU 97 transmits a position adjustment signal 104 to the radiation source suspension device 70 in turn. The position adjustment signal 104 is a drive signal that is given to the motor or the like configured to expand and contract the arm 71, and is a signal for setting the radiation source 32 to the same height position as the holder 33 conforming to the imaging part or the physique of the subject H. The position adjustment signal 104 is a drive signal that is given to the motor or the like configured to move the carriage 72 along the rail 74, and is a signal for moving the radiation source 32 to the position of the SID depending on the imaging menu 100. The position adjustment signal 104 also includes a drive signal that is given to the motor or the like configured to rotate the radiation source 32, depending on the imaging menu 100.

Before the position adjustment signal 104 is received, the radiation source suspension device 70 positions the radiation source 32 at a home position set in advance. In a case where the position adjustment signal 104 is received, the radiation source suspension device 70 moves up and down the arm 71 by the motor or the like, and adjusts the arm 71 and the radiation source 32 to the same height position as the holder 33 conforming to the imaging part or the physique of the subject H. The radiation source suspension device 70 moves the carriage 72 along the rail 74 by the motor or the like, and moves the radiation source 32 to the position of the SID depending on the imaging menu 100. After the position adjustment, the radiation source suspension device 70 transmits a position adjustment end signal 105 to the imaging management device 42. The CPU 97 receives the position adjustment end signal 105 from the radiation source suspension device 70 through the communication I/F 98.

In this way, a function of automatically changing the height position of the radiation source 32 in conjunction with the change of the height position of the electronic cassette 34 is called an auto tracking function. Contrary to the auto tracking function, a reverse tracking function of automatically changing the height position of the electronic cassette 34 in conjunction with the change of the height position of the radiation source 32 may be employed.

The CPU 97 receives a first optical image 106 from a first camera 18 through the communication I/F 98. Similarly, the CPU 97 receives the second optical image 90 from the second camera 64 and the third optical image 91 from the third camera 81, through the communication I/F 98.

As shown in FIG. 5 as an example, an operation program 110 is stored in the storage 95. The operation program 110 is an application program that causes a computer to function as an imaging management device. That is, the operation program 110 is an example of an "operation program for an imaging management device" according to the technique of the present disclosure.

The guide information 111 is also stored in the storage 95. Although there are a plurality of kinds of guide information 111, such as guide information 111A (see FIG. 6) and guide information 111B (see FIG. 7), as described below, in the following description, a plurality of kinds of guide information 111A, 111B, and the like may be collectively written as guide information 111.

In a case where the operation program 110 is started, the CPU 97 functions as a first image acquisition unit 120, a second image acquisition unit 121, a third image acquisition unit 122, a first image analysis unit 123, a second image analysis unit 124, a third image analysis unit 125, a position adjustment control unit 126, a status recognition unit 127, an entrance control unit 128, a speaker control unit 129, a monitor control unit 130, and a display control unit 131 in cooperation with the memory 96 and the like.

The first image acquisition unit 120 sequentially acquires the first optical images 106 output from the first camera 18 at the predetermined frame rate. The first image acquisition unit 120 outputs the first optical image 106 to the first image analysis unit 123.

The second image acquisition unit 121 sequentially acquires the second optical images 90 output from the second camera 64 at the predetermined frame rate. The second image acquisition unit 121 outputs the second optical image 90 to the second image analysis unit 124 and the display control unit 131. Though not shown to avoid complication, the second image acquisition unit 121 outputs the second optical image 90 to the monitor control unit 130.

The third image acquisition unit 122 sequentially acquires the third optical images 91 output from the third camera 81 at the predetermined frame rate. The third image acquisition unit 122 outputs the third optical image 91 to the third image analysis unit 125 and the display control unit 131. Though not shown to avoid complication, the third image acquisition unit 122 outputs the third optical image 91 to the monitor control unit 130.

The first image analysis unit 123 performs image analysis on the first optical image 106 and detects the position of the subject H in the radiography room 10. In more detail, the first image analysis unit 123 recognizes the subject H shown in the first optical image 106 using a known image recognition technique. The first image analysis unit 123 detects a position where the recognized subject H is shown, in the first optical image 106, and where the subject H actually is, in the radiography room 10, based on a known correspondence relationship between a position in the first optical image 106 and an actual position in the radiography room 10. The first image analysis unit 123 outputs subject position information 135 indicating the position of the subject H in the radiography room 10 to the status recognition unit 127. The subject position information 135 is an example of "progress status information" according to the technique of the present disclosure.

The second image analysis unit 124 performs image analysis on the second optical image 90 and determines whether or not a status of the subject H is proper for the radiography. The second image analysis unit 124 outputs a first propriety determination result 136 that is a determination result regarding whether or not the status of the subject H is proper for the radiography, to the status recognition unit 127. Like the subject position information 135, the first propriety determination result 136 is an example of "progress status information" according to the technique of the present disclosure. The first propriety determination result 136 is an example of "imaging preparation completion information" and a "determination result" according to the technique of the present disclosure.

The third image analysis unit 125 performs image analysis on the third optical image 91 and determines whether or not the status of the subject H is proper for the radiography, from a viewpoint different from the second image analysis unit 124. The third image analysis unit 125 outputs a second propriety determination result 137 that is a determination result regarding whether or not the status of the subject H is proper for the radiography, to the status recognition unit 127. Like the subject position information 135 and the like, the second propriety determination result 137 is an example of "progress status information" according to the technique of the present disclosure. The second propriety determination result 137 is an example of "imaging preparation completion information" and a "determination result" according to the technique of the present disclosure along with the first propriety determination result 136.

The third image analysis unit 125 performs image analysis on the third optical image 91 to estimate a body height of the subject H. The third image analysis unit 125 outputs a body height estimation result 138 of the subject H to the position adjustment control unit 126. A scale representing a body height may be provided in the field of view FOV2 of the third optical image 91, such as the support 61 of the upright imaging stand 31 or a wall surface of the radiography room 10 in the vicinity of the upright imaging stand 31, and image recognition may be performed on divisions of the scale shown in the third optical image 91, thereby estimated the body height of the subject H.

The position adjustment control unit 126 transmits the position adjustment signal 104 depending on the body height estimation result 138 from the third image analysis unit 125, to the radiation source suspension device 70. Though not shown, the position adjustment control unit 126 also transmits the position adjustment signal depending on the body height estimation result 138 from the third image analysis unit 125, to the upright imaging stand 31.

The status recognition unit 127 acquires the subject position information 135 from the first image analysis unit 123, the first propriety determination result 136 from the second image analysis unit 124, and the second propriety determination result 137 from the third image analysis unit 125. In addition, the status recognition unit 127 acquires the position adjustment end signal 105 from the radiation source suspension device 70. The status recognition unit 127 acquires an on signal 139 and an off signal 140 (in FIG. 5, written as an on/off signal) from the first human sensor 23 and the second human sensor 24 (in FIG. 5, collectively referred to as a human sensor). Like the subject position information 135 and the like, the position adjustment end signal 105, the on signal 139, and the off signal 140 are also an example of "progress status information" according to the technique of the present disclosure. Though not shown, the status recognition unit 127 also acquires the irradiation start instruction signal 79 that is transmitted to the radiation source control device 78 and the irradiation end signal 80 from the radiation source control device 78. The irradiation start instruction signal 79 and the irradiation end signal 80 are also an example of "progress status information" according to the technique of the present disclosure.

The status recognition unit 127 recognizes the progress status of the radiography from the irradiation start instruction signal 79, the irradiation end signal 80, the position adjustment end signal 105, the subject position information 135, the first propriety determination result 136, the second propriety determination result 137, and the on signal 139 and the off signal 140. The status recognition unit 127 outputs a signal representing the recognized progress status to the entrance control unit 128. The status recognition unit 127 reads out the guide information 111 depending on the recognized progress status, from the storage 95. The status recognition unit 127 outputs the read-out guide information 111 to the speaker control unit 129 and the monitor control unit 130.

In a case where the first propriety determination result 136 and the second propriety determination result 137 having the content that the status of the subject H is proper for the radiography are acquired, the status recognition unit 127 outputs a signal indicating that the timing of the radiography is reached, to the display control unit 131.

The entrance control unit 128 outputs an unlocking signal 141 or a locking signal 142 (in FIG. 5, written as an unlocking/locking signal) to the electric lock 16 to control unlocking or locking of the electric lock 16. The entrance control unit 128 performs control for shifting an unlocking timing of the electric lock 16 between the radiography rooms 10A and 10B to shift the entrance timing of the subjects H into the radiography rooms 10A and 10B, thereby shifting the timing of the radiography in the radiography rooms 10A and 10B (see FIG. 26).

The speaker control unit 129 controls the operation of the speaker 38. The speaker control unit 129 performs control for outputting the guide voice 152 that is a voice announcement of the guide information 111, from the speaker 38. The speaker control unit 129 performs control for shifting the output timing of the guide voice 152 to change a progress speed of the radiography, thereby shifting the timing of the radiography in the radiography rooms 10A and 10B (see FIG. 27).

The monitor control unit 130 controls the operations of the imaging room monitor 37 and the waiting room monitor

51 (in FIG. 5, collectively written as a monitor). The monitor control unit 130 performs control for generating a guide screen 155 (see FIG. 12) based on the guide information 111 and displaying the generated guide screen 155 on the imaging room monitor 37. The monitor control unit 130 performs control for generating an entrance guidance screen 150 (see FIG. 6 or the like) based on the guide information 111 and displaying the generated entrance guidance screen 150 on the waiting room monitor 51. The monitor control unit 130 performs control for outputting the guide voice 152 that is a voice announcement of the guide information 111, from the speaker of the waiting room monitor 51. Like the speaker control unit 129, the monitor control unit 130 performs control for shifting the display timing of the guide screen 155 or the entrance guidance screen 150 and the output timing of the guide voice 152 to change the progress speed of the radiography, thereby shifting the timing of the radiography in the radiography rooms 10A and 10B.

The display control unit 131 controls the operation of the display 43. The display control unit 131 performs control for generating an information display screen 175 (see FIG. 18) regarding the radiography room 10 and displaying the generated information display screen 175 on the display 43. Though not shown, a reception unit that receives the imaging order from the RIS, an image processing unit that executes various kinds of image processing on the radiographic image 103, a setting unit that sets the irradiation condition in the radiation source control device 78, and the like are constructed in the CPU 97, in addition to the respective processing units 120 to 131.

In the following description, a series of flow in a case where chest/upright/front imaging is successively performed on a subject H of a reception number 001 and a subject H of a reception number 002 in the first radiography room 10A will be described. In a case of distinguishing between the subject H of the reception number 001 and the subject H of the reception number 002, the subject H of the reception number 001 is written as a subject H1, and the subject H of the reception number 002 is written as a subject H2.

Figure 6:
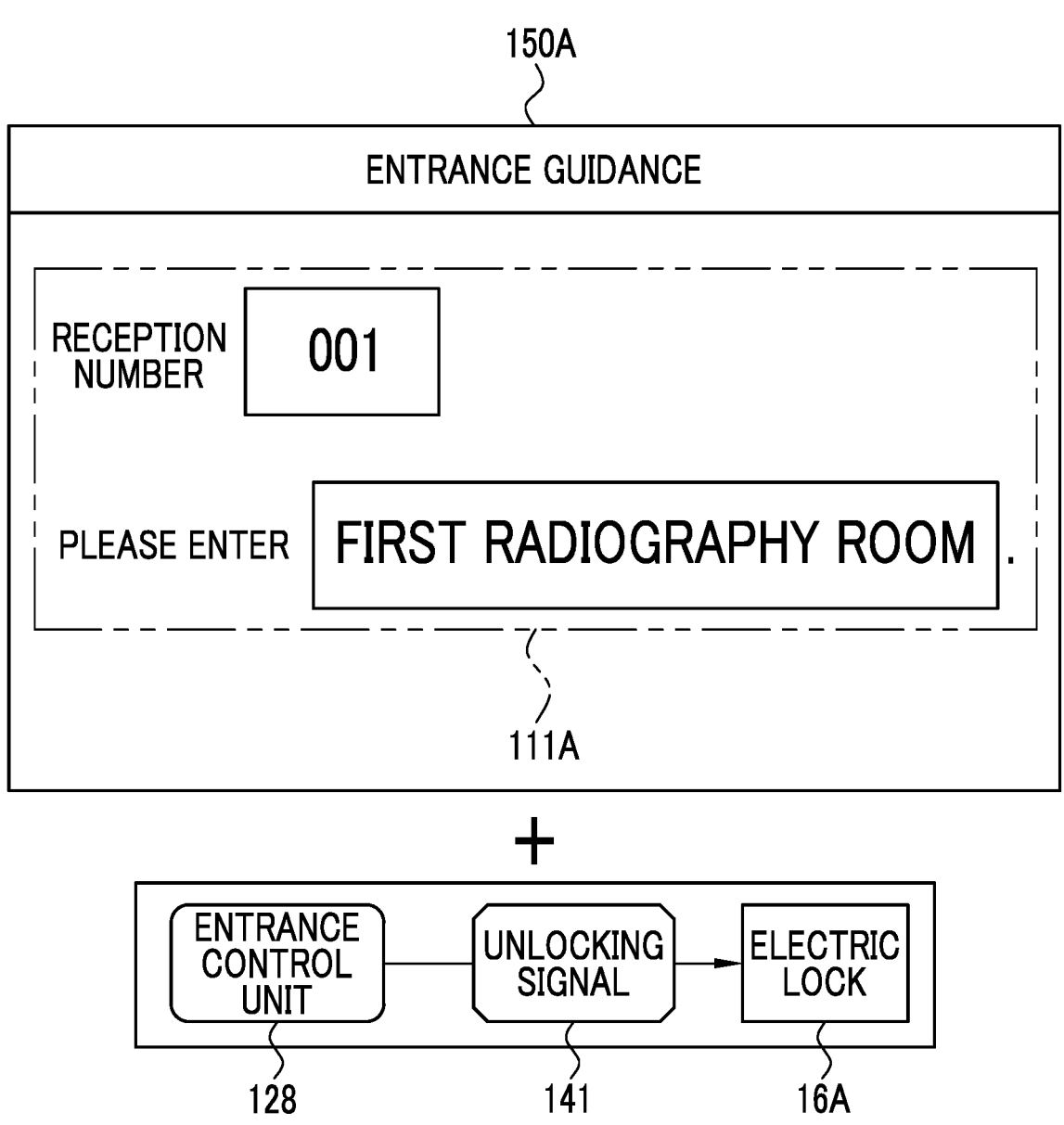
FIG. 6 is a diagram showing an entrance guidance screen for a subject of a reception number 001 and processing of an entrance control unit.

First, as shown in FIG. 6 as an example, the monitor control unit 130 performs control for displaying an entrance guidance screen 150A on the waiting room monitor 51A. The guide information 111A is displayed on the entrance guidance screen 150A. The guide information 111A has the content of prompting the subject H1 to enter the radiography room 10A (in FIG. 6, written as a first radiography room). The monitor control unit 130 performs control for outputting guide voice (not shown) having the same contents as the guide information 111A from the speaker of the waiting room monitor 51A.

At the same time with the display control of the entrance guidance screen 150A by the monitor control unit 130, the entrance control unit 128 outputs the unlocking signal 141 to the electric lock 16A. With this, the electric lock 16A is unlocked, and the subject H1 can open the first door 15A and enter the radiography room 10A.

The subject H1 opens the first door 15A and enters the radiography room 10A following the guide information 111A on the entrance guidance screen 150A and the guide voice.

Figure 7:
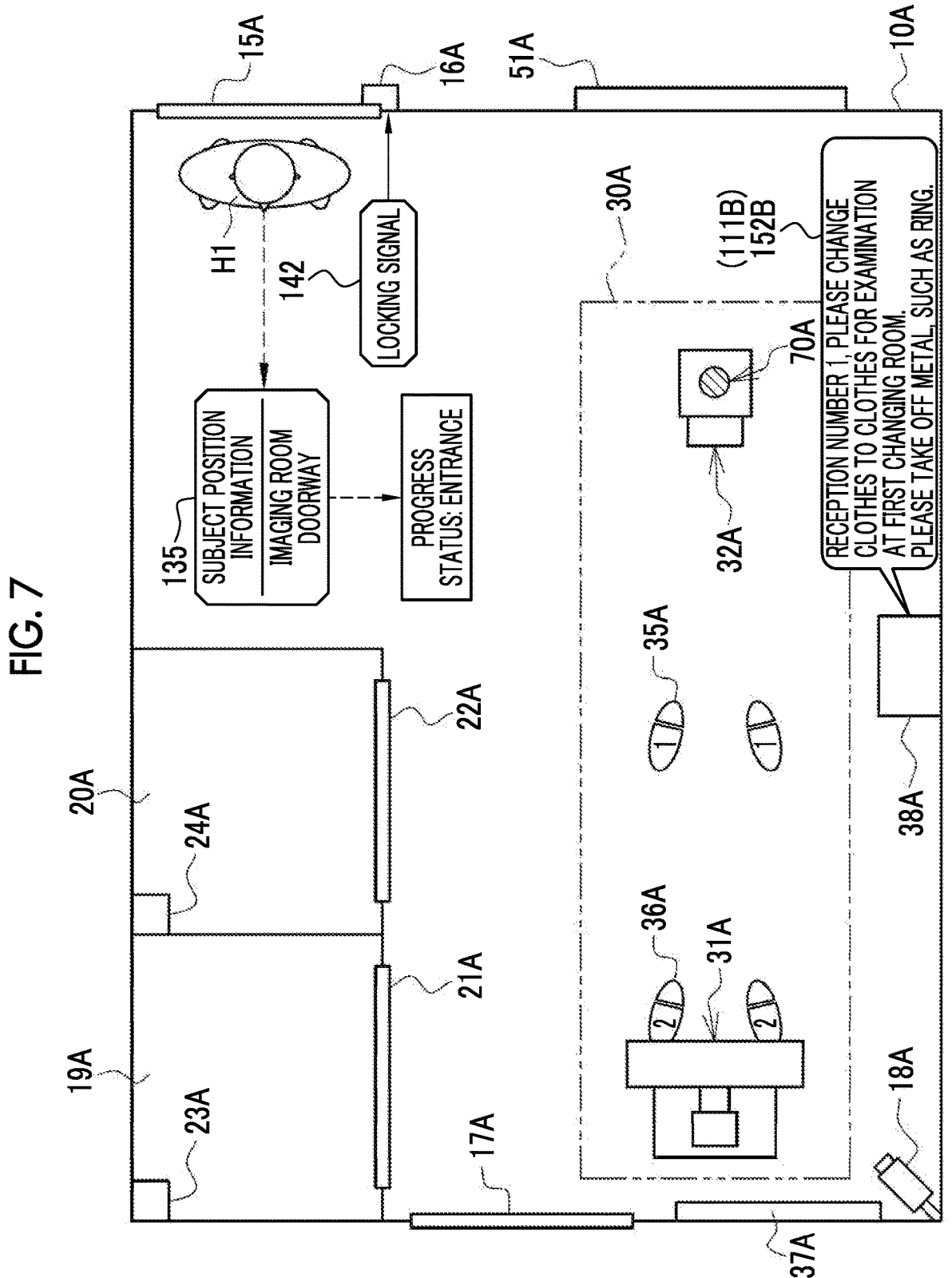
FIG. 7 is a diagram showing a case where a progress status of radiography is "entrance"

FIG. 7 shows a case where the subject H1 opens the first door 15A and enters the radiography room 10A, and the subject H1 stands in the vicinity of a doorway of the radiography room 10A. In this case, the subject position information 135 has the content of "imaging room doorway". With the subject position information 135, the status recognition unit 127 recognizes that the progress status of the radiography in the radiography room 10A is "entrance". The status recognition unit 127 reads out guide information 111B from the storage 95 and outputs the guide information 111B to the speaker control unit 129. The speaker control unit 129 performs control for outputting guide voice 152B that is a voice announcement of the guide information 111B, from the speaker 38A. The guide voice 152B has the content of prompting the subject H1 to change clothes to clothes for examination at the first changing room 19A and to take off metal.

The status recognition unit 127 outputs a signal indicating that the progress status is recognized to be "entrance", to the entrance control unit 128. The entrance control unit 128 receives the signal from the status recognition unit 127 indicating that the progress status is recognized to be "entrance", and outputs the locking signal 142 to the electric lock 16A. With this, the electric lock 16A is locked, and a person other than the subject H1 cannot enter the radiography room 10A.

The subject H1 opens the third door 21A, enters the first changing room 19A, and changes clothes to the clothes for examination at the first changing room 19A following the guide voice 152B. The subject H1 takes off metal, such as a ring or a wristwatch, in some cases.

Figure 8:
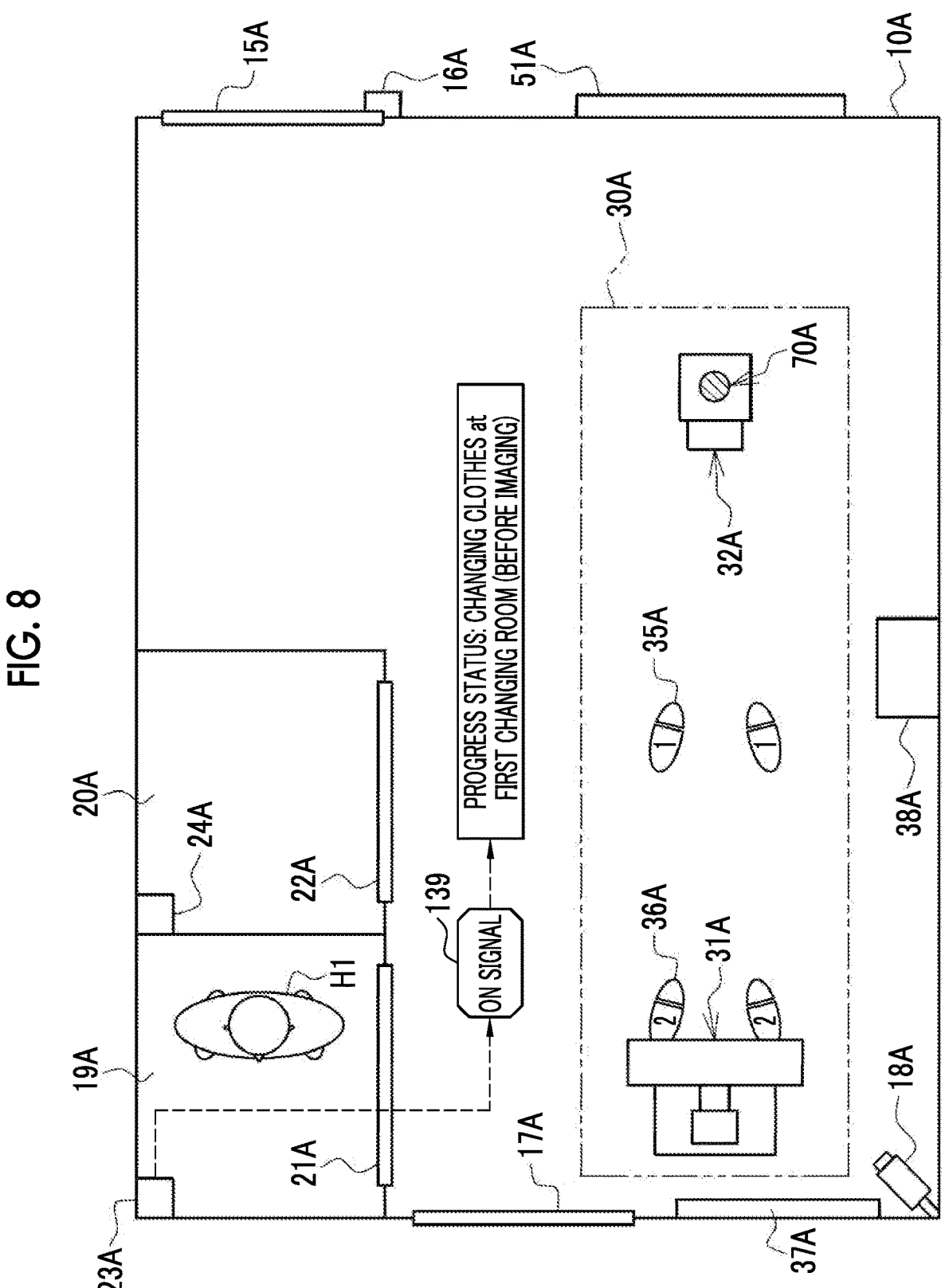
FIG. 8 is a diagram showing a case where the progress status of the radiography is "changing clothes (before imaging)"

As shown in FIG. 8 as an example, in a case where the subject H1 enters the first changing room 19A, the first human sensor 23A detects the subject H1 and outputs the on signal 139. With the on signal 139, the status recognition unit 127 recognizes that the progress status of the radiography in the radiography room 10A is "changing clothes at first changing room (before imaging)".

After changing clothes to the clothes for examination ends, the subject H1 opens the third door 21A and returns from the first changing room 19A to the radiography room 10A again.

Figure 9:
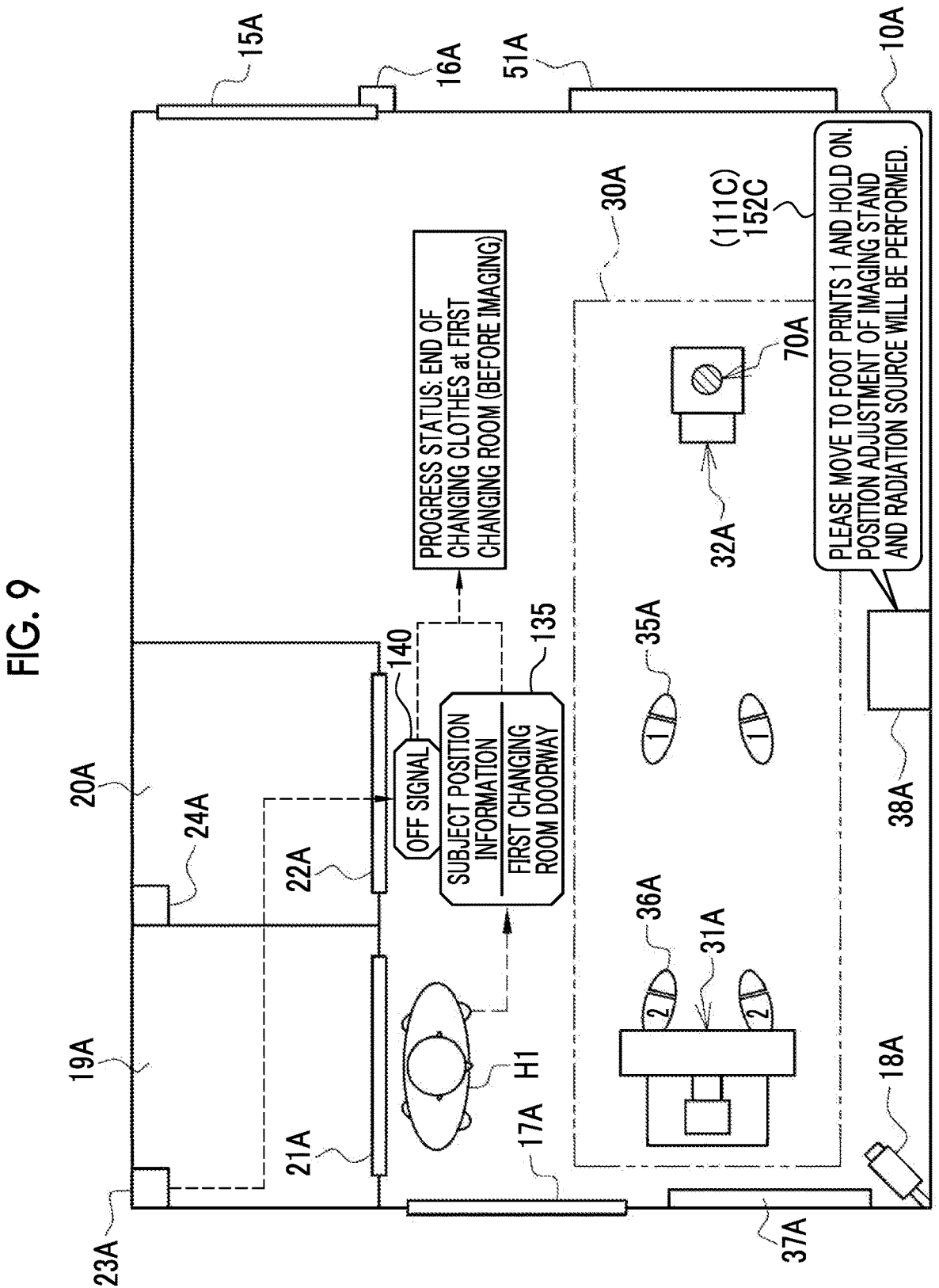
FIG. 9 is a diagram showing a case where the progress status of the radiography is "end of changing clothes (after imaging)"

FIG. 9 shows a case where changing clothes to the clothes for examination ends, the subject H1 returns from the first changing room 19A to the radiography room 10A, and the subject H1 stands in the vicinity of a doorway of the first changing room 19A. In this case, the subject position information 135 has the content of "first changing room doorway". In this case, since the subject H1 is not detected, the first human sensor 23A outputs the off signal 140. With the subject position information 135 and the off signal 140, the status recognition unit 127 recognizes that the progress status of the radiography in the radiography room 10A is "end of changing clothes at first changing room (before imaging)". The status recognition unit 127 reads out guide information 111C from the storage 95 and outputs the guide information 111C to the speaker control unit 129. The speaker control unit 129 performs control for outputting guide voice 152C that is a voice announcement of the guide information 111C, from the speaker 38A. The guide voice 152C has the content of prompting the subject H1 to move to a waiting position where the first footprints 35A are present and to wait, and of notifying the subject H1 that the position adjustment of the upright imaging stand 31A (holder 33A) and the radiation source 32A will be performed.

The subject H1 moves to the waiting position and stands while placing both feet on the first footprints 35A following the guide voice 152C.

FIG. 10 shows a case where the subject H1 is standing at the waiting position. In this case, the subject position information 135 has the content of "waiting position". With the subject position information 135, the status recognition unit 127 recognizes that the progress status of the radiography in the radiography room 10A is "waiting". The status recognition unit 127 reads out guide information 111D from the storage 95 and outputs the guide information 111D to the speaker control unit 129. The speaker control unit 129 performs control for outputting guide voice 152D that is a voice announcement of the guide information 111D, from the speaker 38A. The guide voice 152D has the content of notifying the subject H1 that the position adjustment of the upright imaging stand 31A (holder 33A) and the radiation source 32A are in progress, and of instructing the subject H1 not to move at the waiting position.

In a case where the progress status is recognized to be "waiting", the status recognition unit 127 transmits an operation start instruction signal to the third camera 81. With this, the third camera 81 starts to operate and outputs the third optical images 91. The third optical images 91 are acquired by the third image acquisition unit 122 and are output from the third image acquisition unit 122 to the third image analysis unit 125. Then, the body height of the subject H1 is estimated in the third image analysis unit 125, and the body height estimation result 138 is output from the third image analysis unit 125 to the position adjustment control unit 126. The position adjustment signal depending on the body height estimation result 138 is transmitted from the position adjustment control unit 126 to the upright imaging stand 31A. With this, the holder 33 (electronic cassette 34) is moved to the height position conforming to the imaging part or the physique of the subject H1. Thereafter, the position adjustment signal 104 depending on the body height estimation result 138 is transmitted from the position adjustment control unit 126 to the radiation source suspension device 70A. With this, the radiation source 32 is moved to the same height position as the holder 33 conforming to the imaging part or the physique of the subject H1. The radiation source 32 is moved to the position of the SID depending on the imaging menu 100.

Figure 11:
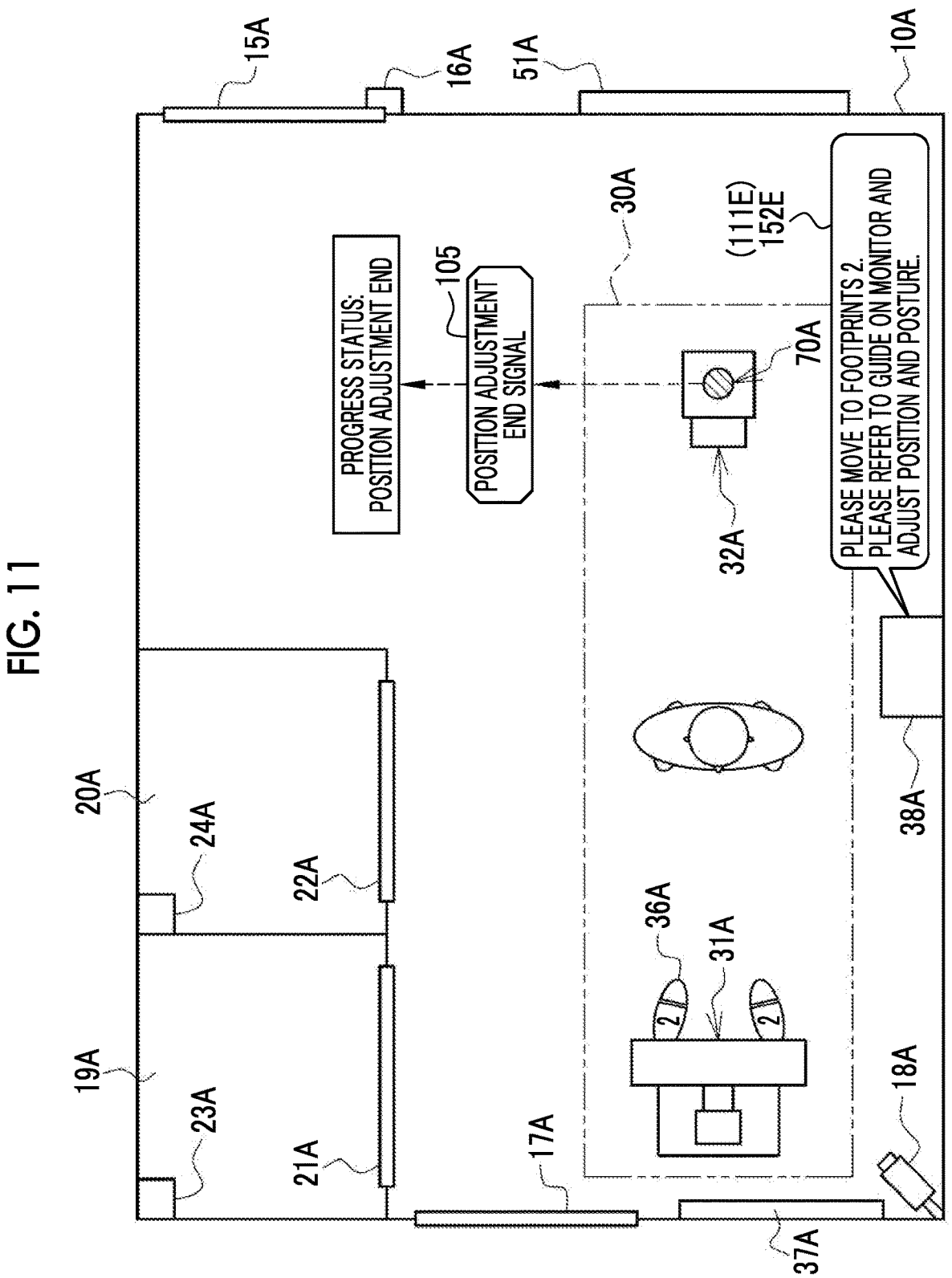
FIG. 11 is a diagram showing a case where the progress status of the radiography is "position adjustment end"

FIG. 11 shows a case where the position adjustment of the radiation source 32 by the position adjustment control unit 126 ends, and the position adjustment end signal 105 is transmitted from the radiation source suspension device 70A to the imaging management device 42. With the position adjustment end signal 105, the status recognition unit 127 recognizes that the progress status of the radiography in the radiography room 10A is "position adjustment end". The status recognition unit 127 reads out guide information 111E from the storage 95 and outputs the guide information 111E to the speaker control unit 129. The speaker control unit 129 performs control for outputting guide voice 152E that is a voice announcement of the guide information 111E, from the speaker 38A. The guide voice 152E has the content of prompting the subject H1 to move to an imaging position where the second footprints 36A are present, and to adjust his/her position and posture with reference to the guide screen 155 of the imaging room monitor 37A.

The subject H1 moves to the imaging position and stands while placing both feet on the second footprints 36A following the guide voice 152E.

In a case where the progress status is recognized to be "position adjustment end", the status recognition unit 127 transmits an operation start instruction signal to the second camera 64. With this, the second camera 64 starts to operate and outputs the second optical images 90. The second optical images 90 are acquired by the second image acquisition unit 121 and are output from the second image acquisition unit 121 to the second image analysis unit 124.

In a case where the progress status is recognized to be "position adjustment end", the status recognition unit 127 reads guide information 111F_1 and 111F_2 (see FIG. 12) from the storage 95 and outputs the guide information 111F_1 and 111F_2 to the monitor control unit 130.

Figure 12:
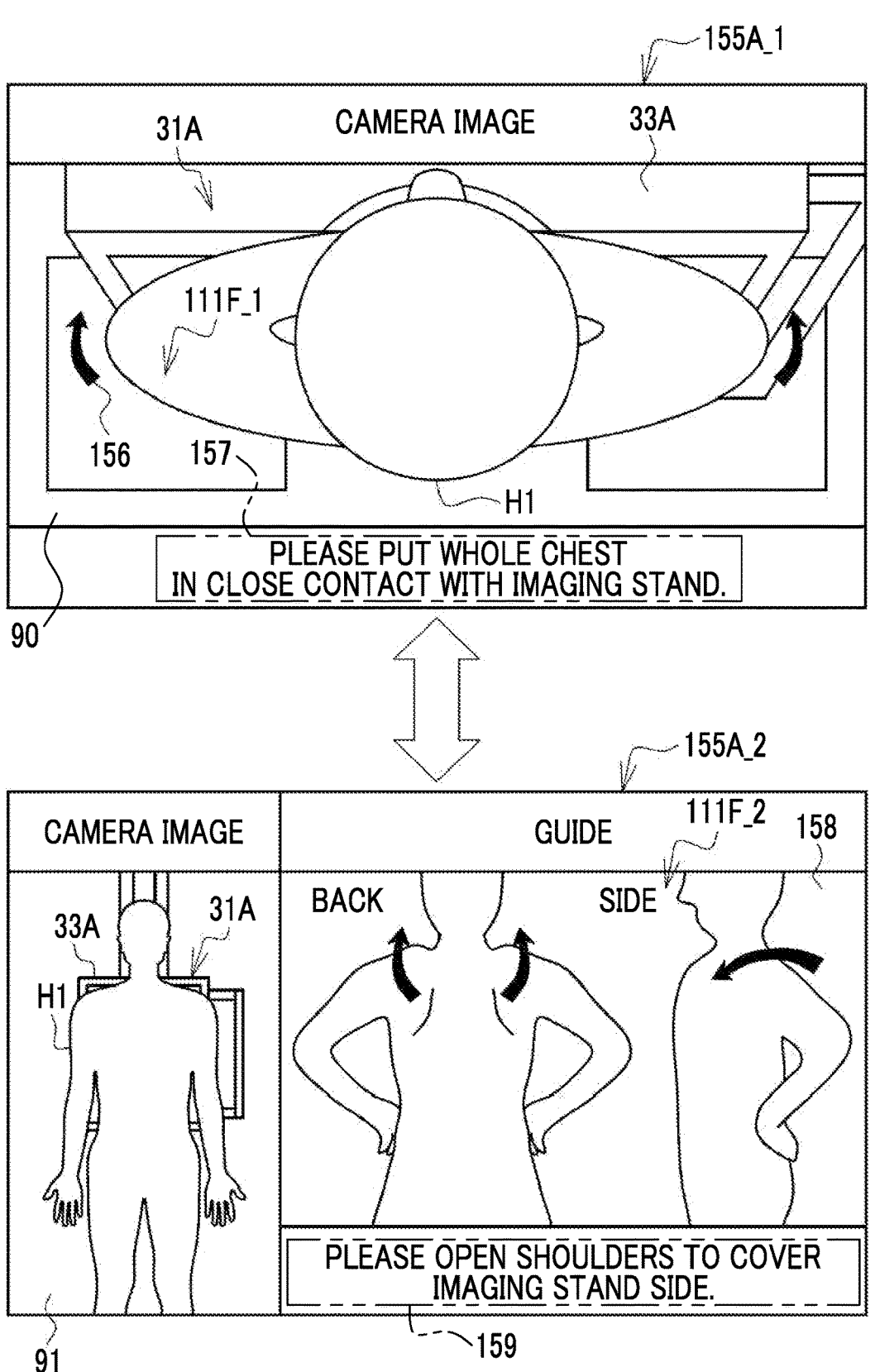
FIG. 12 is a diagram showing a guide screen that is displayed on an imaging room monitor.

As shown in FIG. 12 as an example, the monitor control unit 130 performs control for alternately switching and displaying guide screens 155A_1 and 155A_2 on the imaging room monitor 37A at a predetermined display interval, for example, at an interval of five seconds. The second optical images 90 and the guide information 111F_1 are displayed on the guide screen 155A_1. The monitor control unit 130 sequentially updates and displays the second optical images 90 that are output from the second camera 64 at the predetermined frame rate, on the guide screen 155A_1. That is, the second optical images 90 that are displayed on the guide screen 155A_1 are a live view image (video).

The guide information 111F_1 includes arrows 156 and a message 157. The arrows 156 are displayed in portions of the second optical image 90 outside both shoulders of the subject H1 in a superimposed manner. A direction of the arrows 156 is a direction of prompting the subject H1 to move both shoulders to cover the upright imaging stand 31A. The message 157 has the content of prompting the subject H1 to put the whole chest in close contact with the upright imaging stand 31A (holder 33A).

The third optical image 91 and the guide information 111F_2 are displayed on the guide screen 155A_2. Like a case of the guide screen 155A_1, the monitor control unit 130 sequentially updates and displays the third optical images 91 that are sequentially output from the third camera 81 at the predetermined frame rate, on the guide screen 155A_2. That is, the third optical images 91 that are displayed on the guide screen 155A_2 is a live view image (video).

The guide information 111F_2 includes an illustration 158 and a message 159. The illustration 158 and the message 159 have the content of prompting the subject H1 to open shoulder bones to cover the upright imaging stand 31A (holder 33A), and to put the whole chest in close contact with the upright imaging stand 31A (holder 33A). The illustration 158 may be displayed on the third optical image 91 in a superimposed manner.

The subject H1 adjusts the position and the posture with reference to the second optical image 90 and the third optical image 91 of the guide screens 155A_1 and 155A_2 and the guide information 111F_1 and 111F_2.

Figure 13:
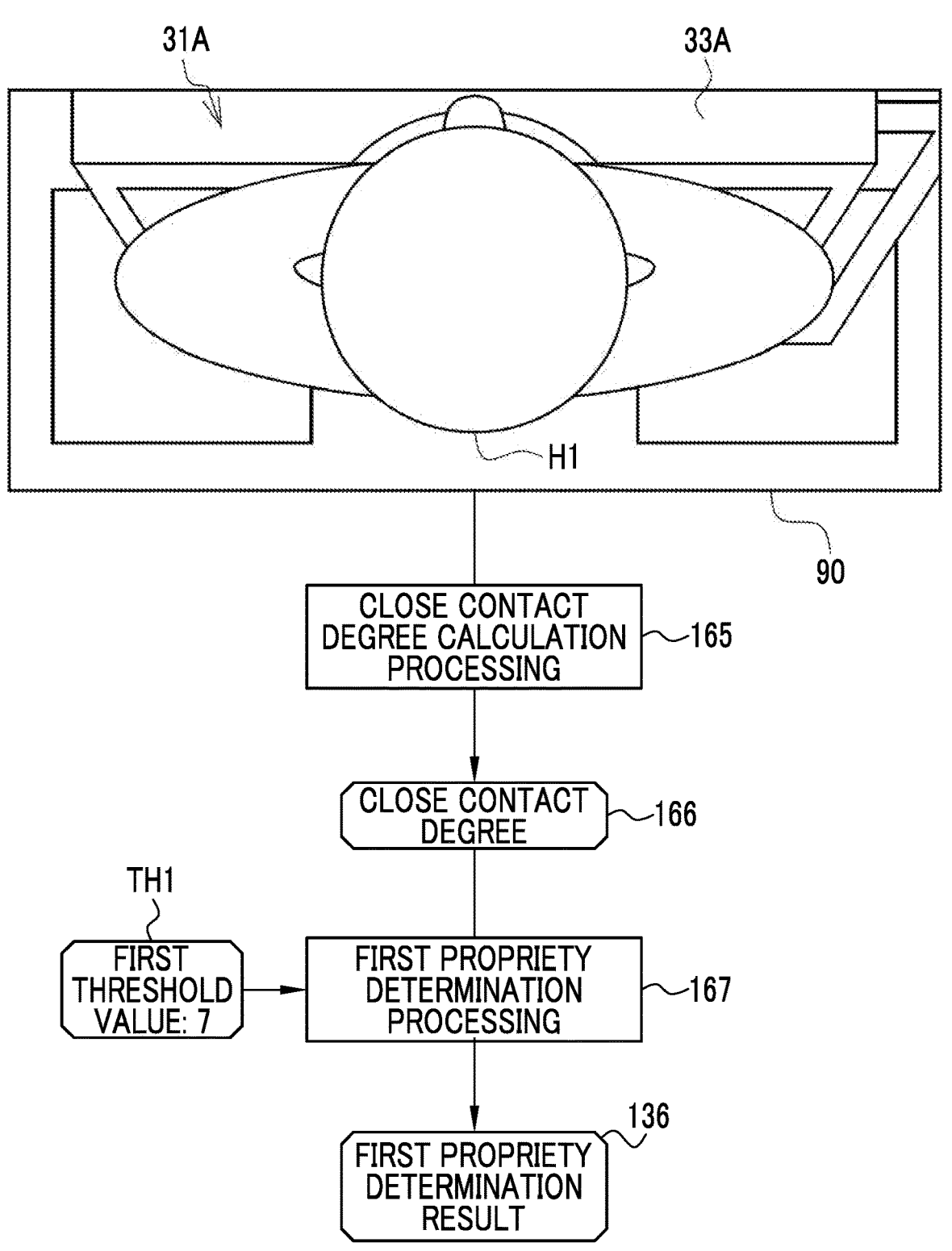
FIG. 13 is a diagram showing processing of a second image analysis unit.

As shown in FIG. 13 as an example, the second image analysis unit 124 executes close contact degree calculation processing 165 on the second optical image 90. The close contact degree calculation processing 165 is executed, for example, as follows. That is, the holder 33A and the shoulders of the subject H1 are extracted from the second optical image 90 by image recognition. Then, a close contact degree 166 indicating a degree of close contact of the subject H1 with the holder 33A is calculated from a positional relationship between the holder 33A and the shoulders of the subject H1 extracted as above. The close contact degree 166 is a ten-stage numerical value of 1 to 10, and as the numerical value is higher, this indicates the degree of close contact of the subject H1 with the holder 33A is higher.

Next, the second image analysis unit 124 executes first propriety determination processing 167. The first propriety determination processing 167 is processing of comparing the close contact degree 166 calculated in the close contact degree calculation processing 165 with a first threshold value TH1 set in advance in magnitude, determining whether or not the degree of close contact of the subject H1 with the holder 33A is proper for the radiography, and outputting the first propriety determination result 136. The degree of close contact of the subject H1 with the holder 33A is an example of a "status of a subject" according to the technique of the present disclosure.

The first threshold value TH1 is set to, for example, a numerical value depending on a condition that the radiographic image 103 having image quality to be empirically recommended for diagnosis is not obtained in a case where the close contact degree less than the numerical value. In FIG. 13, seven is set as the first threshold value TH1.

Figures 14A, 14B:
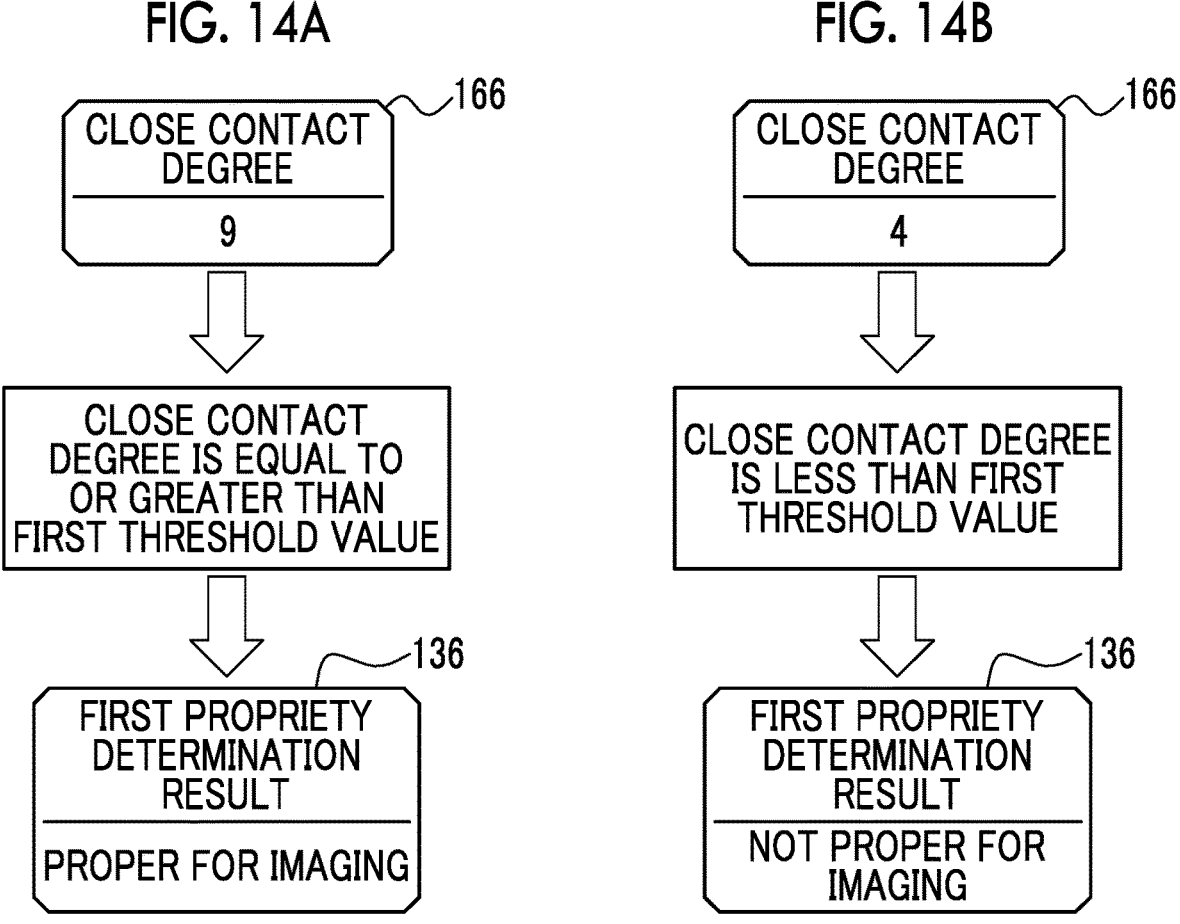
FIGS. 14A and 14B are diagrams showing the processing of the second image analysis unit.

As shown in FIGS. 14A and 14B as an example, the second image analysis unit 124 determines whether or not the degree of close contact of the subject H1 with the holder 33A is proper for the radiography, depending on whether or not the close contact degree 166 is equal to or greater than the first threshold value TH1. As shown in FIG. 14A, in a case where the close contact degree 166 is equal to or greater than the first threshold value TH1, the second image analysis unit 124 determines that the degree of close contact of the subject H1 with the holder 33A is proper for the radiography, and outputs the first propriety determination result 136 indicating to be proper for the radiography. On the other hand, as shown in FIG. 14B, in a case where the close contact degree 166 is less than the first threshold value TH1, the second image analysis unit 124 determines that the degree of close contact of the subject H1 with the holder 33A is not proper (improper) for the radiography, and outputs the first propriety determination result 136 indicating to be not proper for the radiography.

The first propriety determination result 136 indicating that the degree of close contact of the subject H1 with the holder 33A is not proper for the radiography is notified to the operator OP through the information display screen 175 displayed on the display 43. In this case, the operator OP sends a voice announcement to the speaker 38A through the microphone 45 and instructs the subject H1 to be in closer contact with the holder 33A.

Figure 15:
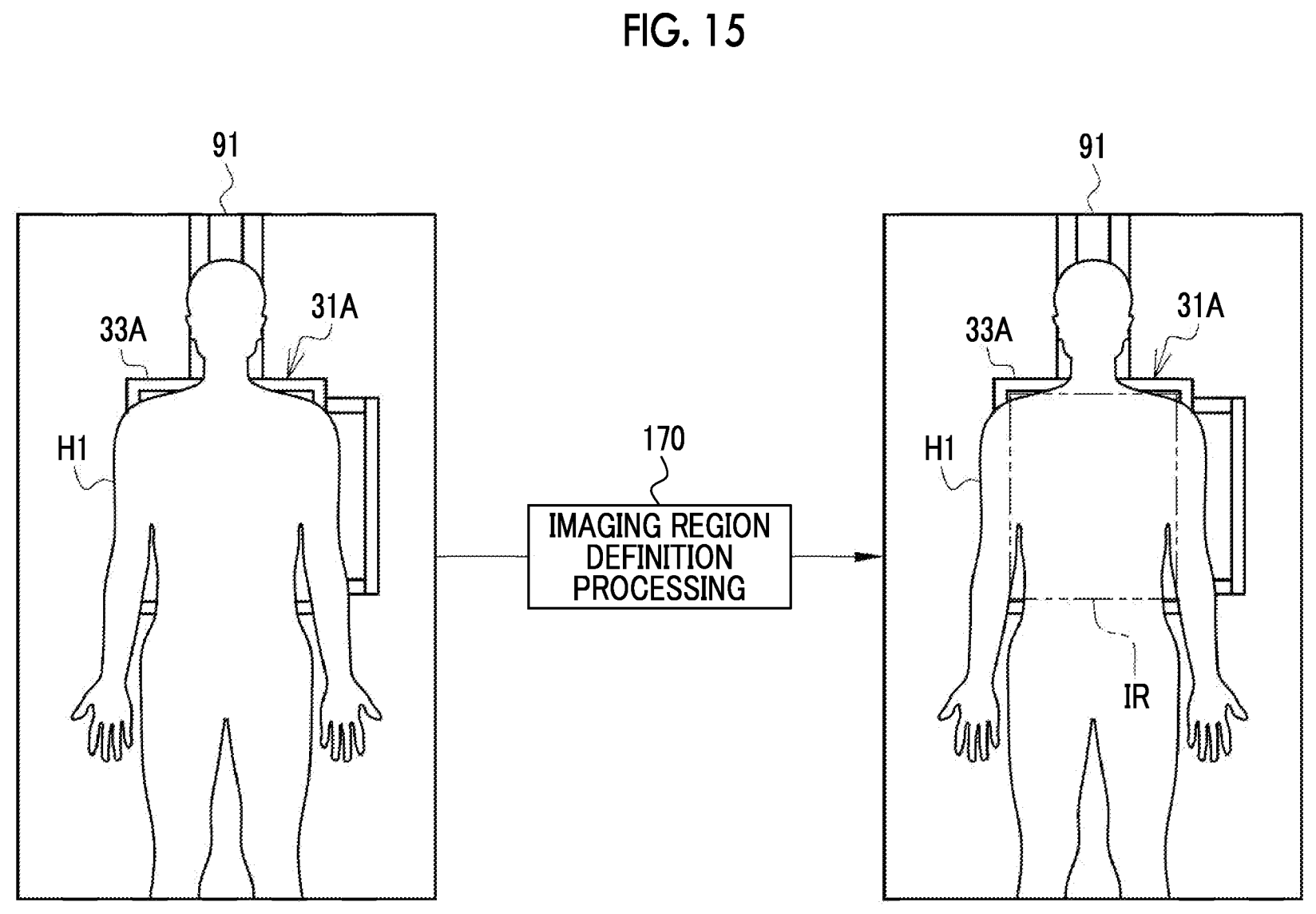

As shown in FIG. 15 as an example, the third image analysis unit 125 executes imaging region definition processing 170 on the third optical image 91. The imaging region definition processing 170 is processing of defining an imaging region IR to be imaged in the radiographic image 103, in the third optical image 91. The imaging region IR is a region set in advance depending on the imaging menu 100 and is a region of a human body to fall within the radiographic image 103 with the imaging menu 100.

The imaging region definition processing 170 is executed, for example, as follows. First, feature points of the subject H1 shown in the third optical image 91 are extracted using a known image recognition technique or a machine learning model. The feature points in this case are right and left shoulder joint points and right and left hip joint points. The shoulder joint points are connection points of shoulder bones and upper arm bones. The hip joint points are connection points of coxal bones and a thighbone.

Subsequently, a spot of interest related to the imaging region IR is extracted based on the feature points. The spot of interest in this case is a center point (hereinafter, written as a prominent vertebra point) of a prominent vertebra. The prominent vertebra point is, for example, a point of a coefficient multiple of a length of a line that connects a middle point of a line connecting the right and left shoulder joint points and a middle point of a line connecting the right and left hip joint points. The coefficient is statistically obtained from data of an unspecified large number of subjects H in the past.

Finally, the imaging region IR is defined based on the spot of interest. Here, for example, a rectangular region that has the prominent vertebra point as the center of an upper side and has a size depending on the SID and the FOV2 of the third camera 81 is defined as the imaging region IR.

The third image analysis unit 125 defines a detection region DR (see FIG. 16) for the radiation R of the electronic cassette 34A in the third optical image 91 based on the SID and the FOV2 of the third camera 81. The detection region DR is a region of the substantially whole surface of the detection panel of the electronic cassette 34A. Thereafter, the third image analysis unit 125 executes second propriety determination processing. The second propriety determination processing is processing of determining whether or not the position and the posture of the subject H1 with respect to the holder 33A (electronic cassette 34A) are proper for the radiography, and outputting the second propriety determination result 137. The position and the posture of the subject H1 with respect to the holder 33A (electronic cassette 34A) are an example of a "status of a subject" according to the technique of the present disclosure.

As shown in FIGS. 16A and 16B as an example, the third image analysis unit 125 determines whether or not the position and the posture of the subject H1 with respect to the holder 33A are proper for the radiography, depending on whether or not the imaging region IR falls within the detection region DR. As shown in FIG. 16A, in a case where the imaging region IR falls within the detection region DR, the third image analysis unit 125 determines that the position and the posture of the subject H1 with respect to the holder 33A are proper for the radiography, and outputs the second propriety determination result 137 indicating to be proper for the radiography. On the other hand, as shown in FIG. 16B, in a case where the imaging region IR does not fall within the detection region DR, the third image analysis unit 125 determines that the position and the posture of the subject H1 with respect to the holder 33A are not proper (improper) for the radiography, and outputs the second propriety determination result 137 indicating to be not proper for the radiography.

The second propriety determination result 137 indicating that the position and the posture of the subject H1 with respect to the holder 33A are not proper for the radiography is notified to the operator OP through the information display screen 175 displayed on the display 43. In this case, the operator OP sends a voice announcement to the speaker 38A through the microphone 45 and instructs the subject H1 to adjust the position and the posture with respect to the holder 33A to make the imaging region IR fall within the detection region DR.

Figure 17:
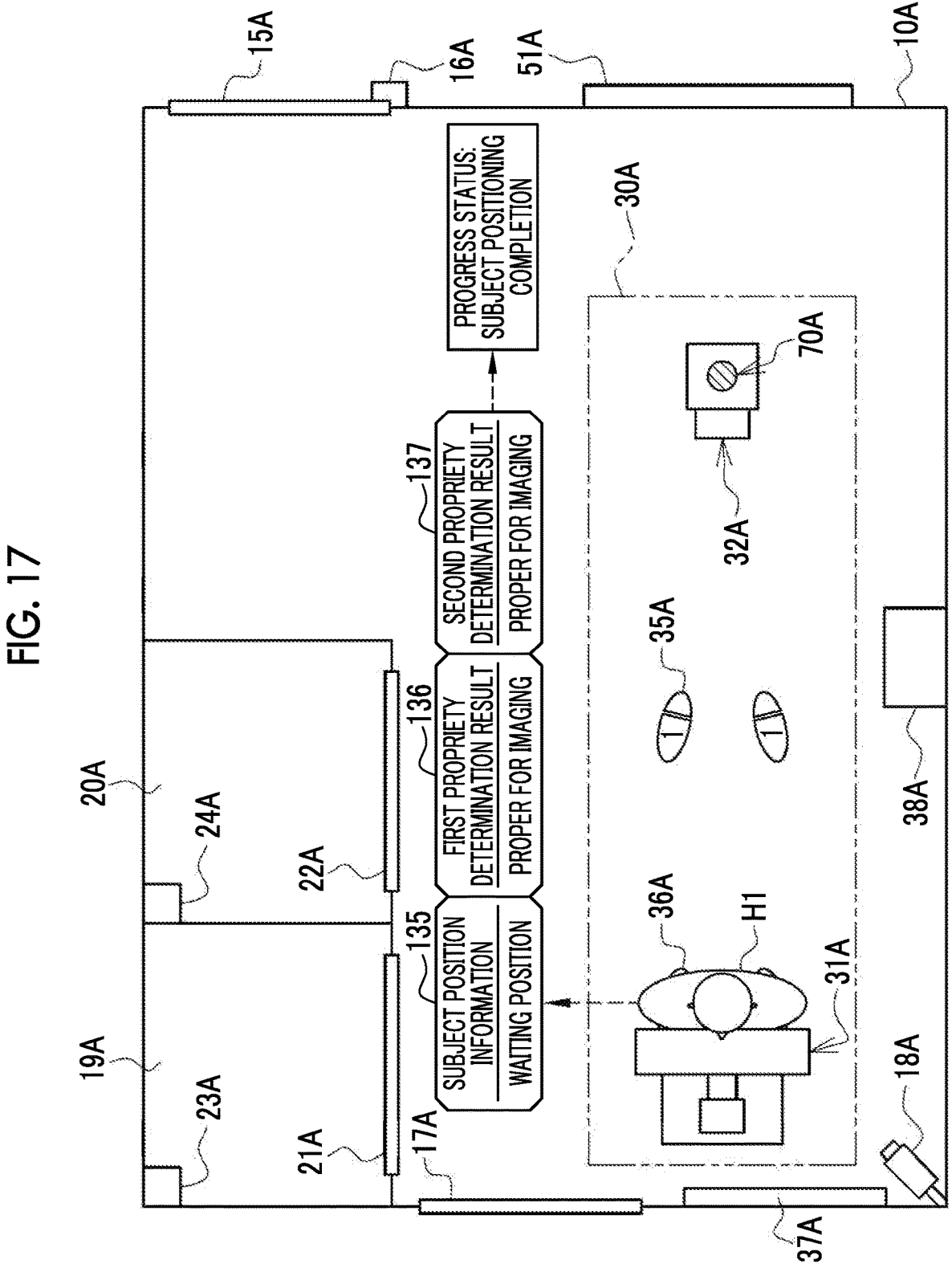
FIG. 17 is a diagram showing a case where the progress status of the radiography is "subject positioning completion"

FIG. 17 shows a case where the subject H1 is standing at the imaging position. In this case, the subject position information 135 has the content of "imaging position". FIG. 17 shows a case where the degree of close contact of the subject H1 with the holder 33A is proper for the radiography, and the first propriety determination result 136 indicating to be proper for the radiography is output from the second image analysis unit 124. FIG. 17 shows a case where the position and the posture of the subject H1 with respect to the holder 33A are proper for the radiography, and the second propriety determination result 137 indicating to be proper for the radiography is output from the third image analysis unit 125.

With the subject position information 135, the first propriety determination result 136, and the second propriety determination result 137, the status recognition unit 127 recognizes that the progress status of the radiography in the radiography room 10A is "subject positioning completion".

The status recognition unit 127 outputs a signal indicating that the progress status is recognized to be "subject positioning completion, to the display control unit 131" as a signal indicating that the timing of the radiography is reached. The display control unit 131 receives the signal from the status recognition unit 127 indicating that the timing of the radiography is reached, and performs control for displaying an information display screen 175A shown in FIG. 18 as an example on the display 43A.

Figure 18:
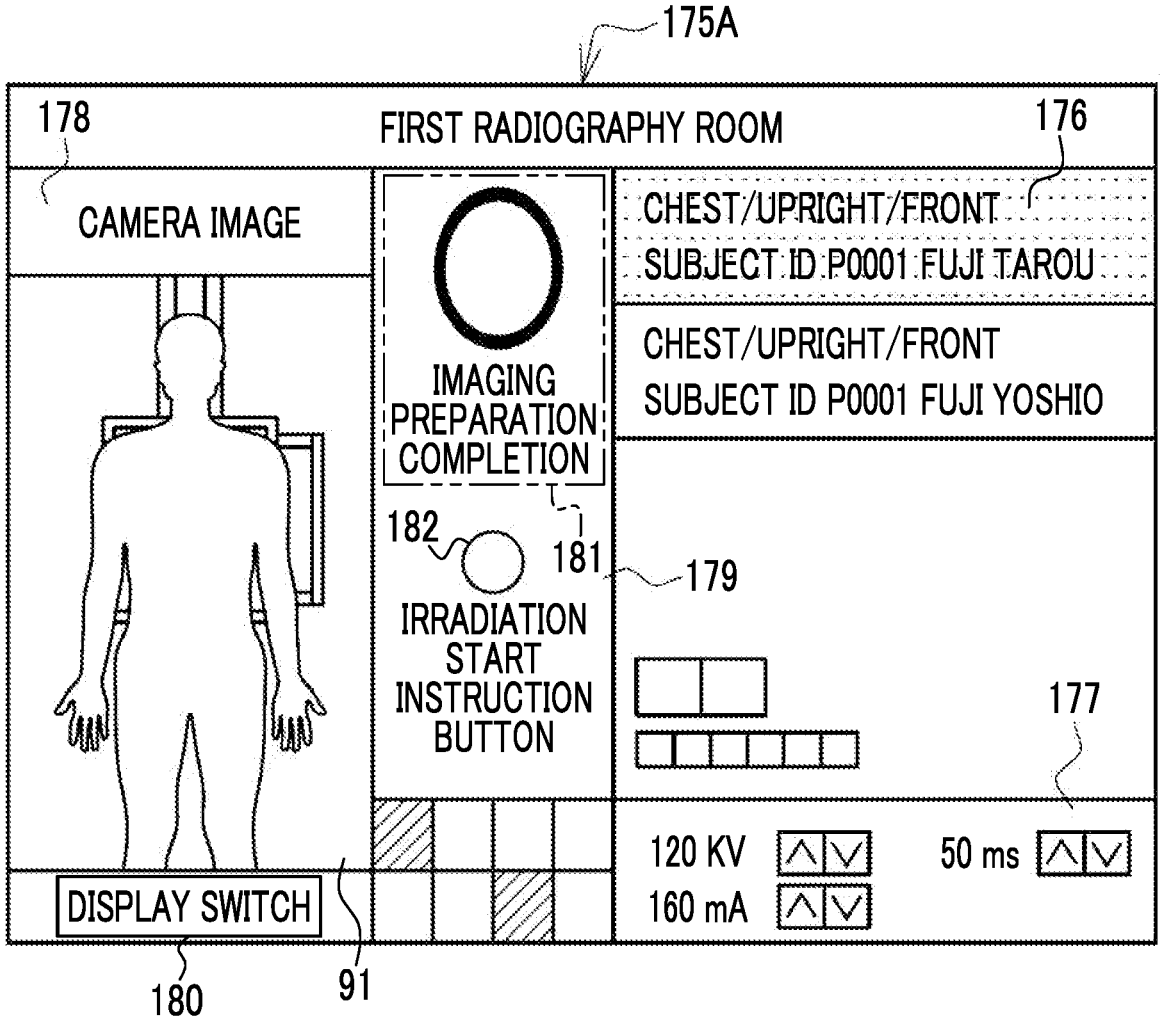
FIG. 18 is a diagram showing an information display screen on which an imaging preparation completion mark for notifying that preparation of radiography is completed and timing of the radiography is reached and an irradiation start instruction button are displayed.

In FIG. 18, the information display screen 175A has a display region 176 of the imaging menu 100 and a display region 177 of the irradiation condition. In the display region 176, sets of the imaging menu 100, the subject ID, and the name of the subject H registered until then are displayed in parallel. The imaging menu 100 with which the radiography is currently performed is displayed in color different from the other imaging menus 100 as indicated by hatching. In the display region 177, the tube voltage, the tube current, and the irradiation time of the irradiation condition are displayed in an adjustable state.

The information display screen 175A also has a display region 178 of the second optical image 90 or the third optical image 91, and a display region 179. A display switch button 180 is provided in a lower portion of the display region 178. The display switch button 180 is selected, whereby the second optical image 90 or the third optical image 91 is switched and displayed in the display region 178. The display control unit 131 sequentially updates and displays the second optical images 90 or the third optical images 91 that are sequentially output from the second camera 64 or the third camera 81 at the predetermined frame rate, in the display region 178. That is, the second optical images 90 or the third optical images 91 that are displayed in the display region 178 are a live view image (video).

In a case where the status recognition unit 127 recognizes that the progress status is "subject positioning completion", and the signal indicating that the timing of the radiography is reached is received from the status recognition unit 127, the display control unit 131 makes an imaging preparation completion mark 181 and an irradiation start instruction button 182 appear in the display region 179. The imaging preparation completion mark 181 is a mark for notifying the operator OP that the preparation of the radiography of the subject H1 is completed in the radiography room 10A, and the timing of the radiography is reached. The imaging preparation completion mark 181 is composed of a circle mark and text "imaging preparation completion". The irradiation start instruction button 182 is a button for transmitting the irradiation start instruction signal 79 to the radiation source control device 78A. Voice for notifying the operator OP that the timing of the radiography is reached may be output from the speaker of the display 43A.

The operator OP views the second optical image 90 or the third optical image 91 in the display region 178, finally confirms the positioning of the subject H1, and then, selects the irradiation start instruction button 182. With this, the irradiation start instruction signal 79 is transmitted from the imaging management device 42 to the radiation source control device 78A. Then, when a set time has elapsed from the transmission of the irradiation start instruction signal 79, the irradiation of the radiation R is performed from the radiation source 32A under the control of the radiation source control device 78A. The set time in this case is set to a time enough for the subject H1 to perform a behavior of breathing in deeply and holding the breath following guide voice 152G shown in FIG. 19, for example, five seconds.

The progress status of the radiography recognized by the status recognition unit 127 may be displayed on the information display screen 175A. A color bar in which the number of bars decreases as the progress status approaches the timing of the radiography may be displayed on the information display screen 175A. The close contact degree 166 may be displayed on the second optical image 90 of the display region 178. A frame indicating the imaging region IR and a frame indicating the detection region DR may be displayed on the third optical image 91 of the display region 178. The first optical image 106 may be switched and displayed in the display region 178.

Figure 19:
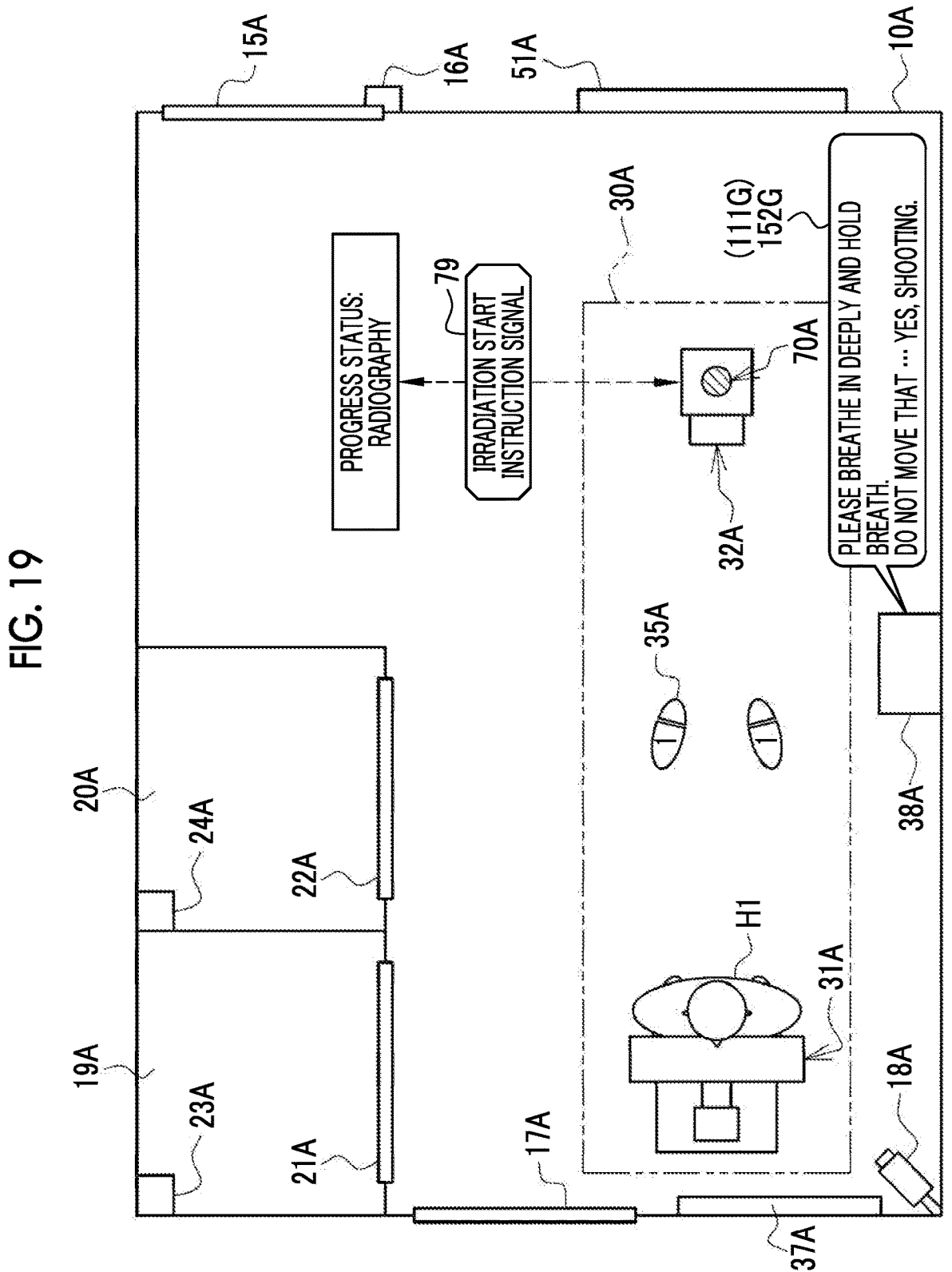
FIG. 19 is a diagram showing a case where the progress status of the radiography is "radiography"

FIG. 19 shows a case where the irradiation start instruction signal 79 is transmitted from the imaging management device 42 to the radiation source control device 78A. With the irradiation start instruction signal 79, the status recognition unit 127 recognizes that the progress status of the radiography in the radiography room 10A is "radiography". The status recognition unit 127 reads out guide information 111G from the storage 95 and outputs the guide information 111G to the speaker control unit 129. The speaker control unit 129 performs control for outputting guide voice 152G that is a voice announcement of the guide information 111G, from the speaker 38A. The guide voice 152G has the content of prompting the subject H1 to breathe in deeply, to hold the breath, and not to move that, and notifying the subject H1 of the timing of the irradiation of the radiation R.

The subject H1 breathes in deeply and holds the breath following the guide voice 152G. After the irradiation of the radiation R ends, the subject H1 returns to a normal breathing state.

Figure 20:
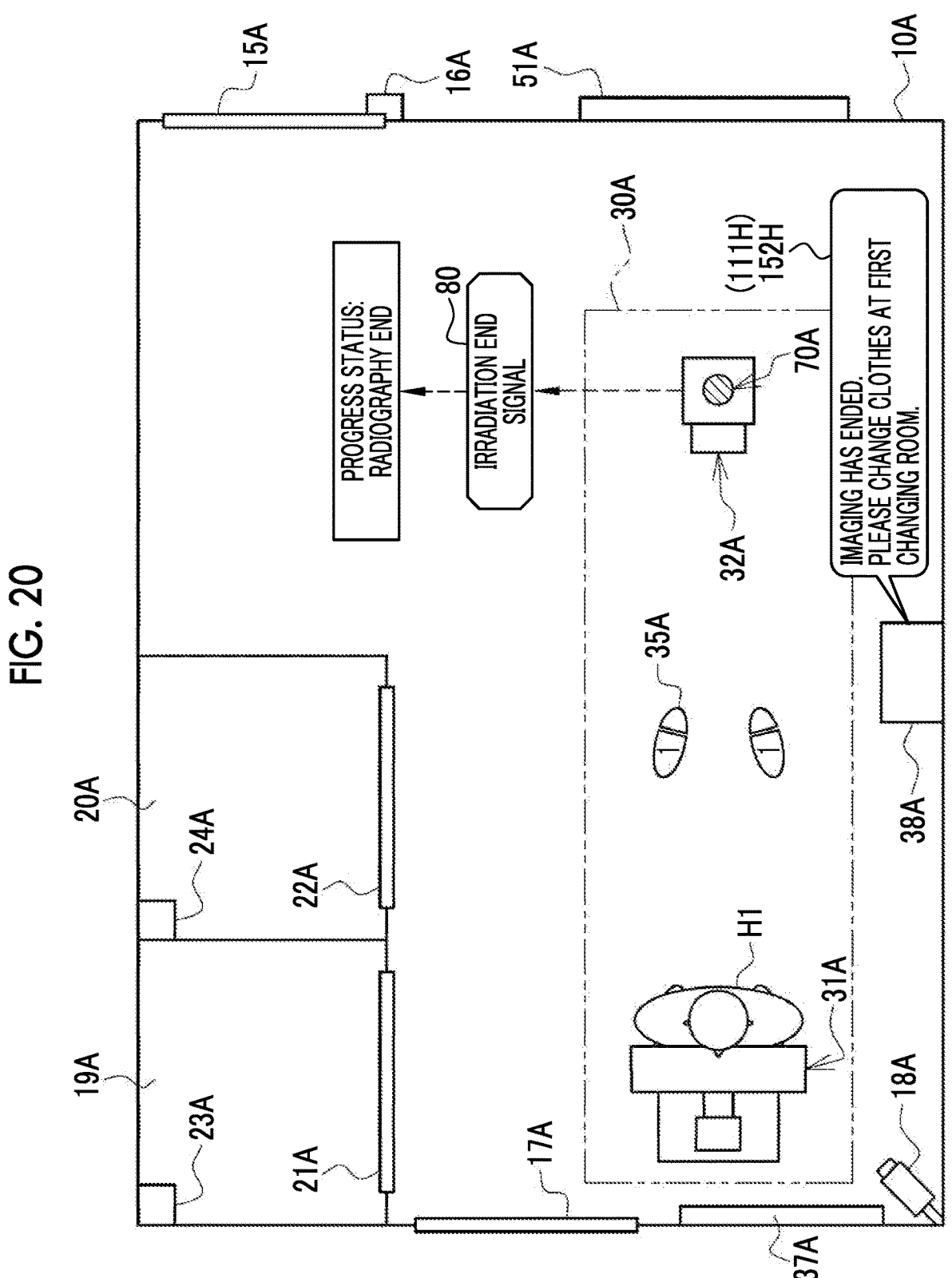
FIG. 20 is a diagram showing a case where the progress status of the radiography is "radiography end"

As shown in FIG. 20 as an example, after the irradiation of the radiation R ends, the irradiation end signal 80 is transmitted from the radiation source control device 78 to the imaging management device 42. With the irradiation end signal 80, the status recognition unit 127 recognizes that the progress status of the radiography in the radiography room 10A is "radiography end". The status recognition unit 127 reads out guide information 111H from the storage 95 and outputs the guide information 111H to the speaker control unit 129. The speaker control unit 129 performs control for outputting guide voice 152H that is a voice announcement of the guide information 111H, from the speaker 38A. The guide voice 152H has the content of notifying the subject H1 that the radiography ends, and prompting the subject H1 to change clothes to his/her clothes at the first changing room 19A.

In a case where the progress status is recognized to be "radiography end", the status recognition unit 127 transmits an operation stop instruction signal to the second camera 64 and the third camera 81. With this, the second camera 64 and the third camera 81 stop the operation.

The subject H1 opens the third door 21A, enters the first changing room 19A, and changes clothes to his/her clothes at the first changing room 19A following the guide voice 152H.

Figure 21:
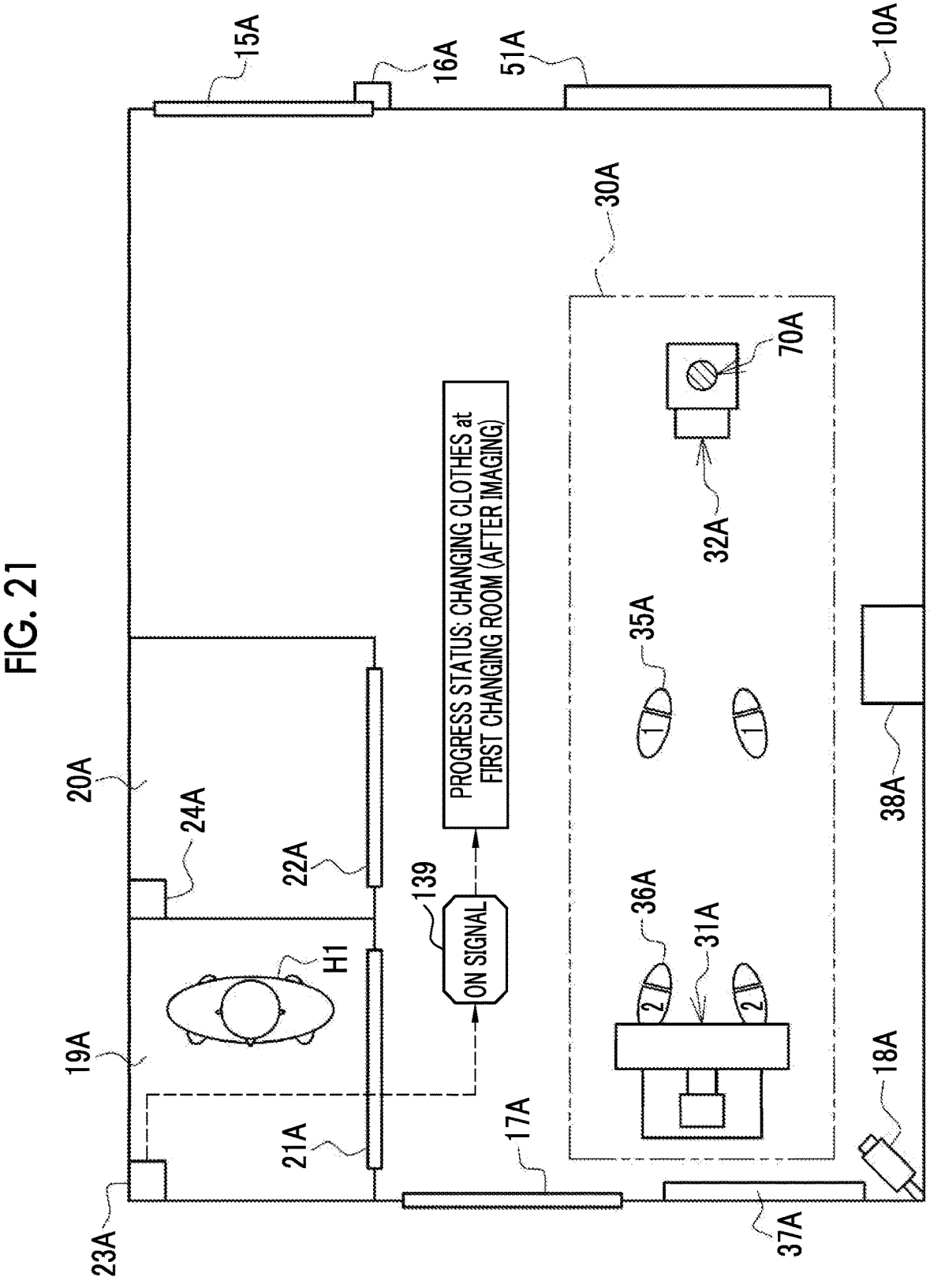
FIG. 21 is a diagram showing a case where the progress status of the radiography is "changing clothes (after imaging)"

As shown in FIG. 21 as an example, in a case where the subject H1 enters the first changing room 19A, the first human sensor 23A detects the subject H1 and outputs the on signal 139. With the on signal 139, the status recognition unit 127 recognizes that the progress status of the radiography in the radiography room 10A is "changing clothes at first changing room (after imaging)". The status recognition unit 127 transmits a signal indicating that the progress status is recognized to be "changing clothes at first changing room (after imaging)", to the entrance control unit 128 and the monitor control unit 130.

Figure 22:
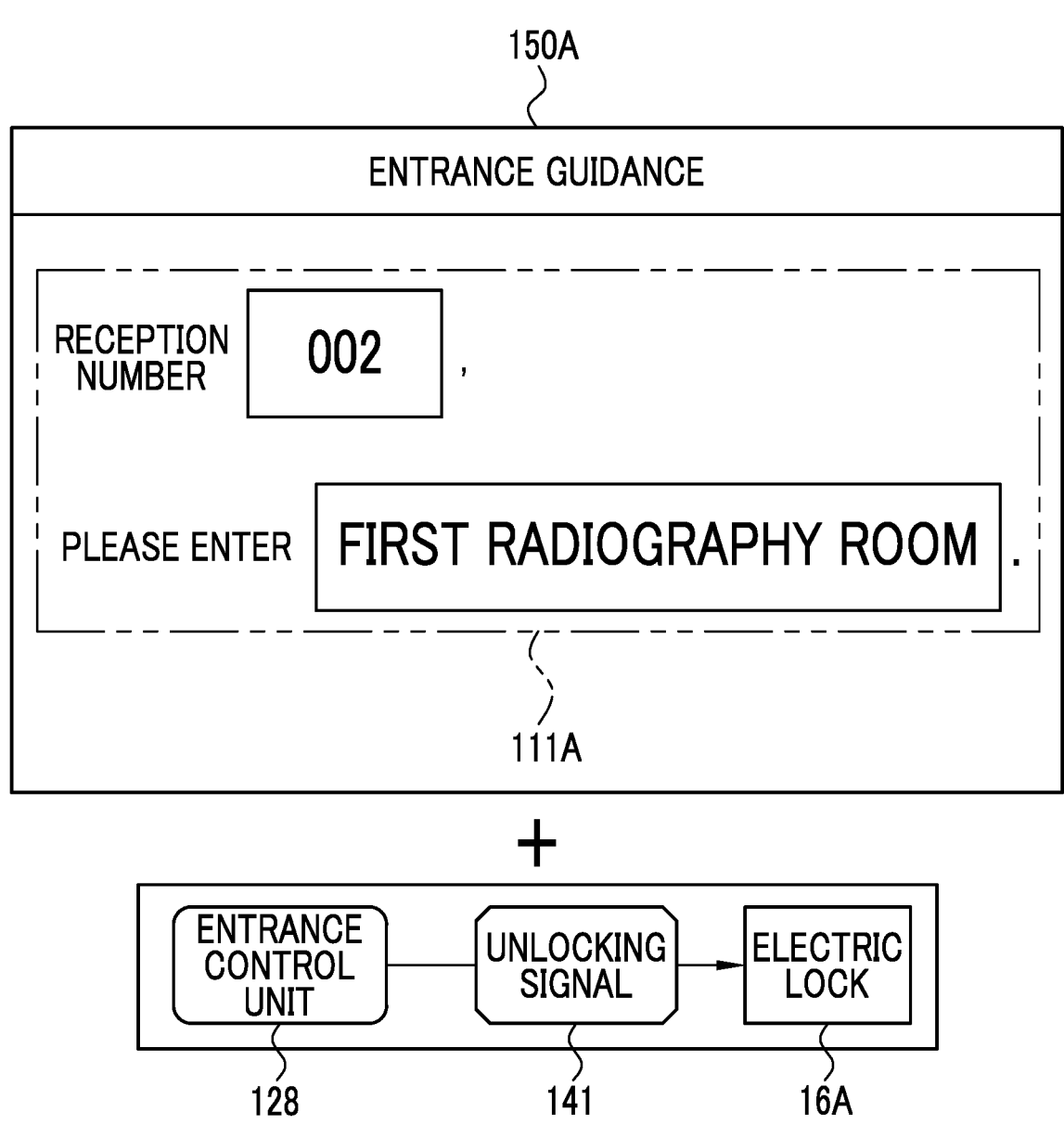
FIG. 22 is a diagram showing an entrance guidance screen for a subject of a reception number 002 and processing of the entrance control unit.

As shown in FIG. 22 as an example, the monitor control unit 130 performs control for displaying the entrance guidance screen 150A on the waiting room monitor 51A. On the entrance guidance screen 150A, the guide information 111A for prompting the subject H2 of the reception number 002 to enter the radiography room 10A in turn is displayed. The monitor control unit 130 performs control for outputting guide voice (not shown) having the same contents as the guide information 111A from the speaker of the waiting room monitor 51A.

At the same time with the display control of the entrance guidance screen 150A by the monitor control unit 130, the entrance control unit 128 outputs the unlocking signal 141 to the electric lock 16A again. With this, the electric lock 16A is unlocked, and the subject H2 can open the first door 15A and enter the radiography room 10A.

The subject H2 opens the first door 15A and enters the radiography room 10A following the guide information 111A of the entrance guidance screen 150A and the guide voice.

Figure 23:
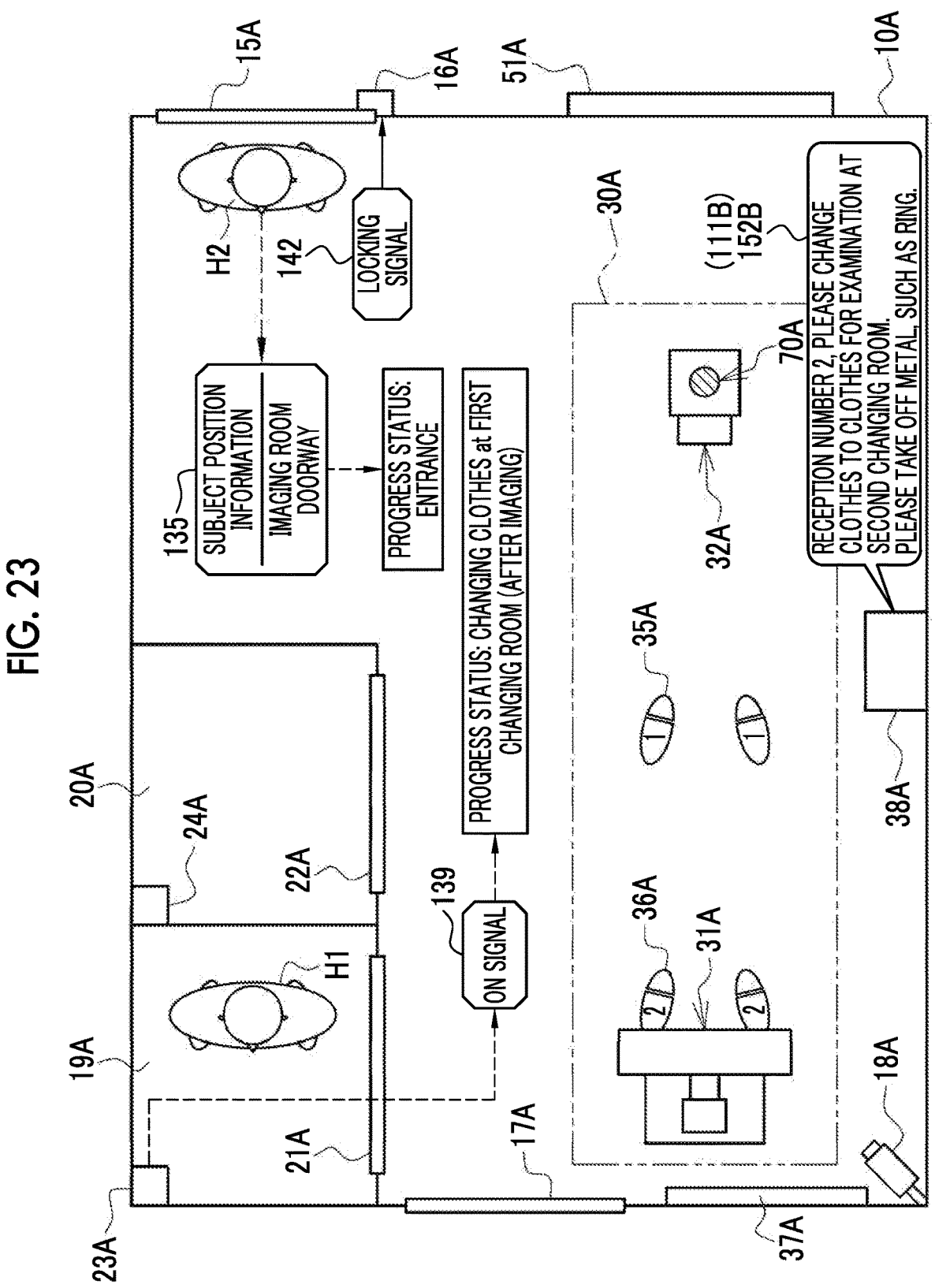
FIG. 23 is a diagram showing a case where the progress status of the radiography is "changing clothes (after imaging)" and "entrance"

Like a case of FIG. 7, FIG. 23 shows a case where the subject H2 opens the first door 15A and enters the radiography room 10A, and the subject H2 is standing in the vicinity of the doorway of the radiography room 10A. In this case, like a case of FIG. 7, the status recognition unit 127 recognizes that the progress status of the radiography in the radiography room 10A is "entrance". Like a case of FIG. 7, the speaker control unit 129 performs control of outputting the guide voice 152B from the speaker 38A. The guide voice 152B has the content of prompting the subject H2 to change clothes to clothes for examination at the second changing room 20A and to take off metal in turn. Like a case of FIG. 7, the entrance control unit 128 outputs the locking signal 142 to the electric lock 16A. With this, the electric lock 16A is locked, and a person other than the subjects H1 and H2 cannot enter the radiography room 10A.

The subject H2 opens the fourth door 22A, enters the second changing room 20A, and changes clothes to the clothes for examination at the second changing room 20A following the guide voice 152B. The subject H2 takes off metal, such as a ring or a wristwatch, in some cases.

Figure 24:
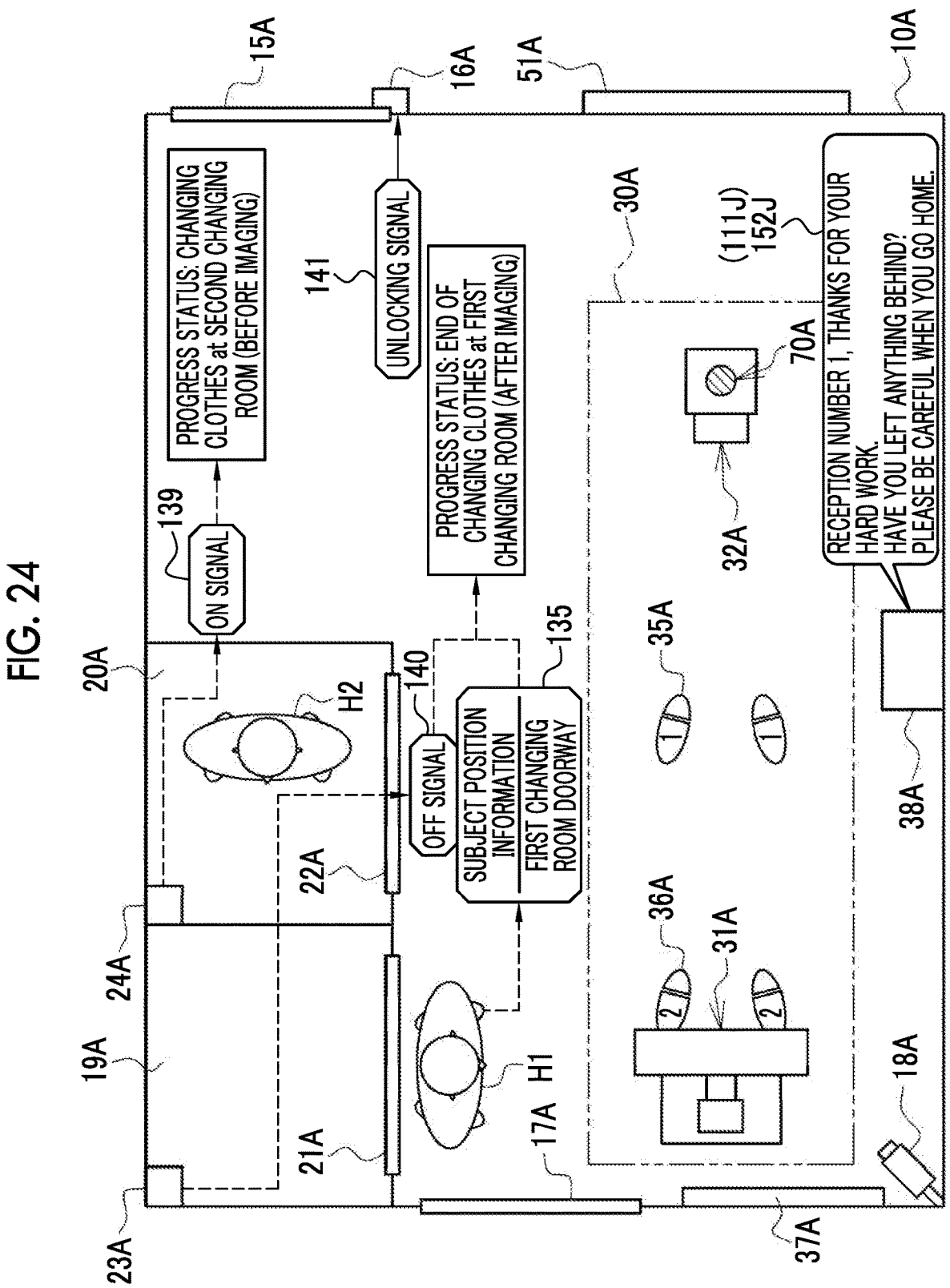
FIG. 24 is a diagram showing a case where the progress status of the radiography is "end of changing clothes (after imaging)" and "changing clothes (before imaging)"

As shown in FIG. 24 as an example, in a case where the subject H2 enters the second changing room 20A, the second human sensor 24A detects the subject H2 and outputs the on signal 139. With the on signal 139, the status recognition unit 127 recognizes the progress status of the radiography in the radiography room 10A is "changing clothes at second changing room (before imaging)".

FIG. 24 shows a case where the subject H1 ends changing clothes to his/her clothes, the subject H1 returns from the first changing room 19A to the radiography room 10A, and the subject H1 is standing in the vicinity of the doorway of the first changing room 19A. In this case, the subject position information 135 has the content of "first changing room doorway". In this case, since the subject H1 is not detected, the first human sensor 23A outputs the off signal 140. With the subject position information 135 and the off signal 140, the status recognition unit 127 recognizes that the progress status of the radiography in the radiography room 10A is "end of changing clothes at first changing room (after imaging)". The status recognition unit 127 reads out guide information 111J from the storage 95 and outputs the guide information 111J to the speaker control unit 129. The speaker control unit 129 performs control for outputting guide voice 152J that is a voice announcement of the guide information 111J, from the speaker 38A. The guide voice 152J has the content of prompting the subject H1 to exit from the radiography room 10A.

The status recognition unit 127 outputs a signal indicating that the progress status is recognized to be "end of changing clothes at first changing room (after imaging)", to the entrance control unit 128. The entrance control unit 128 receives the signal from the status recognition unit 127 indicating that the progress status is recognized to be "end of changing clothes at first changing room (after imaging)", and outputs the unlocking signal 141 to the electric lock 16A. With this, the electric lock 16A is unlocked, and the subject H1 can open the first door 15A and exit the radiography room 10A.

Figure 25:
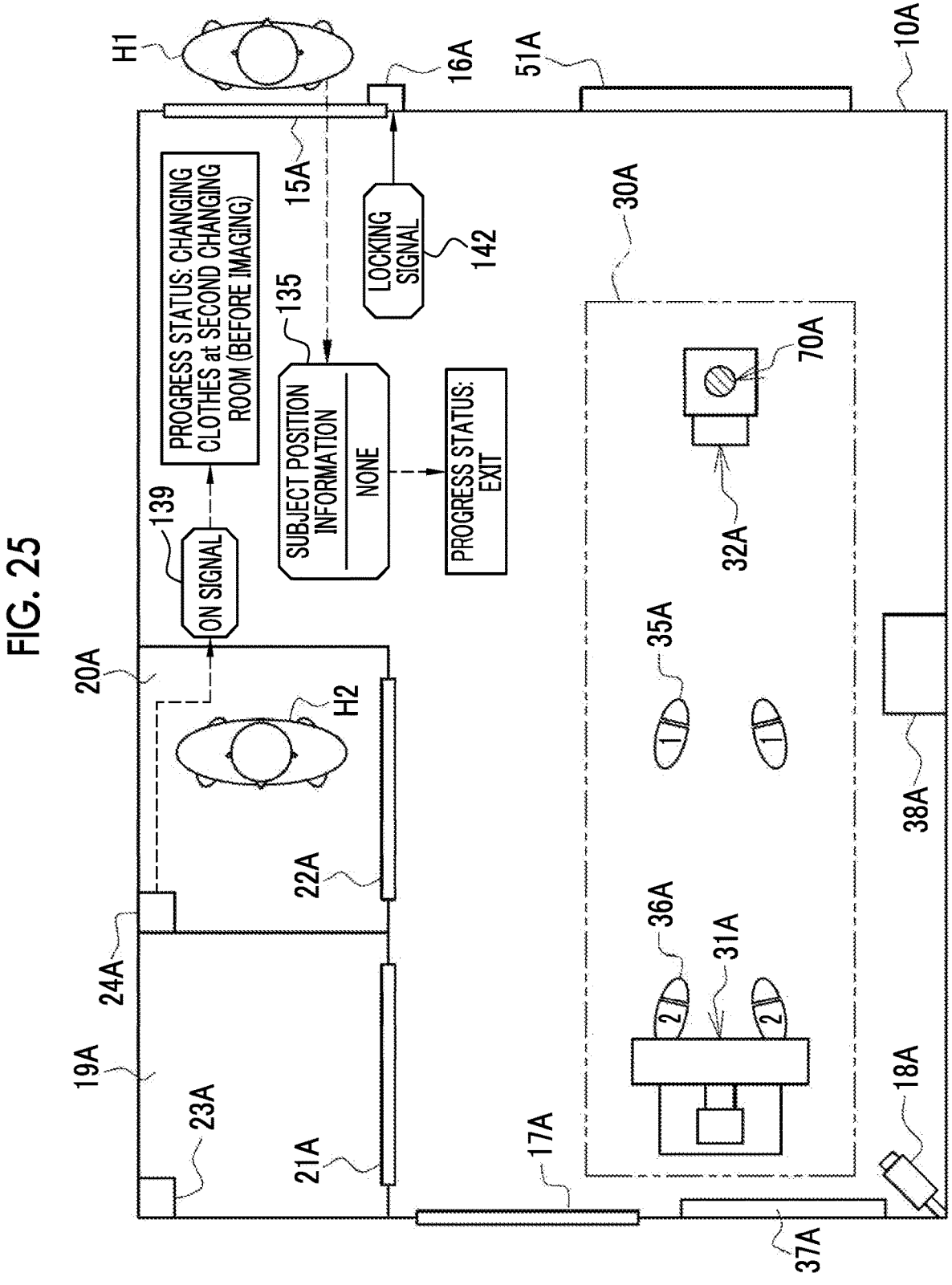
FIG. 25 is a diagram showing a case where the progress status of the radiography is "exit" and "changing clothes (before imaging)"

FIG. 25 shows a case where the subject H1 exits the radiography room 10A. In this case, the subject position information 135 transits from "imaging room doorway" to "none". With the transition of the subject position information 135, the status recognition unit 127 recognizes that the progress status of the radiography in the radiography room 10A is "exit".

The status recognition unit 127 outputs a signal indicating that the progress status is recognized to be "exit", to the entrance control unit 128. In a case where the signal indicating that the progress status is recognized to be "exit" is received from the status recognition unit 127, the entrance control unit 128 outputs the locking signal 142 to the electric lock 16A. With this, the electric lock 16A is locked, and a person other than the subject H2 cannot enter the radiography room 10A.

Figure 26:
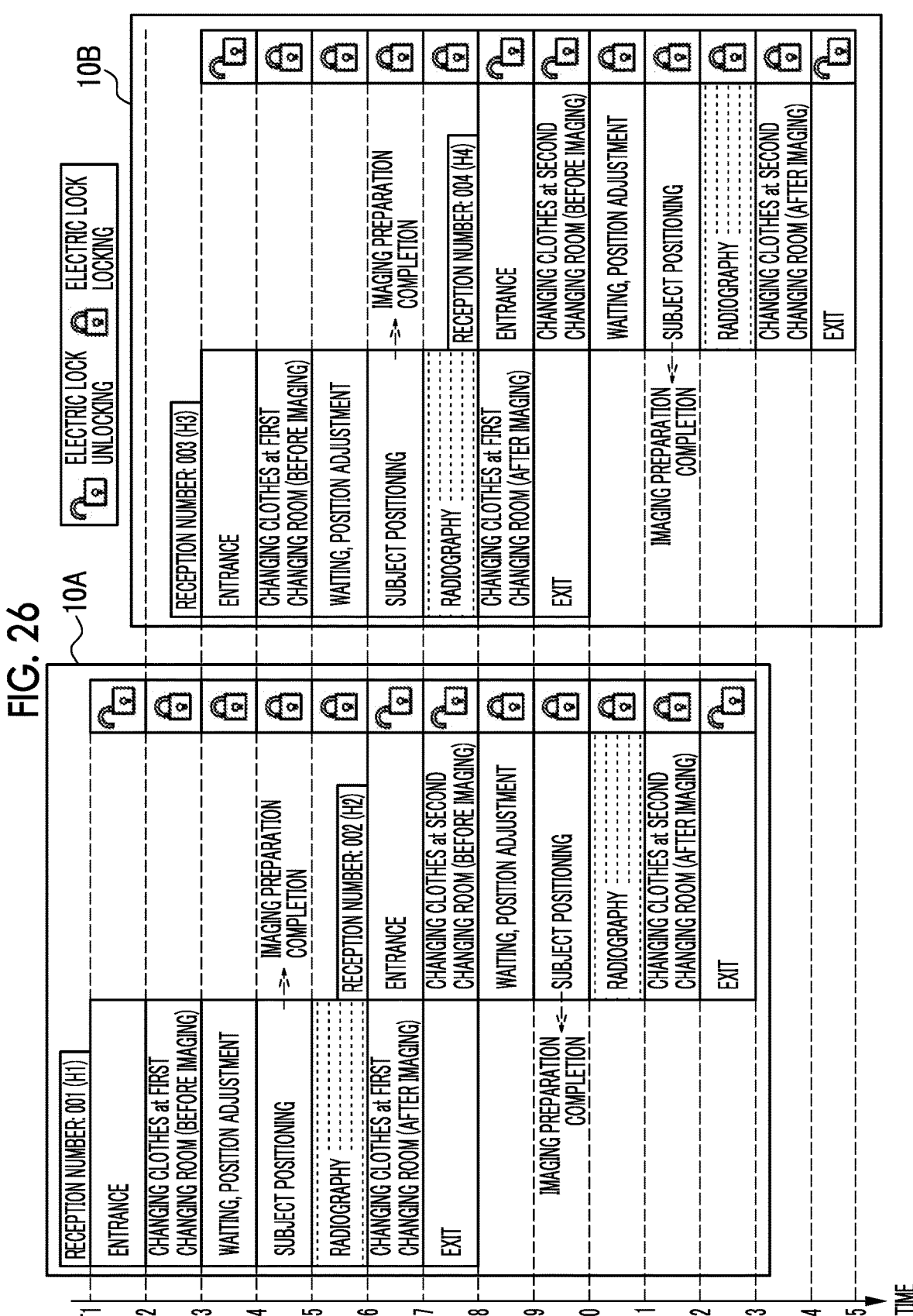
FIG. 26 is a diagram showing entrance control into the radiography room by the imaging management device.

FIG. 26 is a diagram showing an example of control of the entrance timing into the radiography rooms 10A and 10B by the entrance control unit 128. In the radiography room 10A, the radiography of the subject H1 of the reception number 001 and the subject H2 of the reception number 002 is performed. In the radiography room 10B, radiography of a subject H3 of a reception number 003 and a subject H4 of a reception number 004 is performed. In this case, the entrance control unit 128 first outputs the unlocking signal 141 to the electric lock 16A of the first door 15A of the radiography room 10A at time Ti and unlocks the electric lock 16A. With this, the subject H1 enters the radiography room 10A.

After the entrance of the subject H1, the entrance control unit 128 outputs the locking signal 142 to the electric lock 16A and locks the electric lock 16A. With this, entrance of a person other than the subject H1 into the radiography room 10A is impossible. The entrance control unit 128 continues the locking state of the electric lock 16A until the subject H1 enters the first changing room 19A to change clothes to his/her clothes after the radiography.

At time T3 at which changing clothes of the subject H1 to the clothes for examination ends, and the progress status of the radiography in the radiography room 10A is "end of changing clothes at first changing room (before imaging)", the entrance control unit 128 outputs the unlocking signal 141 to an electric lock 16B of the first door 15B of the radiography room 10B and unlocks the electric lock 16B. With this, the subject H3 enters the radiography room 10B.

After the entrance of the subject H3, the entrance control unit 128 outputs the locking signal 142 to the electric lock 16B and locks the electric lock 16B. With this, entrance of a person other than the subject H3 into the radiography room 10B is impossible. The entrance control unit 128 continues the locking state of the electric lock 16B until the subject H3 enters the first changing room 19B to change clothes to his/her clothes after the radiography.

At time T6 at which the subject H1 enters the first changing room 19A to change clothes to his/her clothes after the radiography, and the progress status of the radiography in the radiography room 10A is "changing clothes at first changing room (after imaging)", the entrance control unit 128 outputs the unlocking signal 141 to the electric lock 16A and unlocks the electric lock 16A. With this, the subject H2 enters the radiography room 10A.

At time T7 at which changing clothes of the subject H1 to his/her clothes ends, and the progress status of the radiography in the radiography room 10A is "end of changing clothes at first changing room (after imaging)", the entrance control unit 128 outputs the unlocking signal 141 to the electric lock 16A and unlocks the electric lock 16A. With this, the subject H1 exits the radiography room 10A.

After the exit of the subject H1, the entrance control unit 128 outputs the locking signal 142 to the electric lock 16A and locks the electric lock 16A. With this, entrance of a person other than the subject H2 into the radiography room 10A is impossible. The entrance control unit 128 continues the locking state of the electric lock 16A until the subject H2 after the radiography ends changing clothes to his/her clothes.

At time T8 at which the subject H3 enters the first changing room 19B to change clothes to his/her clothes after the radiography, and the progress status of the radiography in the radiography room 10B is "changing clothes at first changing room (after imaging)", the entrance control unit 128 outputs the unlocking signal 141 to the electric lock 16B and unlocks the electric lock 16B. With this, the subject H4 enters the radiography room 10B.

At time T9 at which changing clothes of the subject H3 to his/her clothes ends, and the progress status of the radiography in the radiography room 10B is "end of changing clothes at first changing room (after imaging)", the entrance control unit 128 outputs the unlocking signal 141 to the electric lock 16B and unlocks the electric lock 16B. With this, the subject H3 exits the radiography room 10B.

After the exit of the subject H3, the entrance control unit 128 outputs the locking signal 142 to the electric lock 16B and locks the electric lock 16B. With this, entrance of a person other than the subject H4 into the radiography room 10B is impossible. The entrance control unit 128 continues the locking state of the electric lock 16B until the subject H4 after the radiography ends changing clothes to his/her clothes.

At time T12 at which changing clothes of the subject H2 to his/her clothes ends, and the progress status of the radiography in the radiography room 10A is "end of changing clothes at second changing room (after imaging)", the entrance control unit 128 outputs the unlocking signal 141 to the electric lock 16A and unlocks the electric lock 16A. With this, the subject H2 exits the radiography room 10A.

At time T14 at which changing clothes of the subject H4 to his/her clothes ends, and the progress status of the radiography in the radiography room 10B is "end of changing clothes at second changing room (after imaging)", the entrance control unit 128 outputs the unlocking signal 141 to the electric lock 16B and unlocks the electric lock 16B. With this, the subject H4 exits the radiography room 10B.

In the radiography room 10A, the radiography for the subject H1 is started at time T5, and the radiography for the subject H2 is started at time T10. On the other hand, in the radiography room 10B, as much as the entrance timing is shifted, the radiography for the subject H3 is started at time T7, and the radiography for the subject H4 is started at time T12.

In the radiography room 10A, since the subject H2 enters while the subject H1 is changing clothes to his/her clothes, and the subject H1 exits while the subject H2 is changing clothes to the clothes for examination, the subject H1 and the subject H2 do not come into contact with each other. Similarly, in the radiography room 10B, since the subject H4 enters while the subject H3 is changing clothes to his/her clothes, and the subject H3 exits while the subject H4 is changing clothes to the clothes for examination, the subject H3 and the subject H4 do not come into contact with each other.

Figure 27:
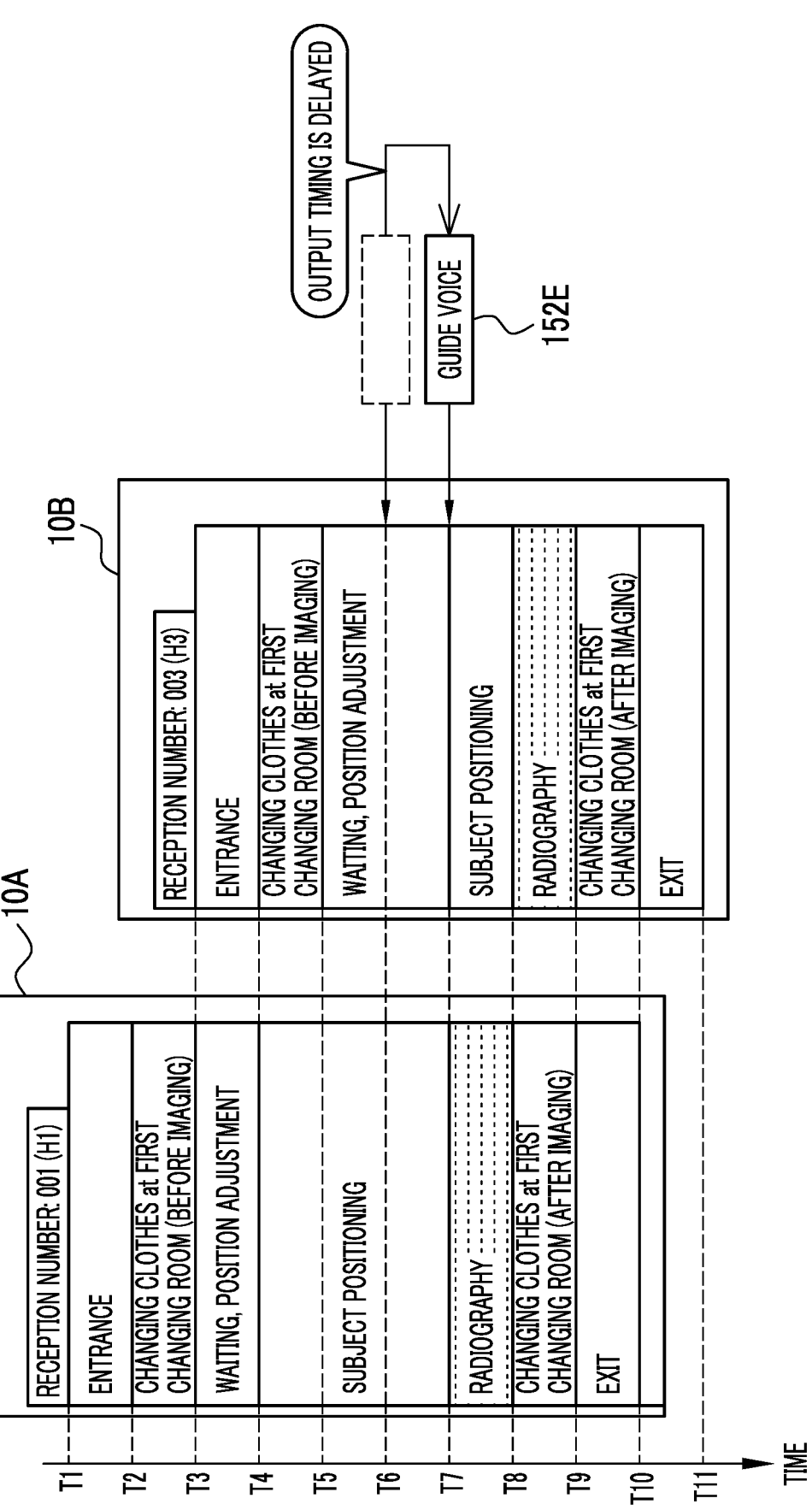
FIG. 27 is a diagram showing output control of guide information by the imaging management device.

FIG. 27 is a diagram showing an example of control of the output timing of the guide voice 152 by the speaker control unit 129. FIG. 27 illustrates a case where the subject positioning of the subject H1 in the radiography room 10A is prolonged, and the start timing of the subject positioning of the subject H3 in the radiography room 10B catches up with the entrance timing regardless of shifting of the entrance timing. In this case, the speaker control unit 129 delays the output timing of the guide voice 152E. Specifically, the speaker control unit 129 delays the output timing of the guide voice 152E from time T6 that is the original output timing at which the progress status of the radiography in the radiography room 10B is "position adjustment end" to time T7 at which the progress status of the radiography in the radiography room 10A is "subject positioning completion". As shown in FIG. 11, the guide voice 152E has the content of prompting the subject H3 to move to the imaging position where the second footprints 36B are present, and to adjust his/her position and posture with reference to the guide screen 155 of the imaging room monitor 37B.

Figure 28:
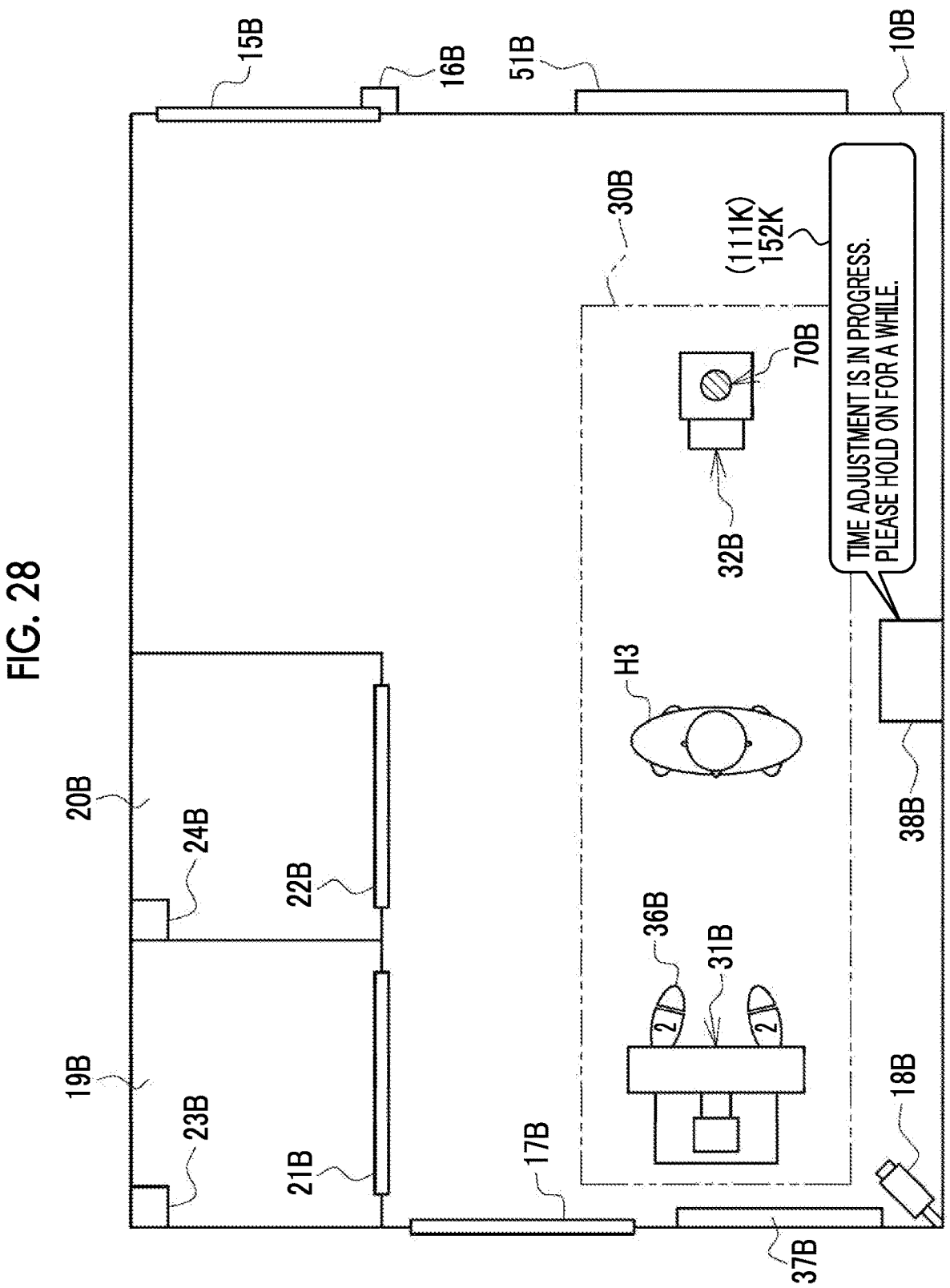
FIG. 28 is a diagram showing guide information for notifying a subject that time adjustment is in progress.

As shown in FIG. 28 as an example, while the output timing of the guide voice 152E is delayed, the speaker control unit 129 performs control for outputting guide voice 152K that is a voice announcement of guide information 111K, from the speaker 38B. The guide voice 152K has the content of notifying the subject H3 that the time adjustment is in progress and instructing the subject H3 to hold on that.

As described above, the CPU 97 of the imaging management device 42 has the status recognition unit 127, the entrance control unit 128, the speaker control unit 129, and the monitor control unit 130. The status recognition unit 127 acquires the progress status information indicating the progress status of the radiography at each of the radiography rooms 10A and 10B, such as the subject position information 135 indicating the position of the subject H in the radiography room 10. The entrance control unit 128 performs the entrance control of the subject H into the radiography rooms 10A and 10B based on the progress status information. The speaker control unit 129 and the monitor control unit 130 perform the output control of the guide voice 152 and the guide information 111 regarding the imaging toward the subject H. The CPU 97 performs the entrance control by the entrance control unit 128 and the output control by the speaker control unit 129 and the monitor control unit 130 to shift the timing of the radiography in the radiography rooms 10A and 10B. For this reason, the timing of the radiography does not conflict at the radiography rooms 10A and 10B. Accordingly, in a case of managing the radiography with the radiography systems 30A and 30B installed at the radiography rooms 10A and 10B, it is possible to suppress a situation causing confusion of the operator OP.

According to the present example, since the operator OP needs to give only minimum instructions, it is possible to reduce burden on the operator OP. According to the present example, since it is possible to reduce a chance for contact between the subject H and the operator OP, it is effective as infection control measures.

The progress status information includes the first propriety determination result 136 and the second propriety determination result 137 as imaging preparation completion information indicating that the preparation of the radiography is completed and the timing of the radiography is reached. In a case where the first propriety determination result 136 and the second propriety determination result 137 are acquired, the display control unit 131 displays the imaging preparation completion mark 181 in the display region 179 of the information display screen 175A to notify the operator OP that the timing of the radiography is reached. For this reason, the operator OP can know that the timing of the radiography is reached. It is possible to reduce a risk that the operator OP misses the timing of the radiography.

The status recognition unit 127 acquires the determination result that the status of the subject H is proper for radiography, as the imaging preparation completion information. In more detail, the status recognition unit 127 acquires the first propriety determination result 136 that the degree of close contact of the subject H with the upright imaging stand 31, to which the subject H is positioned for the radiography, is proper for the radiography, as the imaging preparation completion information. For this reason, it is possible to restrain wasteful exposure of the subject H due to imaging failure in which the radiography is performed in a state in which the degree of close contact of the subject H with the upright imaging stand 31 is not proper for the imaging. There is an increasing possibility that the radiographic image 103 proper for diagnosis is obtained.

The status recognition unit 127 acquires the second propriety determination result 137 indicating that the imaging region IR that is a region to be imaged in the radiographic image 103 falls within the detection region DR for the radiation R of the electronic cassette 34 that receives the radiation R to detect the radiographic image 103, as the imaging preparation completion information. For this reason, it is possible to restrain wasteful exposure of the subject H due to imaging failure in which the radiography is performed in a state in which the imaging region IR does not fall within the detection region DR. There is an increasing possibility that the radiographic image 103 proper for diagnosis is obtained.

The radiography system 30 has a high supply rate since one radiography system is generally installed in any medical facility regardless of the scale. For this reason, there is a high demand for a technique that manages the radiography with the radiography systems 30 by a small number of operators OP for efficiency, compared to other medical imaging systems. Accordingly, the technique of the present disclosure is applied to the radiography systems 30, whereby it is possible to meet such a demand.

In the first embodiment described above, in a case where the status recognition unit 127 acquires both the second propriety determination result 136 that the degree of close contact of the subject H with the upright imaging stand 31 is proper for the radiography and the second propriety determination result 137 indicating that the imaging region IR falls within the detection region DR, determination is made that the timing of the radiography is reached; however, the technique of the present disclosure is not limited thereto. In a case where the status recognition unit 127 acquires at least one of the first propriety determination result 136 that the degree of close contact of the subject H with the upright imaging stand 31 is proper for the radiography or the second propriety determination result 137 indicating that the imaging region IR falls within the detection region DR, determination may be made that the timing of the radiography is reached.

In the first embodiment described above, as a method of shifting the timing of the radiography at the radiography rooms 10A and 10B, an example where both the entrance control into the radiography rooms 10A and 10B by the entrance control unit 128 and the output control of the guide voice 152 and the guide information 111 by the speaker control unit 129 and the monitor control unit 130 are performed has been shown; however, the technique of the present disclosure is not limited thereto. At least one of the entrance control by the entrance control unit 128 or the output control by the speaker control unit 129 and the monitor control unit 130 may be performed to shift the timing of the radiography at the radiography rooms 10A and 10B.

Second Embodiment

Figure 29:
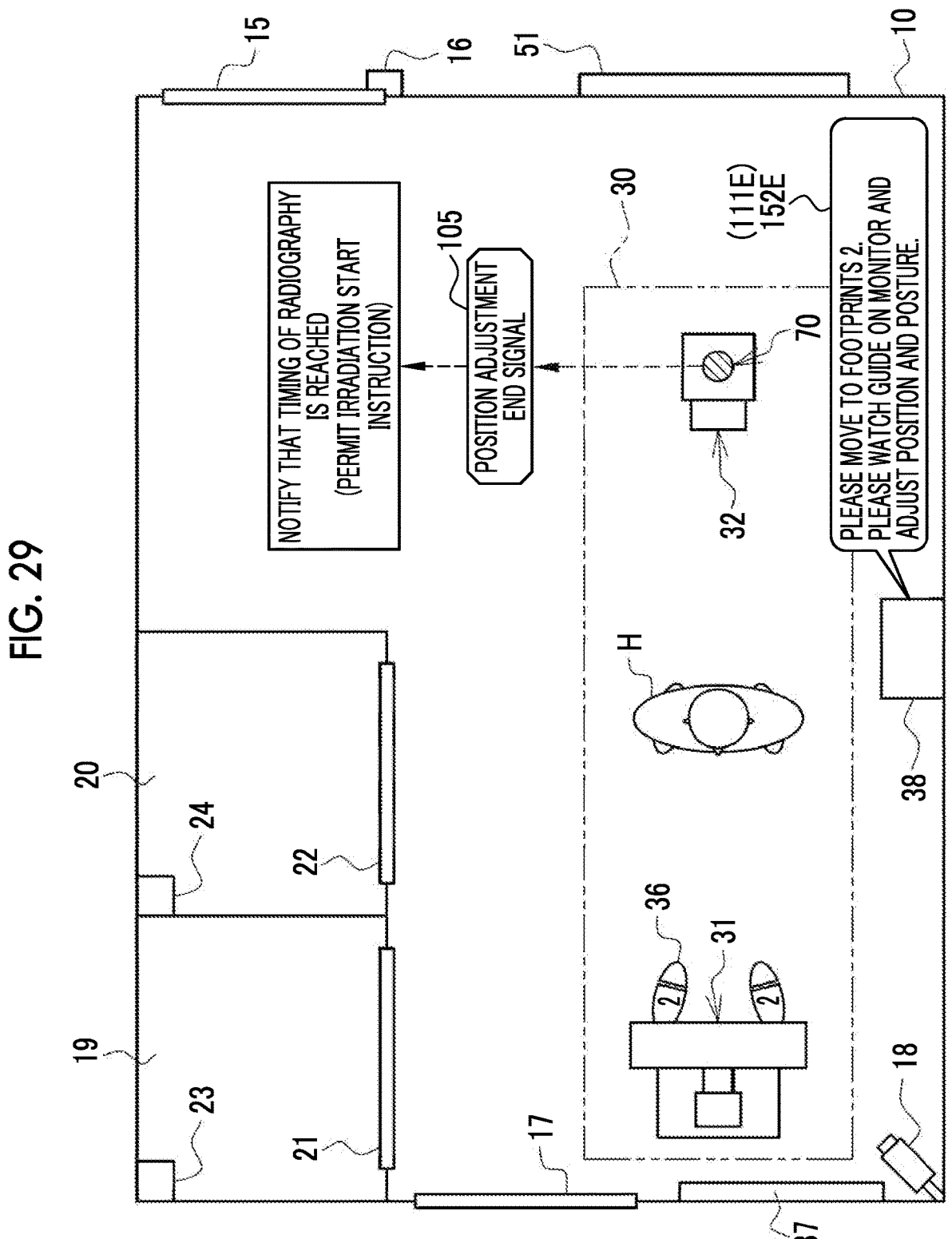
FIG. 29 is a diagram showing an aspect where, in a case where position adjustment of a radiation source and the like ends, an operator is notified that timing of imaging is reached.

As shown in FIG. 29 as an example, in a second embodiment, the status recognition unit 127 acquires the position adjustment end signal 105 from the radiation source suspension device 70, as the imaging preparation completion information. In a case where the position adjustment end signal 105 is acquired, the status recognition unit 127 outputs a signal indicating that the position adjustment end signal 105 is acquired, to the display control unit 131. The display control unit 131 performs control for displaying the information display screen 175 shown in FIG. 18 on the display 43 to notify the operator OP that the timing of the radiography is reached and to permit the operator OP to input the irradiation start instruction signal 79 of the radiation R.

In this way, in the second embodiment, the status recognition unit 127 acquires the position adjustment end signal 105 indicating that the adjustment of the positions of the radiation source 32 that performs the irradiation of the radiation R and the electronic cassette 34 that receives the radiation R to detect the radiographic image 103 ends, as the imaging preparation completion information. For this reason, it is possible to make the time at which the operator OP is notified that the timing of the radiography is reached, earlier than in a case of the first embodiment described above. For this reason, the operator OP can perform an instruction to start the irradiation of the radiation R with a plenty of time to spare.

Third Embodiment

Figure 30:
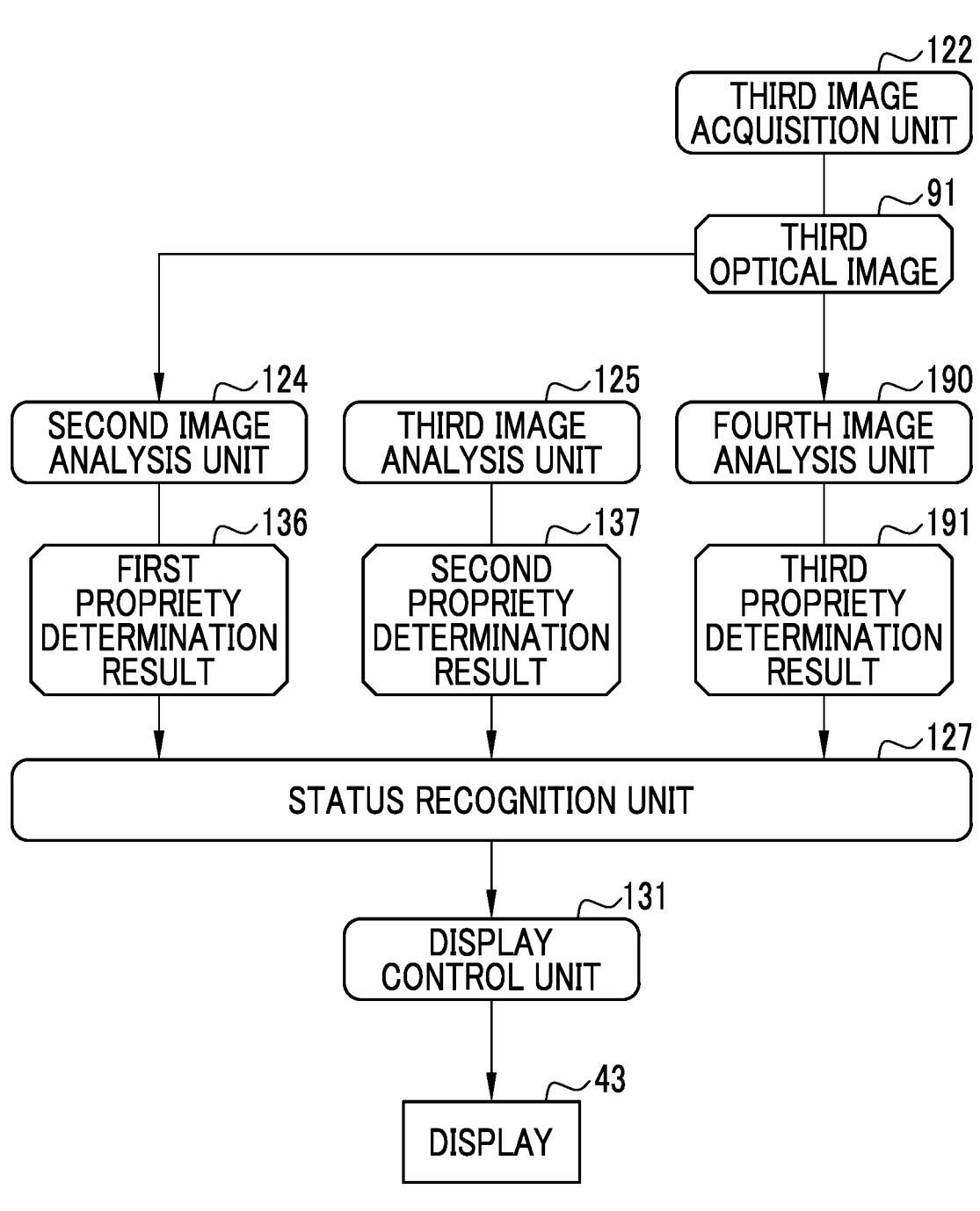
FIG. 30 is a block diagram showing processing units of a CPU of an imaging management device of a third embodiment.

As shown in FIG. 30 as an example, a CPU 97 of an imaging management device 42 of a third embodiment functions as a fourth image analysis unit 190, in addition to the processing units 120 to 131 (the units other than the third image acquisition unit 122, the second image analysis unit 124, the third image analysis unit 125, the status recognition unit 127, and the display control unit 131 are not shown) of the first embodiment described above.

The third optical images 91 from the third image acquisition unit 122 are input to the fourth image analysis unit 190. The fourth image analysis unit 190 determines whether or not a degree of stillness of the subject H is proper for the radiography, based on the third optical images 91. The fourth image analysis unit 190 outputs a third propriety determination result 191 that is a determination result regarding whether or not the degree of stillness of the subject H is proper for the radiography, to the status recognition unit 127. The degree of stillness of the subject H is an example of a "status of a subject" according to the technique of the present disclosure. The third propriety determination result 191 is an example of "progress status information", "imaging preparation completion information", and a "determination result" according to the technique of the present disclosure.

Figure 31:
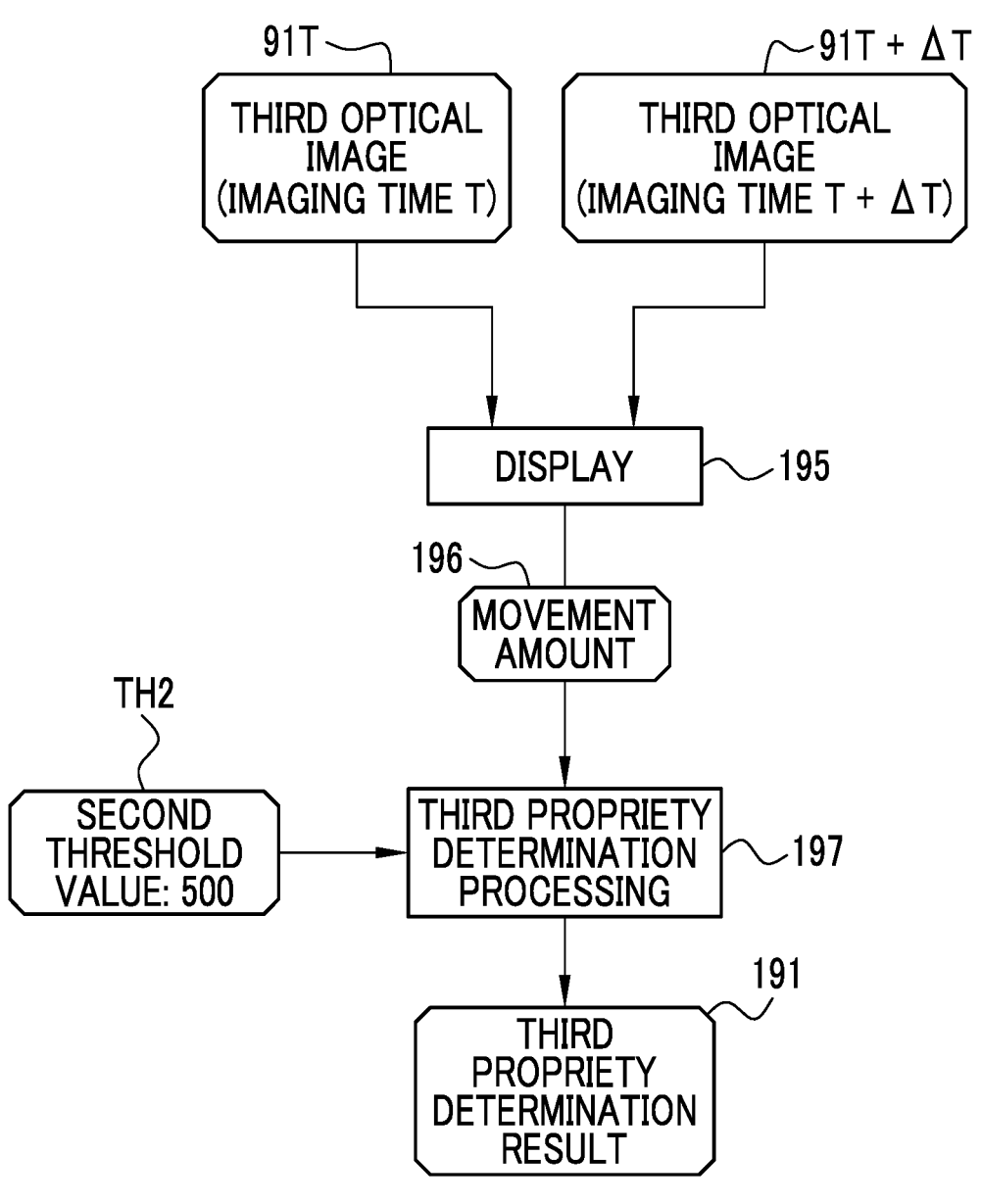
FIG. 31 is a diagram showing processing of a fourth image analysis unit.

As shown in FIG. 31 as an example, the fourth image analysis unit 190 executes movement amount calculation processing 195 on two third optical images 91 that are different in imaging time. The two third optical images 91 that are different in imaging time are specifically a third optical image 91T captured at imaging time T and a third optical image 91T+$\Delta$T captured at imaging time T+$\Delta$T. $\Delta$T is, for example, a frame interval of the third optical images 91. The movement amount calculation processing 195 calculates a representative value of a movement amount (distance) of each pixel of the third optical image 91T+$\Delta$T with respect to each pixel of the third optical image 91T, as a movement amount 196 of the subject H. The representative value is, for example, an average value or a most frequent value. The movement amount calculation processing 195 is based on an assumption that brightness of an object shown in images is not changed between temporally continuous images and the movement amounts 196 of adjacent pixels are generally the same value. The fourth image analysis unit 190 executes the movement amount calculation processing 195 each time the third optical image 91 is updated.

Next, the fourth image analysis unit 190 executes third propriety determination processing 197. The third propriety determination processing 197 is processing of comparing the movement amount 196 calculated in the movement amount calculation processing 195 with a second threshold value TH2 set in advance in magnitude, determining whether or not the degree of stillness of the subject H is proper for the radiography, and outputting the third propriety determination result 191. In a case where the voice announcement for prompting the subject H to breathe in deeply and hold the breath in the guide voice 152G is output, the fourth image analysis unit 190 executes the movement amount calculation processing 195 and the third propriety determination processing 197. Here, in the present third embodiment, the speaker control unit 129 performs control for outputting an instruction to breath in deeply and hold the breath in the guide voice 152G from the speaker 38 in a case where both the first propriety determination result 136 and the second propriety determination result 137 have the content that the status of the subject H is proper for radiography, not in a case where the irradiation start instruction signal 79 is transmitted from the imaging management device 42 to the radiation source control device 78 as in the first embodiment.

The second threshold value TH2 is set to, for example, an average value of the movement amount 196 in a case where a body movement that cannot be allowed in the radiography occurs in the subject H. In FIG. 31, 500 is set as the second threshold value TH2.

Figure 32:
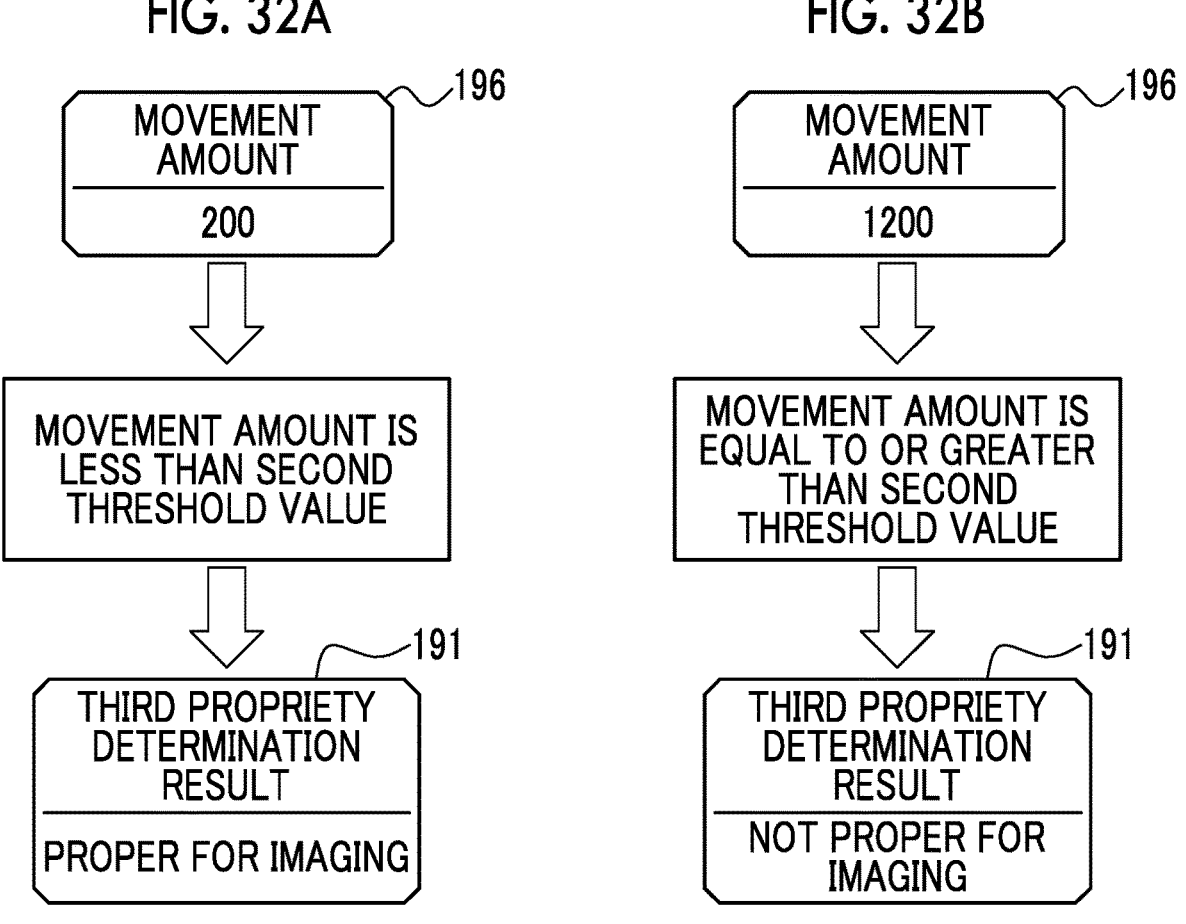
FIGS. 32A and 32B are diagrams showing the processing of the fourth image analysis unit.

As shown in FIGS. 32A and 32B as an example, the fourth image analysis unit 190 determines whether or not the degree of stillness of the subject H is proper for the radiography, depending on whether or not the movement amount 196 is less than the second threshold value TH2. As shown in FIG. 32A, in a case where the movement amount 196 is less than the second threshold value TH2, the fourth image analysis unit 190 determines that the degree of stillness of the subject H is proper for the radiography and outputs the third propriety determination result 191 indicating to be proper for the radiography. On the other hand, as shown in FIG. 32B, in a case where the movement amount 196 is equal to or greater than the second threshold value TH2, the fourth image analysis unit 190 determines that the degree of stillness of the subject H is not proper for the radiography and outputs the third propriety determination result 191 indicating to be not proper for the radiography.

Figure 33:
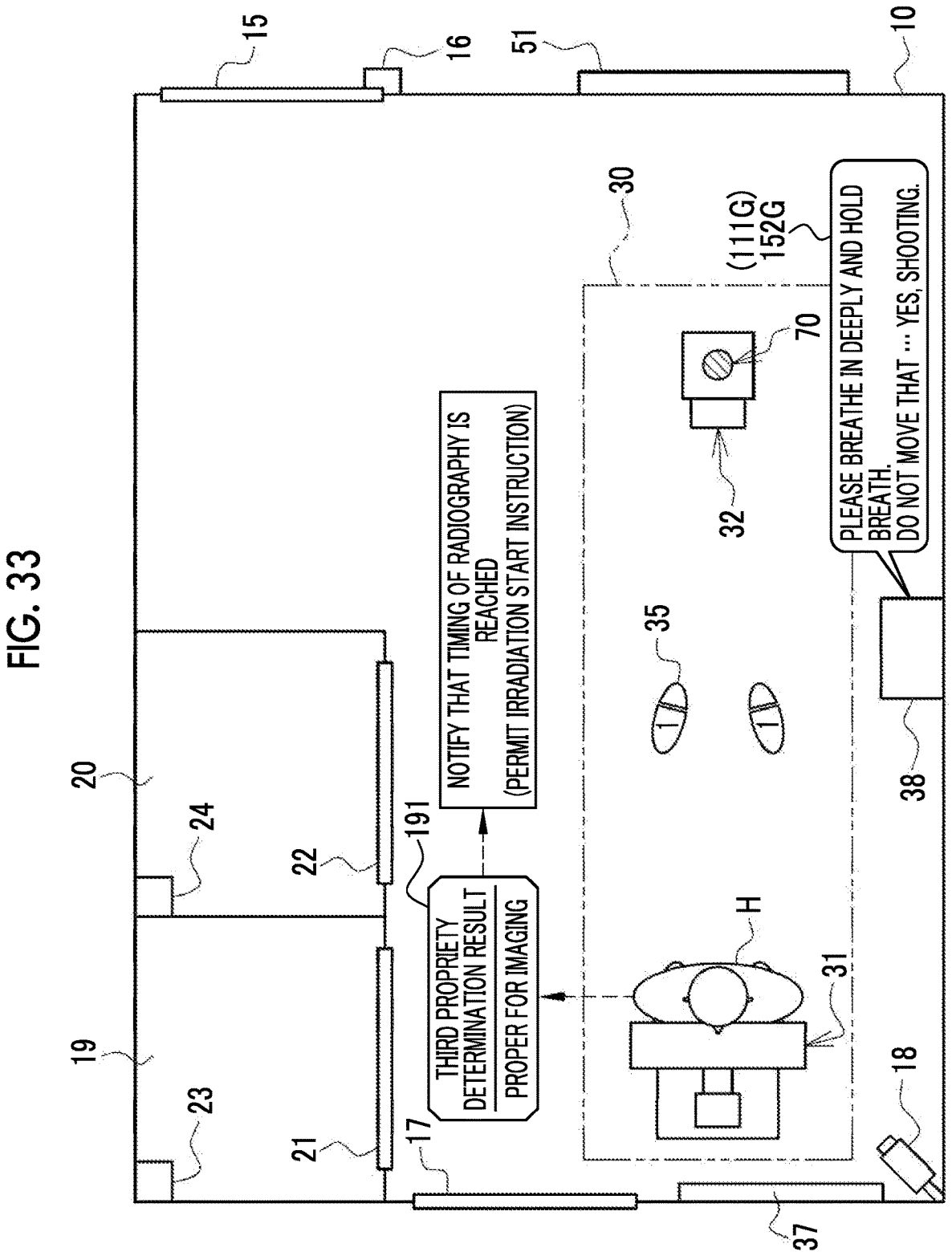
FIG. 33 is a diagram showing an aspect where, in a case of a third propriety determination result that a degree of stillness of the subject is proper for imaging, the operator is notified that the timing of imaging is reached.

As shown in FIG. 33 as an example, in a case where the third propriety determination result 191 having the content that the degree of stillness of the subject H is proper for the radiography is acquired, the status recognition unit 127 outputs a signal indicating that the degree of stillness of the subject H is proper for the radiography, to the display control unit 131. The display control unit 131 performs control for displaying the information display screen 175 shown in FIG. 18 on the display 43 to notify the operator OP that the timing of the radiography is reached and to permit the operator OP to input the irradiation start instruction signal 79 of the radiation R.

In this way, in the third embodiment, the status recognition unit 127 acquires the third propriety determination result 191 that the degree of stillness of the subject H is proper for the radiography, as the imaging preparation completion information. For this reason, just at the timing of the radiography, the operator OP can be notified that the timing of the radiography is reached. In addition, it is possible to restrain wasteful exposure of the subject H due to imaging failure in which the radiography is performed even though a body movement that cannot be allowed in the radiography occurs in the subject H. There is an increasing possibility that the radiographic image 103 proper for diagnosis is obtained.

The movement amount calculation processing 195 may be executed on the imaging region IR defined by the imaging region definition processing 170 shown in FIG. 15, not the whole of the third optical image 91. Then, only a body movement of the imaging part can be purely detected without picking up a movement of a body part unrelated to radiography other than the imaging part, for example, a head, an arm, a hand, a waist, and a foot, in a case where the imaging part is a chest. It is possible to execute higher-speed processing compared to a case where the processing is executed on the whole of the third optical image 91.

Fourth Embodiment

Figure 34:
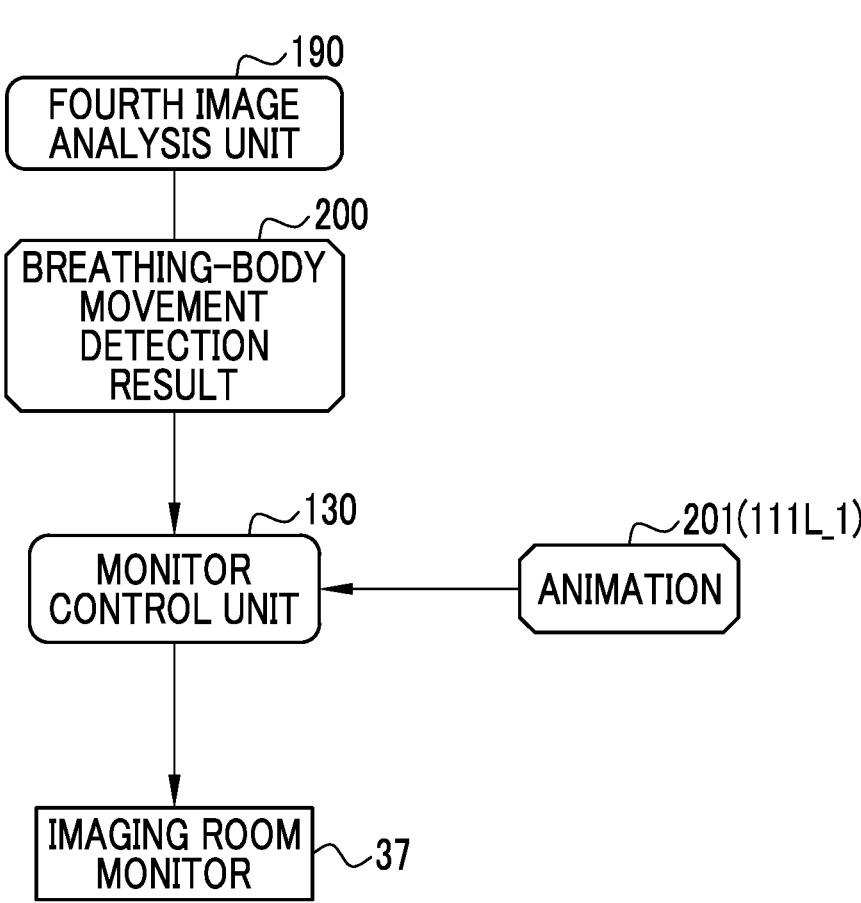
FIG. 34 is a block diagram showing processing units of a CPU of an imaging management device of a fourth embodiment.

As shown in FIG. 34 as an example, as in the third embodiment described above, a CPU 97 of an imaging management device 42 of a fourth embodiment functions as the fourth image analysis unit 190, in addition to the processing units 120 to 131 (the units other than the monitor control unit 130 are not shown) of the first embodiment described above. The fourth image analysis unit 190 outputs a component of an axis of the movement amount 196 calculated in the movement amount calculation processing 195 along a craniocaudal axis of the subject H, as a detection result (hereinafter, written as a breathing-body movement detection result) 200 of a body movement caused by breathing of the subject H to the monitor control unit 130.

Here, the reason that the component of the axis of the movement amount 196 along the craniocaudal axis of the subject H is set as the breathing-body movement detection result 200 is as follows. That is, this is because it is considered that, in a case of chest/upright/front imaging, a body movement caused by breathing of the subject H shown in the third optical image 91 is mainly due to a vertical movement of a diaphragm along a direction of the craniocaudal axis of the subject H. It is considered that, in chest/upright/side imaging, a body movement caused by breathing of the subject H shown in the third optical image 91 is mainly due to expansion and contraction of an abdomen along a direction of an antero-posterior axis of the subject H. For this reason, in a case of chest/upright/side imaging, the component of the movement amount 196 along the antero-posterior axis of the subject H may be set as the breathing-body movement detection result 200.

The monitor control unit 130 performs control for displaying an animation 201 indicating transition of the breathing state of the subject H based on the breathing-body movement detection result 200, as a part of guide information 111L_1 on the imaging room monitor 37. The imaging room monitor 37 is an example of a "display" according to the technique of the present disclosure.

Figure 35:
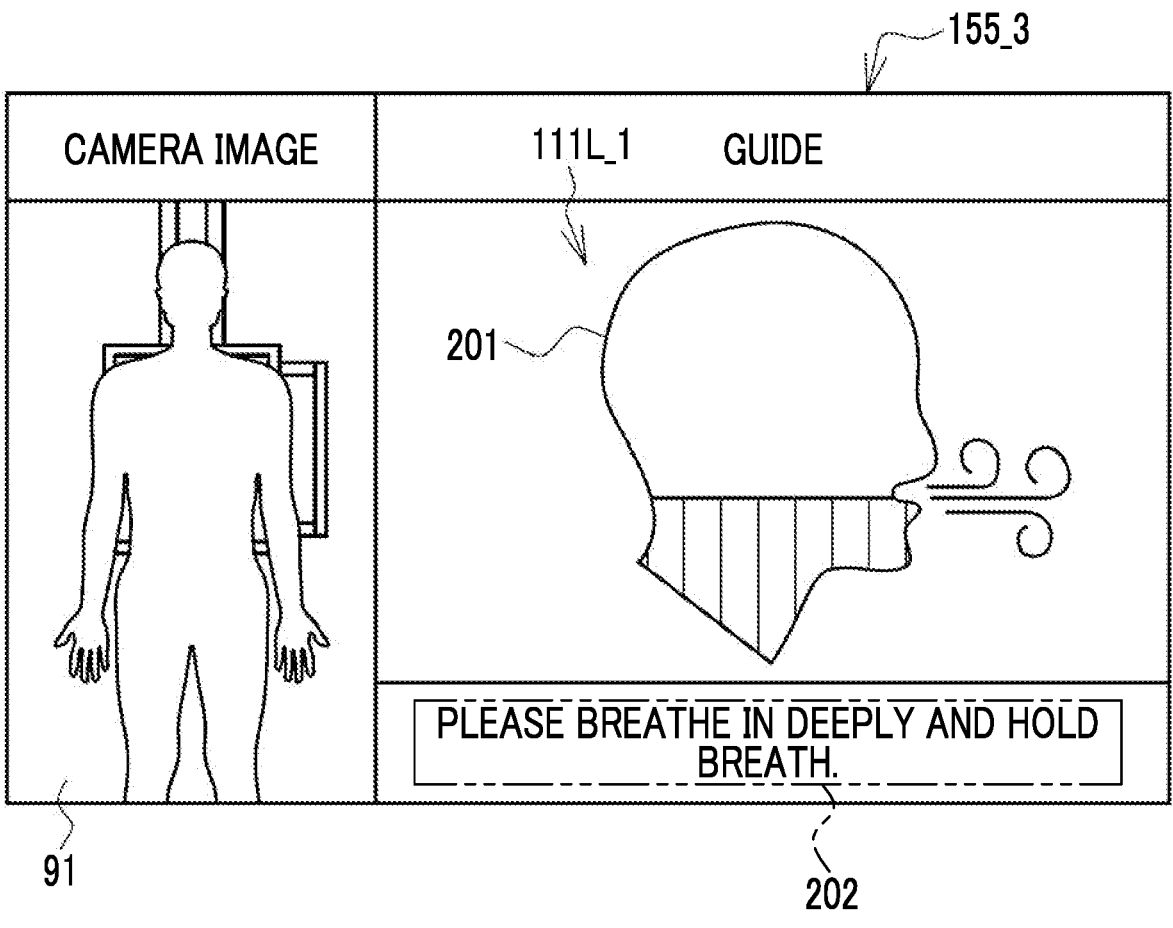
FIG. 35 is a diagram showing a guide screen of the fourth embodiment.

In more detail, the monitor control unit 130 performs control for switching display among a guide screen 155_3 shown in FIG. 35 as an example and the guide screens 155A_1 and 155A_2 shown in FIG. 12 on the imaging room monitor 37. The third optical image 91 and the guide information 111L_1 are displayed on the guide screen 155_3. The guide information 111L_1 includes the animation 201 and a message 202. The animation 201 is formed by drawing and coloring lines representing an amount of inspired air of the subject H in a profile of a person. The message 202 has the content of prompting the subject H to breathe in deeply and hold the breath.

Figure 36:
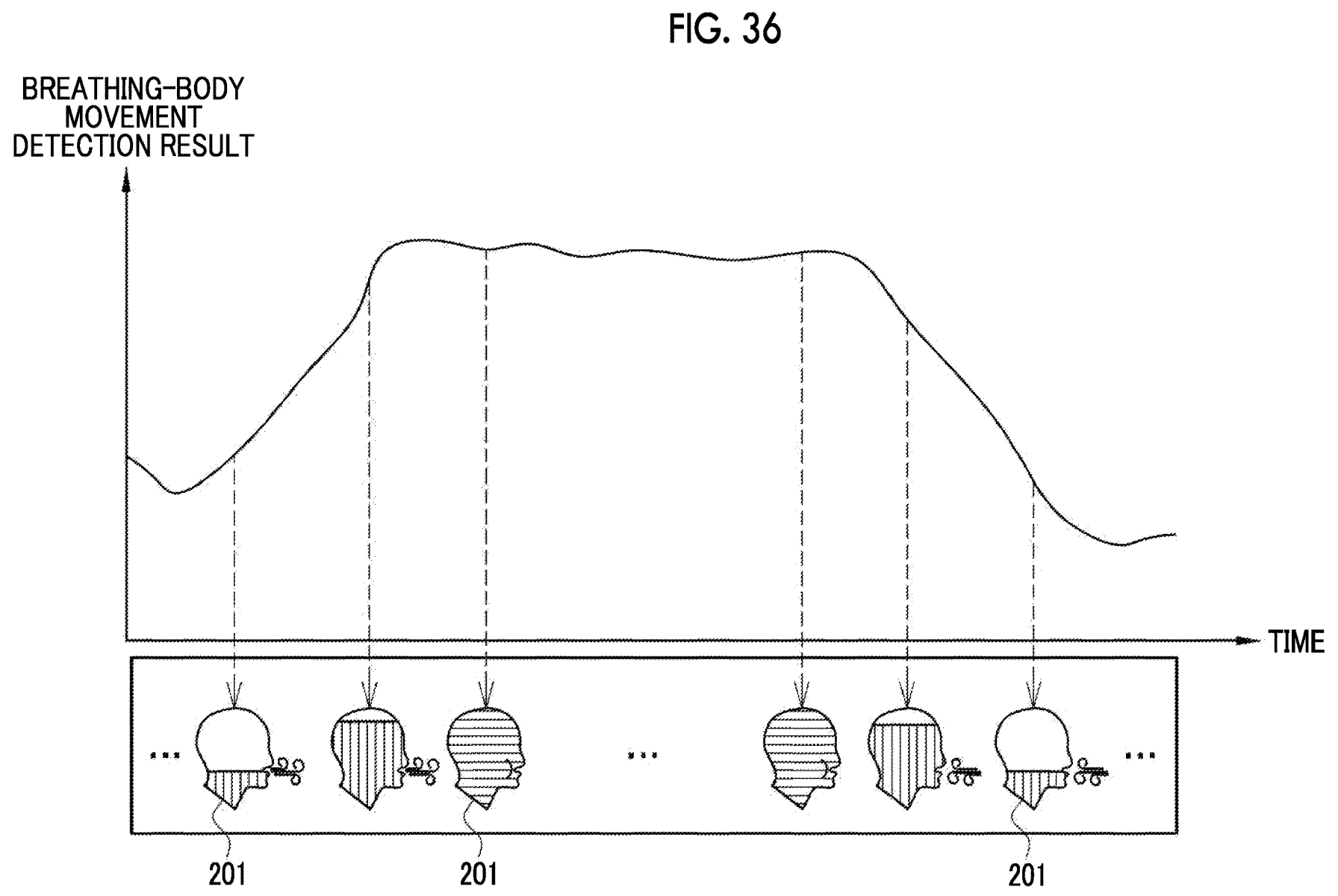

As shown in FIG. 36 as an example, the display of the animation 201 transits depending on the breathing-body movement detection result 200. That is, while the subject H breathes in and the breathing-body movement detection result 200 is increasing, a flow of wind indicating that a person is breathing in is displayed in a mouth of the profile of the person. Then, the lines indicating the amount of inspired air, and for example, a green-colored region are gradually moved from around a neck toward a head top. While the subject H holds the breath and the breathing-body movement detection result 200 is substantially constant, the flow of wind is not displayed in the mouth of the profile of the person, and a wrinkle indicating holding the breath is displayed instead. Then, the whole of the profile of the person is turned into, for example, a red-colored region. While the subject H breathes out and the breathing-body movement detection result 200 is decreasing, a flow of wind indicating breathing out is displayed in the mouth of the profile of the person. Then, the lines representing the amount of inspired air, and for example, a green-colored region are gradually moved from the head top toward around the neck.

Figure 37:
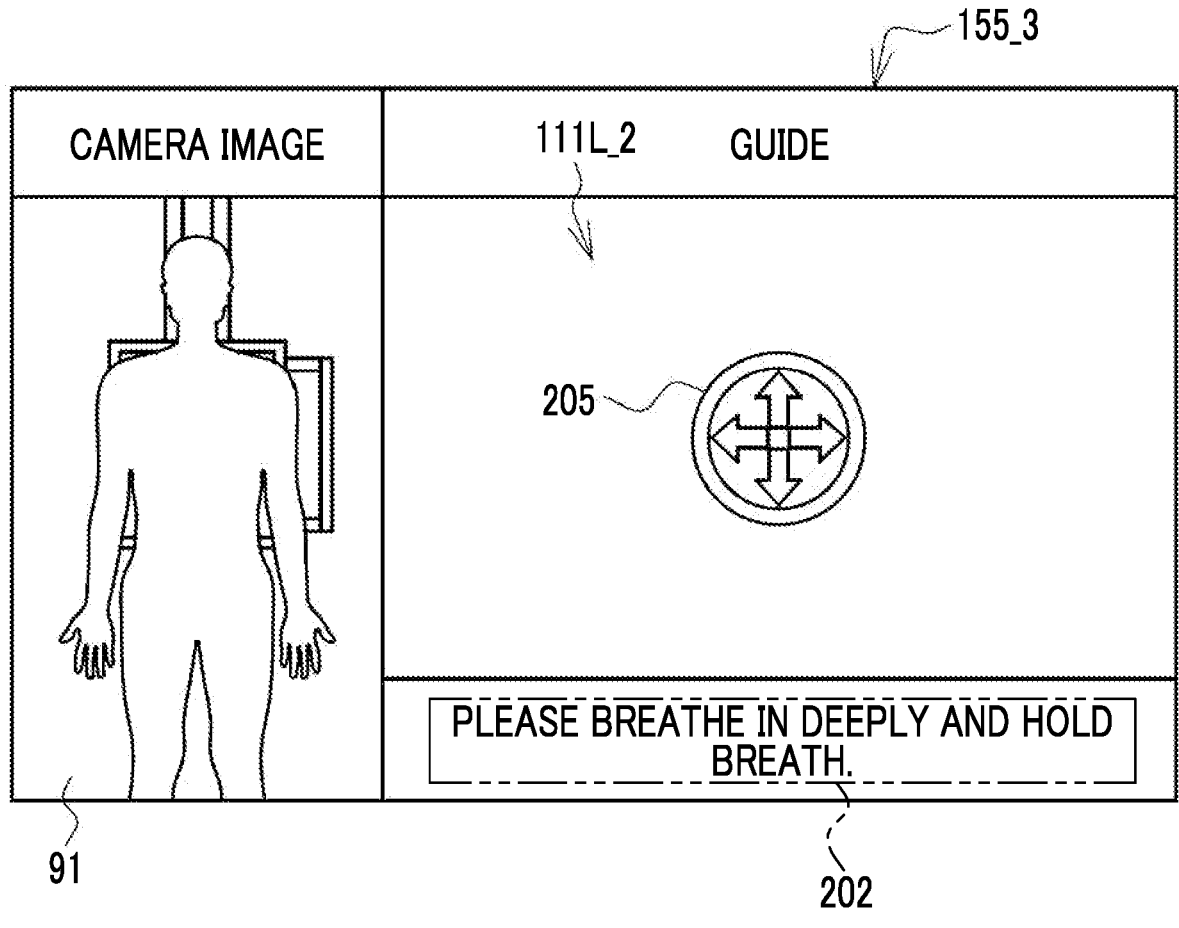
FIG. 37 is a diagram showing another example of a guide screen of the fourth embodiment.
Figure 38:
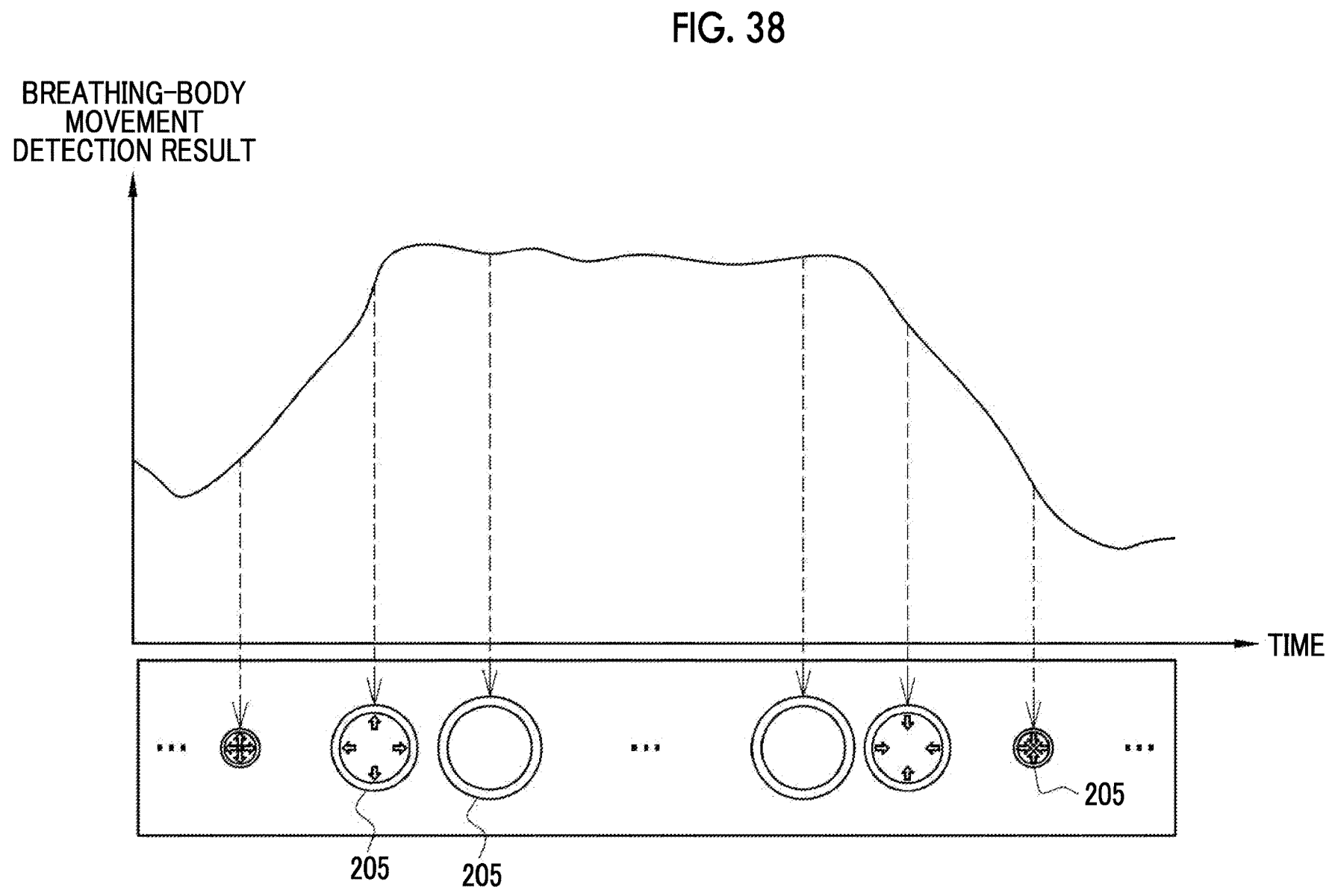

FIGS. 37 and 38 show another example of an animation. In FIG. 37, an animation 205 as a part of guide information 111L_2 displayed on the guide screen 155_3 has up, down, right, and left arrows disposed in a double circle.

As shown in FIG. 38 as an example, like the animation 201, the display of the animation 205 transits depending on the breathing-body movement detection result 200. That is, while the subject H breathes in and the breathing-body movement detection result 200 is increasing, all of the up, down, right, and left arrows in the double circle are displayed outward. Then, as the breathing-body movement detection result 200 increases, that is, as the amount of inspired air increase, the double circle inflates largely. While the subject H holds the breath and the breathing-body movement detection result 200 is substantially constant, the size of the double circle is the maximum and is not changed.

While the subject H breathes out and the breathing-body movement detection result 200 is decreasing, all of the up, down, right, and left arrows in the double circle are displayed inward. Then, as the breathing-body movement detection result 200 decreases, that is, as the amount of inspired air decreases, the double circle deflates small.

In this way, in the fourth embodiment, the monitor control unit 130 acquires the breathing-body movement detection result 200 of the subject H, and performs control for displaying the animation 201 or 205 indicating the transition of the breathing state of the subject H based on the breathing-body movement detection result 200, as a part of the guide information 111L_1 or 111L_2 on the imaging room monitor 37. For this reason, the subject H can be clearly notified of the transition of the breathing state with the animation 201 or 205. The subject H can easily know the timing of holding the breath.

Both the animations 201 and 205 may be displayed on the guide screen 155_3. A graph representing a change with time of the breathing-body movement detection result 200 may be displayed on the imaging room monitor 37 and/or the display 43.

In a case where the guide voice 152 of "breathe in" is initially sent, and the amount of inspired air indicated by the breathing-body movement detection result 200 reaches a threshold value set in advance, the guide voice 152 of "hold the breath" may be sent. In this manner, the subject H may be induced to hold the breath at the amount of inspired air proper for the radiography.

In each embodiment described above, although an example where the radiography of the radiography systems 30A and 30B installed at the radiography rooms 10A and 10B of the radiology department 2 of the same medical facility is managed has been shown, the technique of the present disclosure is not limited thereto. In each embodiment described above, although an example where the control room 11 is disposed next to the radiography rooms 10A and 10B (an example where the radiography room 10 and the control room 11 are disposed in the same building) has been shown, the technique of the present disclosure is not limited thereto. An aspect shown in FIG. 39 as an example may be made.

Figure 39:
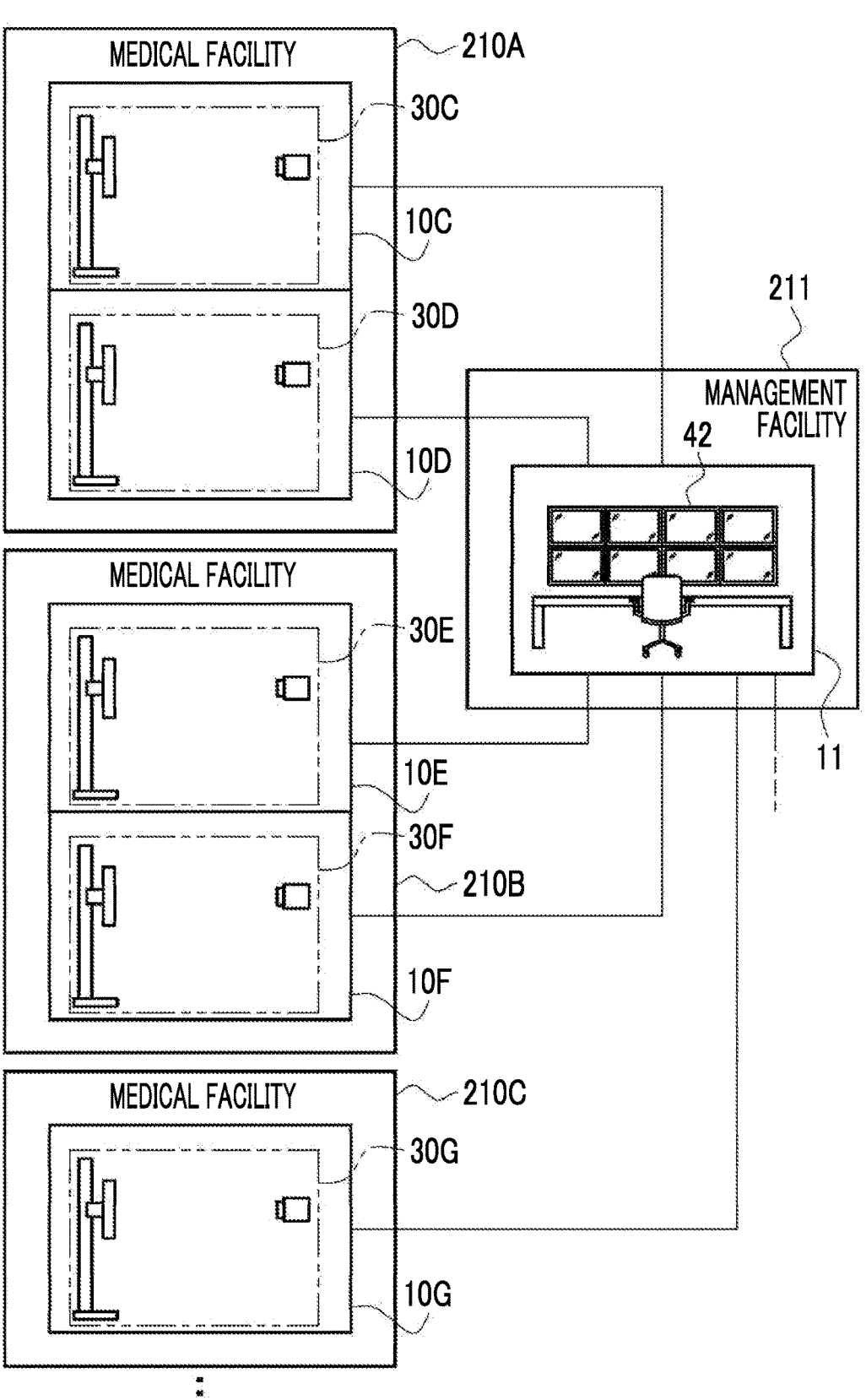
FIG. 39 is a diagram showing an example of managing imaging with radiography systems installed at radiography rooms over a plurality of medical facilities.

In FIG. 39, one management facility 211 is applied to a plurality of medical facilities 210A, 210B, 210C, and the like. There are radiography rooms 10C and 10D in the medical facility 210A, and radiography systems 30C and 30D are installed at the radiography rooms 10C and 10D, respectively. There are radiography rooms 10E and 10F in the medical facility 210B, and radiography systems 30E and 30F are installed at the radiography rooms 10E and 10F, respectively. There is a radiography room 10G in the medical facility 210C, and a radiography system 30G is installed in the radiography room 10G. There is one control room 11 in the management facility 211, and one imaging management device 42 is installed at the control room 11. In this way, the radiography systems 30 for which the radiography is managed by the imaging management device 42 may be installed in different medical facilities 210. The control room 11 may be in a building different from the radiography room 10, such as the management facility 211.

Figure 40:
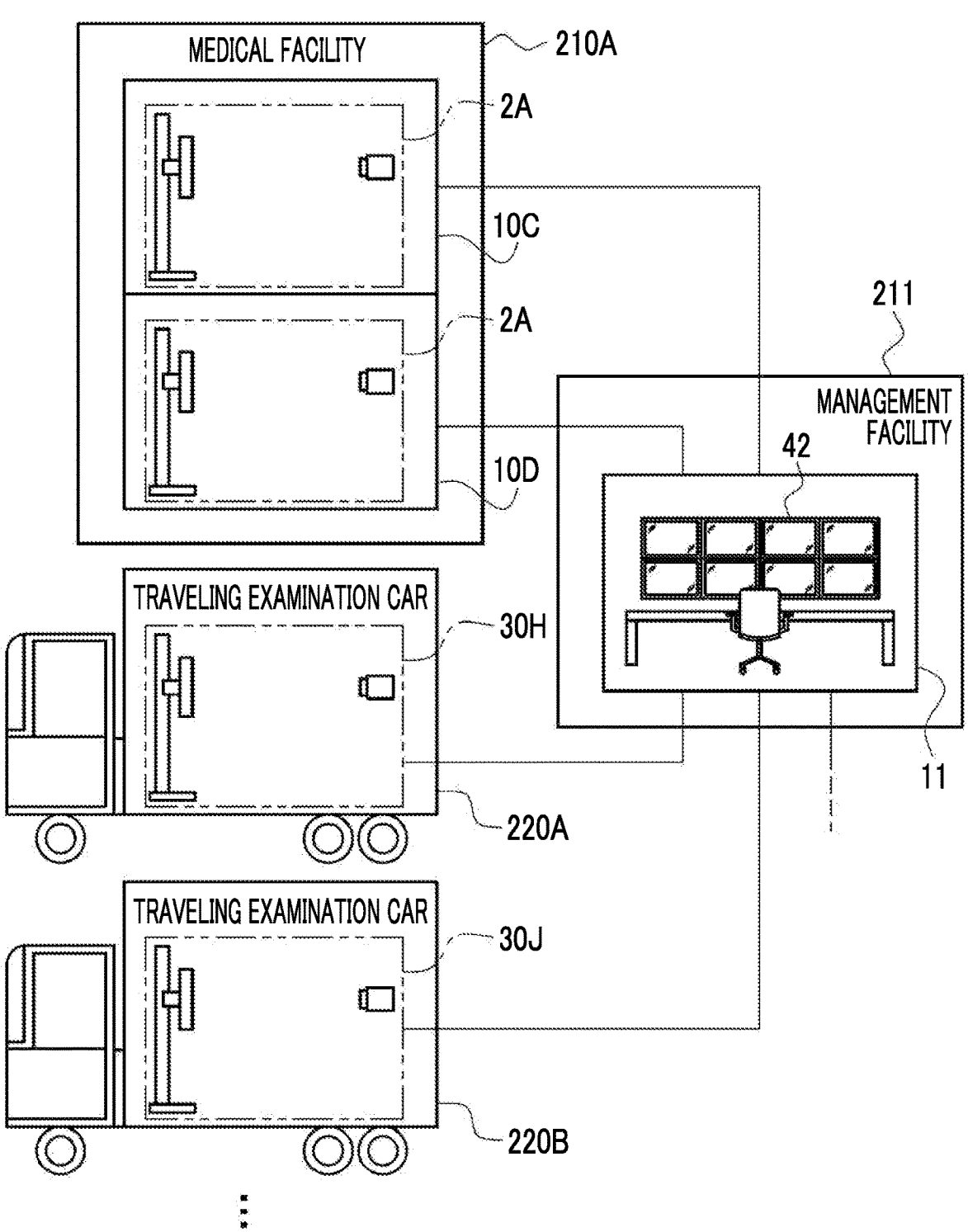
FIG. 40 is a diagram showing an example of managing imaging of radiography systems mounted in traveling examination cars, in addition to the radiography systems installed at the radiography rooms.

The imaging place is not limited to the radiography room 10. As shown in FIG. 40 as an example, the imaging place may be a traveling examination car 220, such as traveling examination cars 220A and 220B. A radiography system 30H is mounted in the traveling examination car 220A, and a radiography system 30J is mounted in the traveling examination car 220B. Radiography in the traveling examination car 220 as well as the radiography room 10 can also be managed.

The traveling examination car 220 may be an autonomous driving car. In this case, to perform radiography for the subject H who is getting medical treatment at home, autonomous driving may be performed from a dispatch base of the traveling examination car 220 to the home of the subject H.

The guide information 111, the first footprints 35 and the second footprints 36, and the like may be projected onto the floor surface, the wall surface, or the ceiling 73 of the radiography room 10, the holder 33 of the upright imaging stand 31, or the like by a projector. In this case, instead of the first footprints to be intrinsically projected to the waiting position, footprints may be projected before the third door 21 of the first changing room 19 or the fourth door 22 of the second changing room 20. Then, the operator OP may be instructed to hold on for a while at the position of the footprints to shift the timing of the radiography at a plurality of imaging places. Changing a projection position of the footprints is an example of "output control of guide information" according to the technique of the present disclosure.

A monitor may be provided in each of the first changing room 19 and the second changing room 20, and guide information 111 including precautions regarding positioning for radiography to be performed from now may be displayed for the subject H who changes clothes to the clothes for examination. In this case, timing of starting the display of the guide information 111, timing of cutting off the display of the guide information 111, and/or a reproduction speed of video for displaying the guide information 111 may be shifted, and a staying time of the subject H in the first changing room 19 or the second changing room 20 may be changed to shift the timing of the radiography at a plurality of imaging places. Shifting the timing of the starting the display of the guide information 111, the timing of cutting off the display of the guide information 111, and/or the reproduction speed of video for displaying the guide information 111 is an example of "output control of guide information" according to the technique of the present disclosure.

An opening/closing detection sensor may be provided in each of the first door 15, the third door 21, and the fourth door 22, and an output of the opening/closing detection sensor may be input as progress status information to the status recognition unit 127. An electric lock may be provided in the third door 21 and the fourth door 22, and returning of the subject H from the first changing room 19 or the second changing room 20 to the radiography room 10 may be controlled.

A button for the subject H to report end of changing clothes may be provided in each of the first changing room 19 and the second changing room 20, and an operation signal of the button may be acquired as progress status information. In this case, radiography may be performed with priority from the subject H who finishes changing clothes to the clothes for examination early.

A green lamp indicating that the electric lock 16 is unlocked and a red lamp indicating that the electric lock 16 is locked may be attached to an upper portion of the first door 15, and the subject H may recognize the unlocking state/locking state of the electric lock 16 at a glance.

A layout of the radiography room 10 and the like shown in FIG. 1 is merely an example. For this reason, in the radiography room 10, not only the upright imaging stand 31 but also a decubitus imaging stand may be installed. In each embodiment described above, although an example where the first changing room 19 and the second changing room 20 are provided in the radiography room 10 has been described, the technique of the present disclosure is not limited thereto. A changing room may be provided separately from the radiography room 10. A metal detection gate may be provided in a movement path from the changing room to the waiting position to detect whether or not the subject H keeps wearing metal.

The guide voice 152 may be output from the speaker of the imaging room monitor 37 instead of or in addition to the speaker 38. A monitor that displays the guide screen 155 may be attached to the upright imaging stand 31.

Determination regarding whether or not the status of the subject H is proper for radiography may be performed depending on whether or not an unnecessary part, such as a hand, is put in the imaging region IR. Determination regarding whether or not a positional relationship between the radiation source 32 and the electronic cassette 34 is proper for radiography may be performed depending on whether or not a deviation amount between the center of the imaging region IR and the center of the irradiation of the radiation R is equal to or greater than a threshold value set in advance.

The subject H may be imaged with a camera from the lateral surface of the upright imaging stand 31, and the body height of the subject H may be estimated or the degree of close contact of the subject H with the holder 33 may be determined based on an obtained optical image. A body thickness of the subject H may be estimated from an optical image obtained by imaging the subject with a camera from the lateral surface of the upright imaging stand 31, and the irradiation condition may be corrected based on an estimation result. The estimation of the body thickness of the subject H may be performed based on a captured image of a time-of-flight (TOF) camera.

A mechanism that automatically sterilizes spots with which the subject H comes into contact, such as the first changing room 19, the second changing room 20, and the upright imaging stand 31, for example, an ultraviolet irradiation mechanism may be provided. In this case, the mechanism may be operated to perform sterilization each time the subject H is replaced.

The first threshold value TH1 may be changed to a numerical value (eight or the like greater than seven illustrated in FIG. 13) under a more severe condition, and a height of a barrier for determination that the degree of close contact of the subject H with the holder 33 is proper for the radiography may be increased to shift the timing of the radiography. Similarly, the second threshold value TH2 may be changed to a numerical value (100 or the like smaller than 500 illustrated in FIG. 31) under a more severe condition, and a height of a barrier for determination that the degree of stillness of the subject H is proper for the radiography may be increased to shift the timing of the radiography.

Although the electronic cassette 34 is illustrated as a radiographic image detector, the technique of the present disclosure is not limited thereto. A radiographic image detector that is installed to the upright imaging stand 31 may be employed. The radiation source 32 may be a type of being attached to a support provided to be movable in parallel on the floor surface of the radiography room 10, not a ceiling suspension type of suspending from the ceiling 73 of the radiography room 10 by the radiation source suspension device 70.

Various modifications may be made to the hardware configuration of the computer that configures the imaging management device of the present disclosure. For example, the imaging management device may be configured with a plurality of computers separated as hardware for the purpose of improving processing capacity and reliability. For example, the functions of the first image acquisition unit 120, the second image acquisition unit 121, the third image acquisition unit 122, the first image analysis unit 123, the second image analysis unit 124, and the third image analysis unit 125, and the functions of the position adjustment control unit 126, the status recognition unit 127, the entrance control unit 128, the speaker control unit 129, the monitor control unit 130, and the display control unit 131 may be assigned to computers in a distributed manner. In this case, the imaging management device 42 is configured with two computers.

In this way, the hardware configuration of the computer of the imaging management device 42 may be appropriately changed depending on necessary performance, such as processing capacity, safety, and reliability. As well as hardware, an application program, such as the operation program 110, may be of course duplicated or may be stored in a plurality of storages in a distributed manner for the purpose of securing safety and reliability.

In each embodiment described above, for example, as a hardware structure of processing units that executes various kinds of processing, such as the first image acquisition unit 120, the second image acquisition unit 121, the third image acquisition unit 122, the first image analysis unit 123, the second image analysis unit 124, the third image analysis unit 125, the position adjustment control unit 126, the status recognition unit 127, the entrance control unit 128, the speaker control unit 129, the monitor control unit 130, the display control unit 131, and the fourth image analysis unit 190, various processors described below can be used. Examples of various processors include a programmable logic device (PLD) that is a processor capable of changing a circuit configuration after manufacturing, such as a field programmable gate array (FPGA), and a dedicated electric circuit that is a processor having a circuit configuration dedicatedly designed for executing specific processing, such as an application specific integrated circuit (ASIC), in addition to the CPU 97 that is a general-purpose processor configured to execute software (operation program 110) to function as various processing units.

One processing unit may be configured with one of various processors or may be configured with a combination of two or more processors (for example, a combination of a plurality of ASICs and/or a combination of an ASIC and an FPGA) of the same type or different types. A plurality of processing units may be configured with one processor.

As an example where a plurality of processing units are configured with one processor, first, as represented by a computer, such as a client or a server, there is a form in which one processor is configured with a combination of one or more CPUs and software, and the processor functions as a plurality of processing units. Second, as represented by system on chip (SoC) or the like, there is a form in which a processor that implements all functions of a system including a plurality of processing units into one integrated circuit (IC) chip is used. In this way, various processing units may be configured using one or more processors among various processors described above as a hardware structure.

In addition, as the hardware structure of various processors, more specifically, an electric circuit (circuitry), in which circuit elements, such as semiconductor elements, are combined, can be used.

Although the radiography system 30 is illustrated as a medical imaging system, the technique of the present disclosure is not limited thereto. The technique of the present disclosure may be applied to a CT system, a magnetic resonance imaging (MRI) system, a single photon emission computed tomography (SPECT) system, or a positron emission tomography (PET) system, or the like. As well as an aspect where imaging of the medical imaging systems of the same kind is managed, for example, an aspect where imaging of medical imaging systems of different types, such as the radiography system 30 and a CT system, may be made.

The technique of the present disclosure can also be appropriately combined with various embodiments and/or various modification examples described above. The technique of the present disclosure is not limited to each embodiment described above, and various configurations can be of course employed without departing from the spirit and scope of the technique of the present disclosure. In addition to the program, the technique of the present disclosure extends to a storage medium that stores the program in a non-transitory manner. The content of the above description and the content of the drawings are detailed description of portions according to the technique of the present disclosure, and are merely examples of the technique of the present disclosure. For example, the above description relating to configuration, function, operation, and advantageous effects is description relating to examples of configuration, function, operation, and advantageous effects of the portions according to the technique of the present disclosure. Thus, it is needless to say that unnecessary portions may be deleted, new elements may be added, or replacement may be made to the content of the above description and the content of the drawings without departing from the gist of the technique of the present disclosure. Furthermore, to avoid confusion and to facilitate understanding of the portions according to the technique of the present disclosure, description relating to common technical knowledge and the like that does not require particular description to enable implementation of the technique of the present disclosure is omitted from the content of the above description and the content of the drawings.

In the specification, "A and/or B" is synonymous with "at least one of A or B". That is, "A and/or B" may refer to A alone, B alone, or a combination of A and B. Furthermore, in the specification, a similar concept to "A and/or B" applies to a case in which three or more matters are expressed by linking the matters with "and/or".

All of the documents, patent applications, and technical standards in the specification are incorporated herein by reference to the same extent that the individual documents, patent applications, and technical standards are described specifically and independently.

What is claimed is:

1. An imaging management device that manages imaging with a plurality of medical imaging systems installed at a plurality of imaging places, the imaging management device comprising:

a processor, wherein the processor is configured to;

acquire progress status information indicating a progress status of the imaging at each of the plurality of imaging places, the progress status information including imaging preparation completion information indicating that preparation of the imaging is completed and that a timing of the imaging is reached;

notify an operator that the timing of the imaging is reached in response to acquiring the imaging preparation completion information; and perform at least one of access control to the imaging place of a subject to be a target of the imaging or output control of guide information regarding the imaging toward the subject based on the progress status information to shift the timing of the imaging at the plurality of imaging places.

2. The imaging management device according to claim 1, wherein the medical imaging system is a radiography system, and the processor is configured to acquire a position adjustment end signal indicating that adjustment of positions of a radiation source that performs irradiation of radiation and a radiographic image detector that receives the radiation to detect a radiographic image ends, as the imaging preparation completion information.

3. The imaging management device according to claim 1, wherein the processor is configured to acquire a determination result that a status of the subject is proper for the imaging, as the imaging preparation completion information.

4. The imaging management device according to claim 1, wherein the processor is configured to acquire a detection result of body movement by breathing of the subject, and perform control for displaying an animation indicating transition of a breathing state of the subject based on the detection result on a display as the guide information.

5. The imaging management device according to claim 1, wherein the imaging place is at least one of an imaging room for the medical imaging system installed in a medical facility or a traveling examination car in which the medical imaging system is mounted.

6. The imaging management device according to claim 1, wherein the medical imaging system is a radiography system.

7. The imaging management device according to claim 2, wherein the processor is configured to acquire a determination result that a degree of close contact of the subject with an imaging stand on which the subject is positioned for the imaging is proper for the imaging, as the imaging preparation completion information.

8. The imaging management device according to claim 3, wherein the medical imaging system is a radiography system, and the processor is configured to acquire a determination result indicating that an imaging region as a region to be imaged in a radiographic image falls within a detection region for radiation of a radiographic image detector that receives the radiation to detect the radiographic image, as the imaging preparation completion information.

9. The imaging management device according to claim 3, wherein the processor is configured to acquire a determination result that a degree of stillness of the subject is proper for the imaging, as the imaging preparation completion information.

10. A method for operating an imaging management device that manages imaging with a plurality of medical imaging systems installed at a plurality of imaging places, the method comprising:

acquiring progress status information indicating a progress status of the imaging at each of the plurality of imaging places, the progress status information including imaging preparation completion information indicating that preparation of the imaging is completed and that a timing of the imaging is reached;

notifying an operator that the timing of the imaging is
reached in response to acquiring the imaging prepara-
tion completion information; and
performing at least one of access control to the imaging
place of a subject to be a target of the imaging or output
control of guide information regarding the imaging
toward the subject based on the progress status infor-
mation to shift the timing of the imaging at the plurality
of imaging places.
11. A non-transitory computer-readable storage medium
storing an operation program for an imaging management
device that manages imaging with a plurality of medical
imaging systems installed at a plurality of imaging places,
the operation program causing a computer to execute a
process, the process comprising:
acquiring progress status information indicating a prog-
ress status of the imaging at each of the plurality of
imaging places, the progress status information includ-
ing imaging preparation completion information indi-
cating that preparation of the imaging is completed and
that a timing of the imaging is reached;
notifying an operator that the timing of the imaging is
reached in response to acquiring the imaging prepara-
tion completion information; and
performing at least one of access control to the imaging
place of a subject to be a target of the imaging or output
control of guide information regarding the imaging
toward the subject based on the progress status infor-
mation to shift the timing of the imaging at the plurality
of imaging places.

* * * * *